(12) United States Patent
Büscher et al.

(10) Patent No.: US 12,186,344 B2
(45) Date of Patent: *Jan. 7, 2025

(54) CELL POPULATIONS HAVING IMMUNOREGULATORY ACTIVITY, METHOD FOR ISOLATION AND USES

(71) Applicants: TIGENIX, S.A.U., Madrid (ES); CONSEJO SUPERIOR DE INVESTIGACIONES CIENTIFICAS, Madrid (ES)

(72) Inventors: Dirk Büscher, Madrid (ES); Manuel Angel González de la Peña, Madrid (ES); Mario Delgado Mora, Granada (ES)

(73) Assignees: Tigenix, S.A.U., Madrid (ES); Consejo Superior de Investigaciones Cientificas, Madrid (ES)

(*) Notice: Subject to any disclaimer, the term of this patent is extended or adjusted under 35 U.S.C. 154(b) by 147 days.

This patent is subject to a terminal disclaimer.

(21) Appl. No.: 17/659,157

(22) Filed: Apr. 13, 2022

(65) Prior Publication Data
US 2022/0313742 A1  Oct. 6, 2022

Related U.S. Application Data

(60) Continuation of application No. 15/581,801, filed on Apr. 28, 2017, now abandoned, which is a continuation of application No. 14/464,147, filed on Aug. 20, 2014, now Pat. No. 9,943,550, which is a division of application No. 12/067,708, filed as application No. PCT/EP2006/009244 on Sep. 22, 2006, now abandoned.

(30) Foreign Application Priority Data

Sep. 23, 2005  (EP) ..................... 05077186

(51) Int. Cl.
| | | |
|---|---|---|
| A61K 35/35 | (2015.01) | |
| A61K 35/12 | (2015.01) | |
| A61K 39/00 | (2006.01) | |
| C12N 5/0775 | (2010.01) | |
| C12N 5/0783 | (2010.01) | |

(52) U.S. Cl.
CPC .......... *A61K 35/35* (2013.01); *A61K 39/0008* (2013.01); *A61K 39/001* (2013.01); *A61K 39/4611* (2023.05); *A61K 39/4621* (2023.05); *A61K 39/46433* (2023.05); *C12N 5/0636* (2013.01); *C12N 5/0637* (2013.01); *C12N 5/0667* (2013.01); *A61K 2035/122* (2013.01); *A61K 2035/124* (2013.01); *C12N 2501/24* (2013.01)

(58) Field of Classification Search
CPC .. A61K 35/35; A61K 39/0008; A61K 39/001; A61K 2035/122; C12N 5/0667
See application file for complete search history.

(56) References Cited

U.S. PATENT DOCUMENTS

| | | |
|---|---|---|
| 5,145,770 A | 9/1992 | Tubo et al. |
| 5,486,359 A | 1/1996 | Caplan |
| 5,855,619 A | 1/1999 | Caplan et al. |
| 5,976,526 A | 11/1999 | Atala |
| 6,010,696 A | 1/2000 | Caplan et al. |
| 6,174,333 B1 | 1/2001 | Kadiyala et al. |
| 6,368,636 B1 | 4/2002 | McIntosh et al. |
| 6,555,374 B1 | 4/2003 | Gimble et al. |
| 6,777,231 B1 | 8/2004 | Katz et al. |
| 7,078,232 B2 | 7/2006 | Hartzell |
| 7,470,537 B2 | 12/2008 | Hedrick et al. |
| 7,732,126 B2 | 6/2010 | Zhang et al. |
| 8,435,509 B2 | 5/2013 | Brink et al. |
| 8,440,177 B2 | 5/2013 | De La Pena et al. |
| 8,679,834 B2 | 3/2014 | Lombardo et al. |
| 8,790,680 B2 | 7/2014 | Chancellor et al. |
| 8,999,709 B2 | 4/2015 | Fernandez et al. |
| 9,074,190 B2 | 7/2015 | Yoshimura |
| 9,200,255 B2 | 12/2015 | Halvorsen |
| 9,631,176 B2 | 4/2017 | Yoshimura et al. |
| 9,744,267 B2 | 8/2017 | Chancellor et al. |

(Continued)

FOREIGN PATENT DOCUMENTS

| | | |
|---|---|---|
| EP | 1241249 A1 | 7/2004 |
| EP | 1634608 A1 | 3/2006 |

(Continued)

OTHER PUBLICATIONS

Ullah et al. Human mesenchymal stem cells—current trends and future prospective. Bioscience Reports (2015) 35, e00191. p. 1-18 (Year: 2015).*

Ryan J. M., et al., "Mesenchymal stem cells avoid allogeneic rejection", Journal of Inflammation 2(8): 1-11 (Jul. 26, 2005).

Neurath, M.F., et al., "Antibodies to IL-12 abrogate established experimental colitis in mice," J. Exp. Med. 182:1281-1290, Rockefeller University Press, United States (1995).

GenBank, "Human interferon-gamma-inducible indoleamine 2, 3-dioxygenase (IDO) mRNA, complete cds," Accession No. M34455, accessed at https://www.ncbi.nlm.nih.gov/nuccore/M34455, accessed on Aug. 1, 2022, 2 pages.

Mellor, A.L. and Munn, D.H., "IDO expression by dendritic cells: tolerance and tryptophan catabolism," Nat. Rev. Immunol. 4(10):762-774, Nature Publishing Group, Germany (Oct. 2004).

(Continued)

*Primary Examiner* — Taeyoon Kim
(74) *Attorney, Agent, or Firm* — Sterne, Kessler, Goldstein & Fox P.L.L.C.

(57) ABSTRACT

The present invention provides a population of connective tissue derived cells that respond to interferon-gamma (IFN-γ) by expressing indolamine-2,3-dioxygenase (IDO) for use in preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues.

13 Claims, 20 Drawing Sheets

Specification includes a Sequence Listing.

(56) References Cited

U.S. PATENT DOCUMENTS

| | | | |
|---|---|---|---|
| 9,943,550 | B2 | 4/2018 | Buscher et al. |
| 2002/0044923 | A1 | 4/2002 | Mosca et al. |
| 2002/0076400 | A1 | 6/2002 | Katz et al. |
| 2002/0085996 | A1 | 7/2002 | McIntosh et al. |
| 2002/0155104 | A1 | 10/2002 | Munn et al. |
| 2003/0054331 | A1 | 3/2003 | Fraser et al. |
| 2003/0082152 | A1 | 5/2003 | Hedrick et al. |
| 2003/0152558 | A1 | 8/2003 | Luft et al. |
| 2004/0101959 | A1 | 5/2004 | Marko et al. |
| 2004/0180040 | A1 | 9/2004 | Phillips et al. |
| 2004/0204458 | A1* | 10/2004 | Roth .................... A61K 31/517 514/323 |
| 2005/0019911 | A1 | 1/2005 | Gronthos et al. |
| 2005/0048644 | A1 | 3/2005 | Hedrick et al. |
| 2005/0054098 | A1 | 3/2005 | Mistry et al. |
| 2005/0153442 | A1 | 7/2005 | Katz et al. |
| 2005/0221327 | A1 | 10/2005 | Lundgren-Akerlund |
| 2005/0239897 | A1 | 10/2005 | Pittenger et al. |
| 2005/0244963 | A1 | 11/2005 | Teplyashim |
| 2005/0282275 | A1 | 12/2005 | Katz et al. |
| 2006/0045872 | A1 | 3/2006 | Miguel et al. |
| 2006/0047312 | A1 | 3/2006 | Garcia Olmo et al. |
| 2006/0073124 | A1 | 4/2006 | Garcia Castro et al. |
| 2006/0239980 | A1 | 10/2006 | Miana et al. |
| 2006/0286089 | A1 | 12/2006 | Berenson et al. |
| 2007/0178071 | A1 | 8/2007 | Westenfelder et al. |
| 2007/0248580 | A1 | 10/2007 | Garcia Castro et al. |
| 2008/0050349 | A1 | 2/2008 | Steward |
| 2008/0095749 | A1 | 4/2008 | Aggarwal et al. |
| 2009/0292311 | A1 | 11/2009 | Garcia Olmo et al. |
| 2010/0172885 | A1 | 7/2010 | Pittenger et al. |
| 2010/0209403 | A1 | 8/2010 | Meiron et al. |
| 2011/0262402 | A1 | 10/2011 | Kuroda et al. |
| 2012/0269774 | A1 | 10/2012 | Ichim et al. |
| 2014/0134140 | A1 | 5/2014 | Caplan et al. |
| 2015/0224146 | A1 | 8/2015 | Buscher et al. |
| 2017/0296585 | A1 | 10/2017 | Garcia Castro et al. |

FOREIGN PATENT DOCUMENTS

| | | | |
|---|---|---|---|
| EP | 1803472 | A1 | 7/2007 |
| EP | 2292736 | A2 | 3/2011 |
| EP | 2292737 | A1 | 3/2011 |
| EP | 1926813 | B1 | 6/2016 |
| ES | 2264862 | A1 | 1/2007 |
| ES | 2313805 | A1 | 3/2009 |
| JP | 2002502823 | A | 1/2002 |
| JP | 2002537849 | A | 11/2002 |
| JP | 2003523323 | A | 8/2003 |
| WO | WO-9623058 | A1 | 8/1996 |
| WO | WO-9928444 | A1 | 6/1999 |
| WO | WO-1999028444 | A1 | 6/1999 |
| WO | WO-199939726 | A1 | 8/1999 |
| WO | WO-1999051275 | A2 | 10/1999 |
| WO | WO-0053795 | A1 | 9/2000 |
| WO | WO-200139784 | A1 | 6/2001 |
| WO | WO-02067867 | A2 | 9/2002 |
| WO | WO-2003022988 | A2 | 3/2003 |
| WO | WO-2003024215 | A1 | 3/2003 |
| WO | WO-03040346 | A2 | 5/2003 |
| WO | WO-2004090095 | A2 | 10/2004 |
| WO | WO-2004111208 | A1 | 12/2004 |
| WO | WO-2005035738 | A1 | 4/2005 |
| WO | WO-2005042730 | A2 | 5/2005 |
| WO | WO-2005062857 | A2 | 7/2005 |
| WO | WO-2005070090 | A2 | 8/2005 |
| WO | WO-2005093044 | A1 | 10/2005 |
| WO | WO-2006037649 | A1 | 4/2006 |
| WO | WO-2006136244 | A2 | 12/2006 |
| WO | WO-2007039150 | A2 | 4/2007 |
| WO | WO-2008036374 | A2 | 3/2008 |
| WO | WO-2008116157 | A2 | 9/2008 |
| WO | WO-2009050282 | A1 | 4/2009 |
| WO | WO-2010015929 | A2 | 2/2010 |
| WO | WO-2010112662 | A1 | 10/2010 |
| WO | WO-2012095743 | A2 | 7/2012 |
| WO | WO-2012123401 | A1 | 9/2012 |
| WO | WO-2014140362 | A2 | 9/2014 |
| WO | WO-2014207679 | A1 | 12/2014 |

OTHER PUBLICATIONS

Horwitz, E.M., et al., Mesenchymal Stromal Cells, Curr. Opin. Hematol. 13(6):419-425, Lippincott Williams and Wilkins Ltd., United States (2006).

Poggioli, G., et al., "Infliximab in the treatment of Crohn's disease," Ther. Clin. Risk. Manag. 3(2):301-308, Dove Press, United Kingdom (2007).

Dave, M., et al., "Mesenchymal Stem Cell Therapy for Inflammatory Bowel Disease A Systematic Review and Meta-analysis," Inflamm. Bowel Dis. 21(11):2696-2707, Oxford University Press, United Kingdom (2015).

Zhang, et al., Yin and yang interplay of IFN-gamma in inflammation and autoimmune disease. J. Clin. Invest. 117:871-873, American Society for Clinical Investigation, United States (2007).

Hawkey, C.J., et al., "Stem cell transplantation for inflammatory bowel disease: practical and ethical issues," Gut 46:869-872, BMJ, United Kingdom (2000).

Zuk, P.A., et al., "Multilineage cells from human adipose tissue: implications for cell-based therapies," Tissue Eng. 7:211-228, Mary Ann Liebert, Inc., United States (2001).

Gronthos, S., et al., "Surface Protein Characterization of Human Adipose Tissue-Derived Stromal Cells," J. Cell. Physiol. 189:54-63, Wiley, United States (2001).

Jorgensen, C., et al., "Stem cells for repair of cartilage and bone: the next challenge in osteoarthritis and rheumatoid arthritis," Ann. Rheum. Dis. 60:305-309, BMJ, United Kingdom (2001).

Liao, L.M., et al., "Application of Mesenchymal Stem Cell in Immunotherapy—review," Zhongguo Shi Yan Xue Ye Xue Za Zhi 13:158-163, Haidian-qu, China (Feb. 2005).

Djouad, F., et al., "Reversal of the immunosuppressive properties of mesenchymal stem cells by tumor necrosis factor alpha in collagen-induced arthritis," Arthritis Rheum. 52(5):1595-1603, Wiley, United States (May 2005).

Gimble, J.M., "Adipose tissue-derived therapeutics," Expert Opin. Biol. Ther. 3(5):705-713, Taylor & Francis, United Kingdom (Aug. 2003).

Garcia-Olmo, D., et al., "Autologous stem cell transplantation for treatment of rectovaginal fistula in perianal Crohn's disease: a new cell-based therapy," Int. J. Colorectal Dis. 18(5):451-454, Springer, Germany (Sep. 2003).

Jorgensen, C., et al., "Mesenchymal stem cells and rheumatoid arthritis," Joint Bone Spine. 70(6):483-485, Elsevier, Netherlands (Dec. 2003).

De Ugarte, D.A., et al., "Differential expression of stem cell mobilization-associated molecules on multi-lineage cells from adipose tissue and bone marrow," Immunol. Lett. 89(2-3):267-270, Elsevier, Netherlands (Oct. 2003).

Gimble, J.M., et al., "Bone and fat: old questions, new insights," Endocrine 23(2-3):183-188, Springer Science+Business Media, Germany (Mar. 2004).

Chung, N.G., et al., "Cotransplantation of marrow stromal cells may prevent lethal graft-versus-host disease in major histocompatibility complex mismatched murine hematopoietic stem cell transplantation," International Journal of Hematology 80(4):370-376, Springer Science+Business Media, Germany (Nov. 2004).

Aggarwal, S., et al., "Human mesenchymal stem cells modulate allogeneic immune cell responses," Blood. 105(4):1815-1822, American Society of Hematology, United States (Feb. 2005; Epub. Oct. 2004).

Garcia-Olmo, D., et al., "A Phase I Clinical Trial of the Treatment of Crohn's Fistula by Adipose Mesenchymal Stem Cell Transplantation," Dis. Colon. Rectum. 48(7):1416-1423, Lippincott Williams & Wilkins, United States (Jul. 2005).

(56) References Cited

OTHER PUBLICATIONS

Strem, B.M., et al., "Multipotential differentiation of adipose tissue-derived stem cells," Keio. J. Med. 54 (3): 132-141, Keio University School of Medicine, Japan (Sep. 2005).

Djouad, F., et al., "Transcriptional profiles discriminate bone marrow-derived and synovium-derived Mesenchymal stem cells," Arthritis Res. Ther. 7(6):R1304-1315, BioMed Central, United Kingdom (Sep. 20, 2005).

Barry, F.P., et al., "Immunogenicity of adult mesenchymal stem cells: lessons from the fetal allograft," Stem Cells Dev. 14(3):252-265, Mary Ann Liebert, Inc. United States (Jun. 2005).

Krampera, M., et al., "Role for interferon-gamma in the immunomodulatory activity of human bone marrow mesenchymal stem cells," Stem Cells. 24(2):386-398, Wiley, United States (2006).

McIntosh, K., et al., "The Immunogenicity of Human Adipose-Derived Cells: Temporal Changes In Vitro," Stem Cells. 24(5):1246-1253, Wiley, United States (2006).

Coombs, A., "Questioning the self cell," Nature Reports Stem Cells pp. 1-6, Nature Portfolio, Germany (2008).

Wolf, D., et al., "Regenerative capacity of intravenous autologous, allogeneic and human mesenchymal stem cells in the infarcted pig myocardium-complicated by myocardial tumor formation," Scand. Cardiovasc. J. 43(1):39-45, Taylor & Francis, United Kingdom (2009).

Newman, R.E., et al., "Treatment of Inflammatory Diseases with Mesenchymal Stem Cells," Inflamm. Allergy Drug Targets. 8(2):110-123, Bentham Science, United Arab Emirates (2009).

Niehage, C., et al., "The Cell Surface Proteome of Human Mesenchymal Stromal Cells" PLoS One. 6(5):e20399, PLOS, United States (2011).

Wakao, S., et al., "Regenerative Effects of Mesenchymal Stem Cells: Contribution of Muse Cells, a Novel Pluripotent Stem Cell Type that Resides in Mesenchymal Cells," Cells 1(4):1045-1060, Cell Press, United States (2012).

National Institute of Health News in Health, "Understanding Autoimmune Diseases," accessed at https://newsinhealth.nih.gov/2012/06/understanding-autoimmune-diseases, Oct. 2012, 5 pages.

Office Action for Japanese Patent Application No. 2008-531620, dated Jan. 11, 2013.

El Atat, O., et al., "An Evaluation of the Stemness, Paracrine, and Tumorigenic Characteristics of Highly Expanded, Minimally Passaged Adipose-Derived Stem Cells," PLoS ONE 11(9):e0162332, PLOS, United States (2016).

Arthritis Center, Rheumatoid Arthritis Preventable? Johns Hopkins Arthritis Center, John Hopkins Arthritis Center, accessed at http://www.hopkinsarthritis.org/sk-the-expert/rheumatoid-arthritis-preventable/, Apr. 26, 2007, 1 page.

Melief, S.M., et al., "Adipose tissue-derived multipotent stromal cells have a higher immunomodulatory capacity than their bone marrow-derived counterparts," Stem Cells Transl. Med. 2(6):455-463, Oxford University Press, United Kingdom (2013).

Leblanc, K., et al., "HLA expression and immunologic properties of differentiated and undifferentiated mesenchymal stem cells," Exp. Hematol. 31(10):890-896, Elsevier, Netherlands (Oct. 2003).

Zhao, R.C., et al., "Mechanisms of and perspectives on the mesenchymal stem cell in immunotherapy," J. Lab. Clin. Med. 143(5):284-291, Elsevier, Netherlands (May 2004).

Meisel, R., et al., "Human bone marrow stromal cells inhibit allogeneic T-cell responses by indoleamine 2,3-dioxygenase-mediated tryptophan degradation," Blood 103(12):4619-4621, American Society of Hematology, United States (Jun. 2004).

Cui, L., et al., "[Human adipose derived stem cells suppress lymphocyte proliferation induced by cellular or nonspecific mitogenic stimuli]," Zhonghua Yi Xue Za Zhi. 85(27):1890-1894, English Abstract only, Zhonghua yi xue hui, Taiwan (Jul. 2005).

Puissant, B., et al., "Immunomodulatory effect of human adipose tissue-derived adult stem cells: comparison with bone marrow mesenchymal stem cells," Br. J. Haematol. 129(1):118-129, Wiley-Blackwell, United States (Mar. 2005).

Office Action in Canadian Patent Application No. 2,623,353, dated Mar. 10, 2015.

Delarosa, O., et al., "Human adipose-derived stem cells impair natural killer cell function and exhibit low susceptibility to natural killer-mediated lysis," Stem Cells Dev. 21(8):1333-1343, Mary Ann Liebert, Inc., United States (2012).

Le Blanc, K., et al., "Immunobiology of human mesenchymal stem cells and future use in hematopoietic stem cell transplantation," Biol. Blood Marrow Transplant. 11:321-334, Elsevier, Netherlands (May 2005).

Maccario, R., et al., "Interaction of human mesenchymal stem cells with cells involved in alloantigen-specific immune response favors the differentiation of CD4+ T-cell subsets expressing a regulatory/suppressive phenotype," Haematologica J. 90(4):516-525, Ferrata Storti Foundation, Italy (Apr. 2005).

Barry, F.P., et al., "Mesenchymal Stem Cell Transplantation for Tissue Repair," Semin. Plast. Surg. 19:229-239, Thieme Medical Publishers, Germany (Aug. 2005).

Lee, R. H., et al., "Characterization and expression analysis of mesenchymal stem cells from human bone marrow and adipose tissue," Cell Physiol. Biochem. 14:311-324, Karger Publishers, Switzerland (Aug. 2004).

Jung, D., et al., "A comparison of autologous and allogenic bone marrow-derived mesenchymal stem cell transplantation in canine spinal cord injury," J. Neurol. Sci. 285:67-77, Elsevier, Netherlands (2009).

European Notice of Opposition in European Patent Application No. 06777197.2, mailed Mar. 16, 2017.

Chinese Reexamination Notice in Chinese Patent Application No. 200680043425.4, mailed Sep. 29, 2016.

Zuk, P.A., et al., "Human adipose tissue is a source of multipotent stem cells," Mol. Biol. Cell. 13:4279-4295, American Society for Cell Biology, United States (2002).

Rogers, J.J., et al., "Differentiation factors induce expression of muscle, fat, cartilage, and bone in a clone of mouse pluripotent mesenchymal stem cells," Am. Surg. 61(3):231-236, Elsevier, Netherlands (1995).

Roughley, P.J., "The Structure and Function of Cartilage Proteoglycans," Eur. Cells. Mater. 12:92-101, the AO Research Institute Davos, Switzerland (2006).

Safwani, W.K., et al., "The changes of stemness biomarkers expression in human adipose-derived stem cells during long-term manipulation," Biotechnol. Appl. Biochem. 58(4):261-270, International Union of Biochemistry and Molecular Biology (2011).

Sanchez-Ramos, J., et al., "Adult Bone Marrow Stromal Cells Differentiate into Neural Cells in Vitro," 2000, Exp. Neurol. 164(2):247-256, Elsevier, Netherlands (2000).

Sanz-Baro, R., et al., "First-in-Human Case Study: Pregnancy in Women With Crohn's Perianal Fistula Treated With Adipose-Derived Stem Cells: A Safety Study," Stem Cells Transl. Med. 4(6):598-602, Oxford University Press, United Kingdom (2015).

Schreml, S., et al., "Harvesting human adipose tissue-derived adult stem cells: resection versus liposuction," Cytotherapy 11(7): pp. 947-957, Elsevier, Netherlands (2009).

Shen, Z.L., et al., " A Schwann cell-seeded intrinsic framework and its satisfactory biocompatibility for a bioartificial nerve graft," Microsurgery 21(1):6-11, Wiley, United States (2001).

Shimizu, K., et al., "Newly developed primary culture of rat visceral adipocytes and their in vitro characteristics," Cell. Biol. Int. 30(4):381-388, Portland Press, United Kingdom (2006).

Silva, G.V., et al., "Mesenchymal stem cells differentiate into an endothelial phenotype, enhance vascular density, and improve heart function in a canine chronic ischemia model," Circulation 111(2):150-156, Lippincott Williams & Wilkins, United States (Jan. 2005).

Stanford, C.M., et al., "Rapidly forming apatitic mineral in an osteoblastic cell line (UMR 106-01 BSP)," J. Biol. Chem. 270(16):9420-9428, American Society for Biochemistry and Molecular Biology, United States (1995).

TiGenix Press Release on Aug. 2, 2016, "Takeda and TiGenix Announce Publication in The Lancet of 24 Week Results of the Phase 3 ADMIRE-CD Trial Investigating Cx601 in the Treatment of Complex Perianal Fistulas in Patients with Crohn's Disease," Takeda.com, accessed at https://www.takeda.com/newsroom/newsreleases/2016/Takeda-and-TiGenix-Announce-Publication-in-The-Lancet-of-24-Week/, 5 pages.

(56) References Cited

OTHER PUBLICATIONS

Thankamony, S.P., et al., "Enforced hematopoietic cell E- and L-selectin ligand (HCELL) expression primes transendothelial migration of human mesenchymal stem cells," PNAS 108:2258-63, National Academy of Sciences, United States (2011).

Third Party Submissions, dated May 15, 2014, submitted in U.S. Appl. No. 14/017,152, 13 pages.

Toledo, L.S., et al., "Lipoplasty," Clin. Plast. Surg. 33(1):55-62, Elsevier, Netherlands (2006).

Toma, C., et al., "Human mesenchymal stem cells differentiate to a cardiomyocyte phenotype in the adult murine heart," Circulation 105:93-98, Lippincott Williams & Wilkins, United States (2002).

Torensma, R., et al., "The Impact of Cell Source, Culture Methodology, Culture Location and Individual Donors on Gene Expression Profiles of Bone Marrow-Derived and Adipose-Derived Stromal Cells," Stem Cell Dev. 22(7):1086-1096, Mary Ann Liebert, Inc., United States (2013).

Van, R.L., et al., "Cytological and Enzymological Characterization of Adult Human Adipocyte Precursors in Culture," J. Clin. Invest. 58(3):699-704, American Society for Clinical Investigation, United States (1976).

Vivotecnia Research S.L. "Isolation, propagation and characterization of human mesenchymal stem cells", Final Report N-01191, Mar. 23, 2011.

Wabitsch, M. et al., "IGF-I- and IFGBP-3-Expression in Cultured Human Preadipocytes and Adipocytes," Horm. Metab. Res. 32(11-12):555-559, Georg Thieme Verlag, Germany (2000).

Wakitani, S., et al., "Myogenic cells derived from rat bone marrow mesenchymal stem cells exposed to 5-azacytidine," Muscle Nerve 18(12): 1417-1426, Wiley, United States (1995).

Winter, A., et al., "Cartilage-like gene expression in differentiated human stem cell spheroids: a comparison of bone marrow-derived and adipose tissue-derived stromal cells," Arthritis Rheum. 48(2):418-429, Wiley, United States (Feb. 2003).

Xu, Y., et al., "Connective tissue growth factor in regulation of RhoA mediated cytoskeletal tension associated osteogenesis of mouse adipose-derived stromal cells," PLoS One 5(6):e11279, PLOS, United States (2010).

Yoo, J.U., et al., "The role of osteochondral progenitor cells in fracture repair," Clin. Orthop. Relat. Res. 355S:S73-S81, Springer Science+Business Media, Germany (1998).

Yoshimura, K., et al., "Characterization of freshly isolated and cultured cells derived from the fatty and fluid portions of liposuction aspirates," J. Cell. Physiol. 208:64-76, Wiley, United States (2006).

Young, M.J., et al., "Neuronal differentiation and morphological integration of hippocampal progenitor cells transplanted to the retina of immature and mature dystrophic rats," Mol. Cell. Neurosci. 16(3):197-205, Elsevier, Netherlands (2000).

Young, R.G., et al., "Use of Mesenchymal Stem Cells in a Collagen Matrix for Achilles Tendon Repair," J. Orthop. Res. 16(4): 406-413, Wiley, United States (1998).

Zannettino, A.C.W., et al., "Multipotential human adipose-derived stromal stem cells exhibit a perivascular phenotype in vitro and in vivo," J. Cell. Phys. 214(2):413-421, Wiley, United States (2008).

Zarapico, M., et al., "La asociación fibrino-desoxiribonucleasa en la profilaxis de las adherencias peritoneales postoperalorias," Caledra de Palologia Quirúrgica, 4(20) (1972).

Zhao, Y., et al., "The effect of serial passaging on the proliferation and differentiation of bovine adipose-derived stem cells," Cells Tissues Organs 195(5):414-427, Karger Publishers, Switzerland (2012).

Zilberfarb, V., et al., "Human immortalized brown adipocytes express functional beta3-adrenoceptor coupled to lipolysis," J. Cell. Sci. 110:801-807, The Company of Biologists, United Kingdom (1997).

Zimmerlin, L., et al., "Stromal vascular progenitors in adult human adipose tissue," Cytometry A. 77(1):22-30, Wiley, United States (2010).

Kim, Y.J., et al., "Role of CD9 in proliferation and proangiogenic action of human adipose-derived mesenchymal stem cells," Pflugers Arch., vol. 455(2):283-296—Abstract Only, Springer Science+Business Media, Germany (2007).

Kuruvilla, A.P., et al., "Protective effect of transforming growth factor beta 1 on experimental autoimmune diseases in mice," Proc. Natl. Acad. Sci. 88(7):2918-2921, National Academy of Sciences, United States (1991).

Mellor, A.L., et al., "IDO expression by dendritic cells: tolerance and tryptophan catabolism" Nat. Rev. Immunol. 4(10):762-774, Nature Portfolio, Germany (Oct. 2004).

Neurath, M.F., et al., "Antibodies to interleukin 12 abrogate established experimental colitis in mice," J. Exp. Med. 182(5):1281-1290, Rockefeller University Press, United States (1995).

Garcia-Olmo, D., et al., "Treatment of enterocutaneous fistula in Crohn's Disease with adipose-derived stem cells: a comparison of protocols with and without cell expansion," Int. J. Colorectal. Dis. 24:27-30, Springer, Germany (2009).

Garcia-Olmo, D., et al., "Cumulative Evidence That Mesenchymal Stem Cells Promote Healing of Perianal Fistulas of Patients With Crohn's Disease—Going From Bench to Bedside," Gastroenterology 149(4): pp. 853-857, Elsevier, Netherlands (2015).

Garcia-Olmo, D., et al., "The Vulture and Stem Cells," N. Engl. J. Med. 349:1480-1481, Massachusetts Medical Society, United States (Oct. 2003).

Gimble, J.M., et al., "Differentiation Potential of Adipose Derived Adult Stem (ADAS) Cells," Curr. Top. Dev. Biol. 58:137-160, Elsevier, Netherlands (Dec. 2003).

Gimble, J.M., et al., "Adipose-derived adult stem cells: isolation, characterization, and differentiation potential," Cytotherapy. 5(5):362-369, Elsevier, Netherlands (2003).

Gimble, J.M., et al., "Isolation and Growth of Stem Cells," Chapter 6 in Tissue Engineering, Pallua, N., and Suschek, C.V., eds., pp. 93-111, Springer, Germany (2011).

Gokhale, A., et al., "Immunosuppression by co-stimulatory molecules: inhibition of CD2-CD48/CD58 interaction by peptides from CD2 to suppress progression of collagen-induced arthritis in mice," Chem. Biol. Drug. Des. 82:106-118, Wiley, United States (2013).

Gomillion, C.T., et al., "Stem cells and adipose tissue engineering," Biomaterials. 27(36):6052-6063, Elsevier, Netherlands (2006).

Gonzalez, M.A., et al., "Adipose-derived mesenchymal stem cells alleviate experimental colitis by inhibiting inflammatory and autoimmune responses," Gastroenterology. 136(3):978-989, Elsevier, Netherlands (2009).

Gowda et al., "Production of Good Manufacturing Practice Grade Equine Adipose=derived Mesenchymal Stem Cells or Therapeutic Use," J. Stem. Cell Res. Ther. 3:5, BioMed Central, United Kingdom (2013).

Guilak, F., et al., "Clonal Analysis of the Differentiation of Potential of Human Adipose-Derived Adult Stem Cells," J. Cell. Physiol. 206(1): pp. 229-237, Wiley, United States (2006).

Halme, D.G., et al.; "FDA Regulation of Stem-Cell-Based Therapies," N. Engl. J. Med. 355:1730-1735, Massachusetts Medical Society, United States (2006).

Handbook of CDA classification, 7th HLDA, 2000, 200-202.

Hattori, H., et al., "Osteogenic potential of human adipose tissue-derived stromal cells as an alternative stem cell source," Cells Tissues Organs. 178(1):2-12, Karger Publishers, Switzerland (Nov. 2004).

Hauner, H., et al., "Promoting effect of glucocorticoids on the differentiation of human adipocyte precursor cells cultured in a chemically defined medium," J. Clin. Invest. 84(5):1663-1670, American Society for Clinical Investigation, United States (1989).

Haynesworth, S.E., et al., "Characterization of Cells with Osteogenic Potential from Human Marrow," Bone. 13:81-88, Elsevier, Netherlands (1992).

Herreros, M.D., et al., "Autologous expanded adipose-derived stem cells for the treatment of complex cryptoglandular perianal fistulas: a phase III randomized clinical trial (FATT 1: fistula Advanced Therapy Trial 1) and long-term evaluation," Dis. Colon. Rectum. 55(7):762-772, Lippincott Williams & Wilkins, United States (2012).

Horwitz, E.M., et al., "Isolated allogeneic bone marrow-derived mesenchymal cells engraft and stimulate growth in children with

(56) References Cited

OTHER PUBLICATIONS osteogenesis imperfecta: Implications for cell therapy of bone," PNAS, 99(13): 8932-8937, National Academy of Sciences, United States (2002).
Huang, X.P., et al., "Differentiation of allogeneic mesenchymal stem cells induces immunogenicity and limits their long-term benefits for myocardial repair," Circulation.122(23):2419-29, Lippincott Williams & Wilkins, United States (2010).
Ikegame, Y., et al., "Comparison of mesenchymal stem cells from adipose tissue and bone marrow for ischemic stroke therapy," Cytotherapy 13(6):675-685, Elsevier, Netherlands (2011).
Ishimura, D., "Differentiation of adipose-derived stromal vascular fraction culture cells into chondrocytes using the method of cell sorting with a mesenchymal stem cell marker," Tohoku. J. Exp. Med. 216(2):149-156, Tohoku Imperial University College of Medicine, Japan (2008).
Ivanova, N.B., et al., "A Stem Cell Molecular Signature," Science 298:601-604, American Association for the Advancement of Science, United States (2002).
Jiang, Y., et al., "Multipotent progenitor cells can be isolated from postnatal murine bone marrow, muscle, and brain," Exp. Hematol. 30(8):896-904, Elsevier, Netherlands (2002).
Karl, C., et al., "Neuronal precursor-specific activity of human doublecortin regulatory sequence," J. Neurochem. 92(2):264-282, Wiley-Blackwell, United States (Jan. 2005).
Song, K.H., "New Techniques for Treating an Anal Fistula," J. Korean Soc. Coloproctol. 28(1): pp. 7-12, The Korean Society of Coloproctology, Korea (2012).
Kim, Y., et al., "Direct Comparison of Human Mesenchymal Stem Cells Derived from Adipose Tissues and Bone Marrow in Mediating Neovascularization in Response to Vascular Ischemia," Cell. Physiol. Biochem. 20: 867-876, Karger Publishers, Switzerland (2007).
Kurita, M., et al., "Influences of Centrifugation on Cells and Tissues in Liposuction Aspirates: Optimized Centrifugation for Lipotransfer and Cell Isolation," Plast. Reconstr. Surg. 121(3):1033-1041, Lippincott Williams & Wilkins, United States (2008).
Lee, Y., et al., "DNA Ligase IV Suppresses Medulloblastoma Formation," Cancer Res. 62(22):6395-6399, American Association for Cancer Research, United States (2002).
Lendeckel, S., et al., "Autologous stem cells (adipose) and fibrin glue used to treat widespread traumatic calvarial defects: case report," J. Craniomaxillofac. Surg. 32(6):370-373, Elsevier, Netherlands (Dec. 2004).
Levy, C., et al., "Management of Internal Fistulas in Crohn's Disease," Inflamm. Bowel Dis. 8(2):106-111, Oxford University Press, United Kingdom (2002).
Liu, J., et al., "Autologous stem cell transplantation for myocardial repair," Am. J. Physiol. Heart. Circ. Physiol. 287(2):H501-H511, American Physiological Society, United States (Aug. 2004).
Lund, P., et al., "Effect of growth media and serum replacements on the proliferation and differentiation of adipose-derived stem cells," Cytotherapy. 11(2):189-197, Elsevier, Netherlands (2009).
Matsubara, H., "Risk to the coronary arteries of intracoronary stem cell infusion and G-CSF cytokine therapy," Lancet 363(9411):746-747, Elsevier, Netherlands (Mar. 2004).
Minteer, D., et al., "Adipose-Derived Mesenchymal Stem Cells: Biology and Potential Applications," Adv. Biochem. Eng. Biotechnol. 129:59-71, Springer, Germany (2013).
Mizuno, H., et al., "Mesengic potential and future clinical perspective of human processed lipoaspirate cells," J. Nippon. Med. Sch. 70(4): pp. 300-306, Medical Association of Nippon Medical School, Japan (Aug. 2003).
Mizuno, H., et al., "Myogenic Differentiation by Human Processed Lipoaspirate Cells," Plast. Reconstr. Surg. 109(1):199-209, Lippincott Williams & Wilkins, United States (2002).
Mizuno, H., "Versatility of Adipose Tissue as a Source of Stem Cells," J. Nippon. Med. Sch. 70(5):428-231, Medical Association of Nippon Medical School, Japan (Oct. 2003).

Morrison, S.J., et al., "The Biology of Hematopoietic Stem Cells," Annu. Rev. Cell Dev. Biol. 11:35-71, Annual Reviews, United States (1995).
Office Action mailed on Feb. 3, 2011, in U.S. Appl. No. 11/167,061, Miguel, M.J., et al., filed Jun. 24, 2005, 9 pages.
Osawa, M., et al.; "Long-term lymphohematopoietic reconstitution by a single CD34-low/negative hematopoietic stem cell," Science 273(5272):242-245, American Association for the Advancement of Science, United States (1996).
Overton, W., et al., "Modified Histogram Subtraction Technique for Analysis of Flow Cytometry Data," Cytometry 9:619-626, Wiley, United States (1998).
Panes, J., et al., "Expanded allogeneic adipose-derived mesenchymal stem cells (Cx601) for complex perianal fistulas in Crohn's disease: a phase 3 randomized, double-blind controlled trial," Lancet 388(10051):1281-1290, Elsevier, Netherlands (2016).
Pascual, I., et al., "Adipose-derived mesenchymal stem cells in biosutures do not improve healing of experimental colonic anastomoses," Br. J. Surg, 95(9):1180-1184, Oxford University Press, United Kingdom (2008).
Penninckx, F., et al., "Advancement flap plasty for the closure of anal and recto-vaginal fistulas in Crohn's disease," Acta. Gastroenterol. Belg. 64(2):223-226, Universa Press, Belgium (2001).
Phillips, R.L., "Investigating the Genetic Control of Stem Cell Behavior," Curr. Top. Microbiol. Immunol. 251:13-19, Springer, Germany (2000).
Pittenger, M.E., et al., "Multilineage Potential of Adult Human Mesenchymal Stem Cells," Science 284(5411):143-147, American Association for the Advancement of Science, United States (1999).
Rajashekhar, G., et al., "IFATS Collection: Adipose Stromal Cell Differentiation Is Reduced by Endothelial Cell Contact and Paracrine Communication: Role of Canonical Wnt Signaling," Stem Cells. 26(10):2674-81, Oxford University Press, United Kingdom (2008).
Ramalho-Santos, M., et al., "Stemness: Transcriptional Profiling of Embryonic and Adult Stem Cells," Science 298(5593):597-600, American Association for the Advancement of Science, United States (2002).
"Reflection paper on stem cell-based medicinal products," Committee for Advanced Therapies—European Medicines Agency, EMA/CAT/571134/2009, Jan. 14, 2011, 14 pages.
Zuk, P.A., et al., "The Adipose-derived Stem Cell: Looking Back and Looking Ahead," Mol. Biol. Cell. 21(11):1783-1787, American Society for Cell Biology, United States (2010).
Chen, W., et al., "Manipulation of TFG-Beta to control autoimmune and chronic inflammatory diseases," Microbes Infect. 1(15):1367-1380, Elsevier, Netherlands (1999).
Fung, E., et al., "Multiplexed immunophenotyping of human antigen-presenting cells in whole blood by polychromatic low cytometry," Nat. Protoc. 5(2):357-370, Nature Portfolio, Germany (2010).
Jewett, A., et al., "Strategies to rescue mesenchymal stem cells (MSCs) and dental pulp stem cells (DPSCs) from NK cell mediated cytotoxicity," PLOS One. 5(3): e9874, PLOS, United States (2010).
Kallistratova, D., 125:59-72, Akademii Nauk SSSR, Russia (1959).
Kern, S., et al., "Comparative analysis of mesenchymal stem cells from bone marrow, umbilical cord blood, or adipose tissue," Stem Cells. 24(5):1294-1301, Oxford University Press, United Kingdom (2006).
Rius, J., et al., "Gracilis transposition in complicated perianal fistula and unhealed perineal wounds in Crohn's disease," Eur. J. Surg. 166(3):218-222, Elsevier, Netherlands (2000).
Lazarus, H., et al., "Role of Mesenchymal Stem Cells (MSC) In Allogeneic Transplantation Early Phase I Clinical Results," Blood. 96(11):392A, The American Hematological Society, United States (2000).
Peng, L., et al., "Comparative Analysis of Mesenchymal Stem Cells from bone Marrow, Cartilage, and Adipose Tissue," Stem Cells Dev. 17:761-774, Mary Ann Liebert, Inc. United States (2008).
Roebuck, K.A., et al., "Regulation of intercellular adhesion molecule-1 (CD54) gene expression," J. Leukoc. Biol. 66(6):876-888, Society for Leukocyte Biology, United States (1999).
Rojewski, M.T., et al., "Phenotypic Characterization of Mesenchymal Stem Cells from Various Tissues," Transfus. Med. Hemother. 35(3):168-184, Karger Publishers, Switzerland (2008).

(56) References Cited

OTHER PUBLICATIONS

Romanov, Y.A., et al., "Mesenchymal Stem Cells from Human Bone Marrow and Adipose Tissue: Isolation, Characterization, and Differentiation Potentialities," Bull. Exp. Biol. Med. 140(1):138-143, Springer New York, United States (Jul. 2005).
Sotiropoulou, P.A., et al., "Interactions between human mesenchymal stem cells and natural killer cells," Stem Cells. 24(1):74-85, Oxford University Press, United Kingdom (Jan. 2005).
Spaggiari, G.M., et al., "Mesenchymal stem cell-natural killer cell interactions: evidence that activated NK cells are capable of killing MSCs, whereas MSCs can inhibit IL-2-induced NK-cell proliferation," Blood. 107:1484-1490, American Society of Hematology, United States (Feb. 2005).
Vucic, V., et al., "Effects of gamma-radiation on cell growth, cycle arrest, death, and superoxide dismutase expression by DU 145 human prostate cancer cells," Braz. J. Med. Biol. Res. 39:227-236, Associacao Brasileira de Divulgacao Cientifica, Brazil (2006).
Wagner, W., et al., "Comparative characteristics of mesenchymal stem cells from human bone marrow, adipose tissue, and umbilical cord blood," Exp. Hematol. 33(11):1402-1416, Elsevier, Netherlands (Nov. 2005).
Friedenstein, A.J., et al., "Fibroblast Precursors in Normal and Irradiated Mouse Hematopoietic Organs," Exp. Hematol. 4(5):267-274, Elsevier, Netherlands (1976).
Abedi, M., et al., "Critical variables in the conversion of marrow cells to skeletal muscle," Blood. 106(4):1488-1494, American Society of Hematology, United States (Aug. 2005).
Abkowitz, J.L., "Can Human Hematopoietic Stem Cells Become Skin, Gut or Liver Cells?" N. Engl. J. Med. 346(10): 770-772, Massachusetts Medical Society, United States (2002).
Affymetrix eBioscience, "Mouse CD Chart," accessed at http://www.ebioscience.com/resources/mouse-cd-chart.htm, Oct. 16, 2015.
Alvarez, D.F., et al. "Publishing flow cytometry data," Am. J. Physiol. Lung Cell Mol. Physiol. 298:L127-L130, American Physiological Society, United States (2010).
"American Gastroenterological Association medical position statement: perianal Crohn's disease," Gastroenterology 125(5):1503-1507, Elsevier, Netherlands (Nov. 2003).
Asencio, A.F., "Aproximación a los métodos de estudio de las anastomosis intestinales experimentales: Métodos bioquímicos, feísicos y microangiográcos," Cirugia Española 6:805-810, Elsevier, Netherlands (1989).
Astori, G., et al., "In vitro" and multicolor phenotypic characterization of cell subpopulations identified in fresh human adipose tissue stromal vascular fraction and in the derived mesenchymal stem cells, J. Transl. Med. 5:55, Springer Nature, Germany (2007).
Aust, L., et al., "Yield of human adipose-derived adult stem cells from liposuction aspirates," Cytotherapy. 6:7-14, Elsevier, Netherlands (Jan. 2004).
Awad, H.A., et al., "Chondrogenic differentiation of adipose-derived adult stem cells in agarose, alginate, and gelatin scaffolds," Biomaterials. 25(16):3211-3222, Elsevier, Netherlands (Jul. 2004).
Barry, F.P., et al., "Mesenchymal stem cells: clinical applications and biological characterization," Int. J. Biochem. Cell Biol. 36(4):568-584, Elsevier, Netherlands (Apr. 2004).
Beresford, J.N., et al., "Evidence for an inverse relationship between the differentiation of adipocytic and osteogenic cells in rat marrow stromal cell cultures," J. Cell. Sci. 102:341-351, The Company of Biologists, United Kingdom (1992).
Borowski, D.W., et al., "Adipose Tissue-Derived Regenerative Cell-Enhanced Lipofilling for Treatment of Cryptoglandular Fistulae-in-Ano: The ALFA Technique," Surg. Innov. 22(6):593-600, SAGE Publications, United States (2015).
Brady, A.P., et al., "Closure of a Duodenal Fistula with Fibrin Sealant," J. Vasc. Interv. Radiol. 4(4):525-529, Elsevier, Netherlands (1993).
Cai, X., et al., "Adipose stem cells originate from perivascular cells," Biol. Cell. 103(9):435-447, Rockefeller University Press, United States (2011).
Cao, Y., et al., "Human adipose tissue-derived stem cells differentiate into endothelial cells in vitro and improve postnatal neovascularization in vivo," Biochem. Biophys. Res. Commun. 332(2): 370-379, Elsevier, Netherlands (Jul. 2005).
Caplan, A.I., "Review: mesenchymal stem cells: cell-based reconstructive therapy in orthopedics," Tissue Eng. 11(7-8):1198-1211, Mary Ann Liebert, Inc., United States (Jul. 2005).
Caplan, A.I., et al., "Mesenchymal stem cells: building blocks for molecular medicine in the 21st century," Trends Mol. Med. 7(6):259-264, Cell Press, United States (2001).
Caplan, A.I., "Mesenchymal Stem Cells," J. Orthop. Res. 9(5):641-650, Wiley, United States (1991).
BD BioSciences, "Human and Mouse CD Marker Handbook," accessed at file:///C:/Users/elynch/Downloads/DS_Human-Mouse-CD-Maker-Biosciences_CT_DE.pdf, 48 pages (2010).
Chandra, V., et al., "Generation of pancreatic hormone-expressing islet-like cell aggregates from murine adipose tissue-derived stem cells," Stem Cells. 27:1941-1953, Oxford University Press, United Kingdom (2009).
Cho, Y.B., et al., "Long-Term Results of Adipose-Derived Stem Cell Therapy for the Treatment of Crohn's Fistula," Stem Cells Transl. Med. 4(5):532-537, Oxford University Press, United Kingdom (2015).
GenBank, "COL2A1 collagen type II alpha 1 chain [ *Homo sapiens* (human) ]," Gene ID No. 1280, accessed at http://www.ncbi.nlm.nih.gov/gene/1280, accessed on Feb. 24, 2011, 14 pages.
Cowan, C.M., et al., "Adipose-derived adult stromal cells heal critical-size mouse calvarial defects," Nat. Biotechnol. 22(5):560-567, Nature Portfolio, Germany (May 2004).
Crisan, M., et al., "A Perivascular Origin for Mesenchymal Stem Cells in Multiple Human Organs," Cell Stem Cell 3(3):301-313, Cell Press, United States (2008).
Portilla, F., et al., "Expanded allogeneic adipose-derived stem cells (eASCs) for the treatment of complex perianal fistula in Crohn's disease: results from a multicenter phase I/IIa clinical trial," Int. J. Colorectal Dis. 28(3):313-23, Springer, Germany (2013).
De Ugarte, D.A., et al., "Comparison of Multi-Lineage Cells from Human Adipose Tissue and Bone Marrow," Cell Tissues Organs 174:101-109, Karger Publishers, Switzerland (2003).
Declaration by Dr. Mario Delgado dated Mar. 26, 2011, submitted in U.S. Appl. No. 95/001,592, 27 pages.
Declaration by Dr. Mario Delgado, dated Sep. 30, 2011, submitted in U.S. Appl. No. 95/001,592, 27 pages.
Declaration of Farshid Guilak, Pursuant to 37 CFR § 1.132, dated Aug. 31, 2011, 19 pages.
"Durham firm sells technology, shuts down; Md. fund's startup to develop Artecel's stem cell science", LexisNexis, The Herald-Sun (Durham, NC), Apr. 11, 2003.
Entenmann, G., et al., "Relationship between replication and differentiation in cultured human adipocyte precursor cells," Am. J. Physiol. 270(4 Pt 1):C1011-6, American Physiological Society, United States (1996).
Estes, B.T., et al., "Monolayer Cell Expansion Conditions Affect the Chondrogenic Potential of Adipose Derived Stem Cells," Biotechnol. Bioeng. 99(4):986-995, Wiley, United States (2008).
Office Action mailed on Oct. 26, 2011, in U.S. Appl. No. 11/167,061, Miguel, M.J., et al., filed Jun. 24, 2005, 8 pages.
Final Rejection mailed on Jan. 16, 2018, in U.S. Appl. No. 15/581,777, Buscher, D., et al., filed Apr. 28, 2017, 15 pages.
Koc, O.N., et al., "Mesenchymal stem cells: heading into the clinic," Bone Marrow Transplant. 27:35-239, Nature Portfolio, Germany (2001).
Duran, N.E., et al., "Stem cell-based therapies in inflammatory bowel disease: promises and pitfalls," Therap. Adv. Gastroenterol. 9(4):533-547, Sage Publications, United States (2016).
Salem, G.A., et al., "Stem cell transplant in inflammatory bowel disease: a promising modality of treatment for a complicated disease course," Stem Cell Investig. 4:95, AME Publishing Company, Hong Kong (2017).
Muraglia, A., et al., "Clonal mesenchymal progenitors from human bone marrow differentiate in vitro according to a hierarchical model," J. Cell Sci. 113:1161-1166, Company of Biologists Ltd, United Kingdom (2000).

(56) References Cited

OTHER PUBLICATIONS

European Medicines Agency, "Reflection paper on stem cell-based medicinal products," accessed at https://www.ema.europa.eu/en/documents/scientific-guideline/reflection-paper-stem-cell-based-medicinal-products_en.pdf, accessed 2011, 14 pages.
Deans, R.J., et al., "Mesenchymal stem cells: Biology and potential clinical uses," Exp. Hematol. 28(8):875-884, Elsevier, Netherlands (2000).
Office Action, mailed on Aug. 14, 2018, in U.S. Appl. No. 15/581,777, Buscher, D., et al., filed Apr. 28, 2017, 13 pages.
Leblanc, K., et al., "Treatment of severe acute graft-versus-host disease with third party haploidentical mesenchymal stem cells," Lancet 363(9419):1439-1441, Elsevier, Netherlands (May 2004).
Keating, A., "Mesenchymal stromal cells," Curr. Opin. Hematol. 13(6):419-425, Lippincott Williams and Wilkins Ltd., United States (2006).
NHS, "Complications: Crohn's Disease," NHS.uk, accessed on http://www.nhs.uk/Conditions/Crohns-disease/Pages/Complications.aspx, accessed on Mar. 8, 2017, 2 pages (cited in opposition in Europe, EP1926813).
NHS, "Symptoms: Crohn's Disease," NHS.uk, accessed at https://www.nhs.uk/conditions/crohns-disease/symptoms/, accessed on Mar. 8, 2017, 2 pages (cited in opposition in Europe, EP1926813).
Delarosa, O., et al., "Requirement of IFN-gamma-mediated indoleamine 2,3-dioxygenase expression in the modulation of lymphocyte proliferation by human adipose-derived stem cells," Tissue Eng. Part A. 15(10):2795-2806, Mary Ann Liebert, Inc., United States (2009).
Mayo Clinic, "Inflammatory Bowel Disease (IBD)," accessed at https://www.mayoclinic.org/diseases-conditions/inflammatory-bowel-disease/symptoms-causes/syc-20353315, accessed 2017, 2 pages.
Lowry, P.W., et al., "Combination therapy with oral tacrolimus (FK506) and azathioprine or 6-mercaptopurine for treatment-refractory Crohn's disease perianal fistulae," Inflamm. Bowel Dis. 5(4):239-245, Oxford University Press, United Kingdom (1999).
Rizzello, F., et al., Review article: the management of refractory Crohn's disease. Aliment. Pharmacol. Ther. 16(Suppl.4):40-47, Wiley-Blackwell, United States (2002).
TiGenix Press Release in 2013, "TiGenix Press Release," accessed at http://www.tigenix.com/en/pages/11/2013, 2 pages.
National Institute for Health Research, "Cx601 (Alofisel) for complex perianal fistula in adults with non-active or mildly-active luminal Chron's disease—second line," National Institute for Health Research Horizon Scanning Centre, 8 pages (2015).
TiGenix Press Release on Aug. 23, 2015, "TiGenix announces Cx601 meets primary endpoint in pivotal Phase III trial," GlobalNewsWire.com, accessed at https://www.globenewswire.com/news-release/2015/08/23/762658/10146900/en/TiGenix-announces-Cx601-meets-primary-endpoint-in-pivotal-Phase-III-trial.html, 4 pages.
TiGenix Press Release in 2016, "TiGenix announces positive 52-week Phase III results of Cx601 in complex perianal fistulas in Crohn's disease patients," FierceBiotech.com, accessed at https://www.fiercebiotech.com/biotech/tigenix-announces-positive-52-week-phase-iii-results-of-cx601-complex-perianal-fistulas, 3 pages.
TiGenix Press Release on Jul. 26, 2013, "TiGenix Completes EUR 6.5 million Capital Increase," GlobalNewsWire.com, accessed at https://www.globenewswire.com/en/news-release/2013/07/26/1590892/0/en/TiGenix-Completes-EUR-6-5-million-Capital-Increase.html, 2 pages.
TiGenix Press Release on Apr. 22, 2013, "TiGenix Reports Positive Phase IIa Study Results in Refractory Rheumatoid Arthritis with Allogeneic Stem Cell Product Cx611," BioSpace.com, accessed at https://www.biospace.com/article/releases/tigenix-positive-phase-iia-study-results-in-refractory-rheumatoid-arthritis-with-allogeneic-stem-cell-product-cx611-/, 3 pages.
TiGenix Press Release, 2013, "Cx611 in RA", accessed at http://www.tigenix.com/en/download/?s=rNXU81vo7ZUjEybwArESBX4S%2BkEKDIBvQYuoUTu%2FQzzXtBQzMA17TEC318DkwthFj%2BYyaSGvZW9cSU6K10OQDQ%3D%3D, 47 pages.
Author unknown, published by Datapharm, "Alofisel 5 million cells/ml suspension for injection—Summary of Product Characteristics," Medicines.org.uk, accessed at https://www.medicines.org.uk/emc/product/9231/smpc/history#gref, accessed on May 23, 2019, 2 pages.
Be The Match, "Haploidentical Transplant," BeTheMatch.com, accessed at https://bethematch.org/patients-and-families/about-transplant/what-is-a-bone-marrow-transplant/haploidentical-transplant/, 3 pages, retrieved from the internet, Feb. 14, 2019.
Bochev, I., et al., "Mesenchymal stem cells from human bone marrow or adipose tissue differently modulate mitogen-stimulated B-cell immunoglobulin production in vitro," Cell Biol. Int. 32(4):384-393, Portland Press, United Kingdom (2008).
Bouffi, C., et al., "Multipotent mesenchymal stromal cells and rheumatoid arthritis: risk or benefit?" Rheumatology 48(10):1185-1189, Oxford University Press, United Kingdom (2009).
Bourin, P., et al., "Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT))," Cytotherapy. 15(6):641-648, Elsevier, Netherlands (2013).
Byk, T., et al., "Lipofectamine and Related Cationic Lipids Strongly Improve Adenoviral Infection Efficiency of Primitive Human Hematopoietic Cells," Hum. Gene Ther. 9(17):2493-2502, Mary Ann Liebert, Inc., United States (1998).
"Cx611-0101, eASCs intravenous administration to refractory rheumatoid arthritis patients," ClinicalTrials.gov, U.S. National Library of Medicine, Aug. 13, 2012, accessed at https://clinicaltrials.gov/ct2/show/NCT01663116, 10 pages.
Delarosa, O., et al., "Mesenchymal Stem Cells as Therapeutic Agents of Inflammatory and Autoimmune Diseases," Curr. Opin. Biotechnol. 23(6):978-983, Elsevier, Netherlands (2012).
Deng, W., et al., "Allogeneic bone marrow-derived flk-1+Sca-1-mesenchymal stem cells leads to stable mixed chimerism and donor-specific tolerance," Exp. Hematol. 32(9):861-867, Elsevier, Netherlands (Sep. 2004).
European Medicine's Agency Press Release in 2017, "New medicine to treat perianal fistulas in patients with Crohn's disease," accessed at https://www.ema.europa.eu/en/news/new-medicine-treat-perianal-fistulas-patients-crohns-disease, 2 pages.
Office Action mailed on Mar. 6, 2017, in U.S. Appl. No. 14/017,152, Miguel, M.G., et al., filed Sep. 3, 2013, 12 pages.
Office Action mailed on Oct. 7, 2015, in U.S. Appl. No. 14/017,152, Miguel, M.G., et al., filed Sep. 3, 2013, 7 pages.
Fouillard, L., et al., "Engraftment of allogeneic mesenchymal stem cells in the bone marrow of a patient with severe idiopathic aplastic anemia improves stroma," Leukemia 17(2):474-476, Nature Portfolio, Germany (Feb. 2003).
Garcia-Olmo, D., et al., "Expanded adipose-derived stem cells for the treatment of complex perianal fistula: a phase II clinical trial," Dis. Colon. Rectum. 52:79-86, Lippincott Williams & Wilkins, United States (2009).
Gonzalez, M.A., et al., "Treatment of Experimental Arthritis by Inducing Immune Tolerance With Human Adipose-Derived Mesenchymal Stem Cells," Arthritis. Rheum. 60(4):1006-1019, Wiley, United States (2009).
Gonzalez-Rey, E., et al., "Human Adipose-derived Mesenchymal Stem Cells reduce Inflammatory and T Cell Responses and Induce Regulatory T Cells in Vitro in Rheumatoid Arthritis," Ann. Rheum. Dis. 69:241-248, BMJ, United Kingdom (2010).
Guadalajara, H., et al., "Prospect of Cell Therapy for Treating Perianal Fistula, Including Crohn's Disease," Int. J. Stem Cell Res. Ther. 3(1):28, ClinMed International Library, United States (2016).
Hall, S.R., et al., "Mesenchymal stromal cells improve survival during sepsis in the absence of heme oxygenase-1: the importance of neutrophils," Stem Cells 31(2):397-407, Wiley, United States (2013).
Ichim, T.E., et al., "Autologous Stromal Vascular Fraction Cells: A Tool for Facilitating Tolerance in Rheumatic Disease," Cell. Immunol. 264:7-17, Elsevier, Netherlands (2010).
Ivanova-Todorova, E., et al., "Adipose tissue-derived mesenchymal stem cells are more potent suppressors of dendritic cells differentiation compared to bone marrow-derived mesenchymal stem cells." Immunol. Lett. 126:37-42, Elsevier, Netherlands (2009).

(56) References Cited

OTHER PUBLICATIONS

Japanese Pre-Trial Report, Dec. 9, 2015.
Kan, I., et al., "Integral Therapeutic Potential of Bone Marrow Mesenchymal Stem Cells," Cur. Drug Targets 6:31-41, Bentham Science Publishers B.V., United Arab Emirates (Feb. 2005).
Kebriaei, P., et al., "Adult Human Mesenchymal Stem Cells Added to Corticosteroid Therapy for the Treatment of Acute Graft-versus-Host Disease," Biol. Blood Marrow Transplant. 15: 804-811, Elsevier, Netherlands (2009).
Kim, J.H., et al., "Paradoxical Effects of Human Adipose Tissue-Derived Mesenchymal Stem Cells on Progression of Experimental Arthritis in SKG Mice," Cell. Immunol. 292:94-101, Elsevier, Netherlands (2014).
Kim, J.M., et al., "Systemic transplantation of human adipose stem cells attenuated cerebral inflammation and degeneration in a hemorrhagic stroke model," Brain Res. 1183:43-50, Elsevier, Netherlands (2007).
Kotobuki, N., et al., "Cultured Autologous Human Cells for Hard Tissue Regeneration: Preparation and Characterization of Mesenchymal Stem Cells from Bone Marrow," Artif. Organs 28(1):33-39, Wiley, United States (Jan. 2004).
Krasnodembskaya, A., et al., "Antibacterial Effect of Human Mesenchymal Stem Cells is Mediated in Part from Secretion of the Antimicrobial Peptide LL-37", Stem Cells. 28(12):2229-2238, Wiley, United States (2010).
Kurozumi, K., et al., "BDNF Gene-Modified Mesenchymal Stem Cell Promote Functional Recovery and Reduce Infarct Size in the Rat Middle Cerebral Artery Occlusion Model," Molecular Therapy, 9(2):189-197 (Feb. 2004).
Kuruvilla, A.P., et al.; "Protective effect of transforming growth factor Betal on experimental autoimmune diseases in mice," Proc. Natl. Acad. Sci. 88(7): 2918-2921, National Academy of Sciences, United States (1991).
Leblanc, K., et al., "Immunomodulation by mesenchymal stem cells and clinical experience," J. Intern. Med. 262:509-525, Wiley, United States (2007).
Lee, J.W., et al., "Therapeutic Effects of Human Mesenchymal Stem Cells in Ex Vivo Human Lungs Injured with Live Bacteria," Am. J. Resp. Crit. Care Med. 187(7):751-760, American Thoracic Society, United States (2013).
Lee, H.K., et al., "Preclinical Efficacy and Mechanisms of Mesenchymal Stem Cells in Animal Models of Autoimmune Diseases," Immune Netw. 14(2):81-88, Korean Association of Immunologists, Korea (2014).
Li, J., et al., "Human umbilical cord mesenchymal stem cells reduce systemic inflammation and attenuate LPS-induced acute lung injury in rats," J. Inflamm. 9(1):33, Dove Medical Press, United Kingdom (2012).
Lopez-Santalla, M., et al., "Human Adipose-Derived Mesenchymal Stem Cells Modulate Experimental Autoimmune Arthritis by Modifying Early Adaptive T Cell Responses," Stem Cells 33:3493-3503, Wiley, United States (2015).
Maneesh "Nonmyeloablastive Stem Cell Therapy for Perianal Fistulizing Crohn's Disease: A Systematic Review of Safety and Efficacy," Gastroenterology, 2 pages (2014).
Mccarter, S.D., et al., "Cell-based Angiopoietin-1 Gene Therapy for Acute Lung Injury," Am. J. Respir. Crit. Care Med. 175(10):1014-1026, American Thoracic Society, United States (2007).
Mei, S.H.J., et al., "Prevention of LPS-induced Acute Lung Injury in Mice by Mesenchymal Stem cells Overexpressing Angiopoietin 1," PLoS Med. 4(9):1525-1537, PLOS, United States (2007).
Mei, S.H.J., et al., "Mesenchymal Stem Cells Reduce Inflammation while Enhancing Bacterial Clearance and Improving Survival in Sepsis," Am. J. Respir. Crit. Care Med. 182(8):1047-1057, American Thoracic Society, United States (2010).
Mitchell, J.B., et al., "Immunophenotype of Human Adipose-Derived Cells: Temporal Changes in Stromal-Associated and Stem Cell-Associated Markers," Stem Cells. 24(2):376-385, Wiley, United States (2006).

Molendijk, I., et al., "Allogeneic Bone Marrow—Derived Mesenchymal Stromal Cells Promote Healing of Refractory Perianal Fistulas in Patients With Crohn's Disease," Gastroenterology 149(4):918-927, Elsevier, Netherlands (2015).
Nemeth, K., et al., "Bone Marrow Stromal Cells Attenuate Sepsis via Prostaglandin E(2)-Dependent Reprogramming of Host Macrophages to increase their interleukin-10 Production," Nat. Med. 15(1):42-49, Nature Portfolio, Germany (2009).
Office Action mailed on May 14, 2015, in U.S. Appl. No. 14/017,152, Miguel, M.G., et al., filed Sep. 3, 2013, 7 pages.
Office Action mailed on Aug. 12, 2014, in U.S. Appl. No. 14/017,152, Miguel, M.G., et al., filed Sep. 3, 2013, 9 pages.
Office Action mailed Jun. 23, 2016, in U.S. Appl. No. 14/017,152, Miguel, M.G., et al., filed Sep. 3, 2013, 14 pages.
Panes, J., et al., "A phase III randomized controlled trial of Cx601, expanded allogeneic adipose-derived mesenchymal stem cells (eASC), for complex perianal fistulas in Crohn's disease," Journal of Crohn's and Colitis, Oral presentations, pp. S1 (2016).
Panes, J., et al., "CX601, Allogeneic Expanded Adipose-derived Mesenchymal Stem Cells (EASC), for Complex Perianal Fistulas in Crohn's Disease: Long-term Results from a Phase III Randomized Controlled Trial," AGA Abstracts, pp. 187 (2017).
Park, K.J., et al al., "Adipose-Derived Stem Cell Treatment for Persistent Perinea! Wound in Complex Crohn's Perianal Abscess/Fistula," Gastroenterology 142(5): S1, pp. 76, AGA Abstract 329 (2012).
Park, K.J., et al., "Allogeneic Adipose-Derived Stem Cells for the Treatment of Crohn's Perianal Fistula: a Phase I/IIa Clinical Study," Gastroenterology 146(5):1016, Abstract 507 (2014).
Park, K.J., et al., "Allogeneic adipose-derived stem cells for the treatment of perianal fistula in Crohn's disease: a pilot clinical trial," Colorectal Dis. 18(5):468-76, Wiley, United States (2015).
Rizk, M., et al., "Heterogeneity in Studies of Mesenchymal Stromal Cells to Treat or Prevent Graft-versus-Host Disease: A Scoping Review of the Evidence, " Biol. Blood Marrow Trans. 22(8):1416-1423, Elsevier, Netherlands (2016).
Roach, M.L., et al., "Methods for the Isolation and Maintenance of Murine Embryonic Stem Cells," Methods Mol. Biol. 185:1-16, Humana Press, United States (2002).
Rodriguez, J.P., et al., "Autologous Stromal Vascular Fraction Therapy for Rheumatoid Arthritis: Rationale and Clinical Safety", Int. Arch. Med. 5(5):1-9, BioMed Central, United Kingdom (2012).
Schaffler, A., et al., "Concise Review: Adipose Tissue-derived Stromal Cells—Basic and Clinical Implications for Novel Cell-based Therapies," Stem Cells 25(4):818-827, Wiley, United States (2007).
European Search Report received for EP Application No. EP18152520, European Patent Office, Netherlands, mailed on May 17, 2018, 11 pages.
Singer, N.G., et al., "Mesenchymal stem cells: mechanisms of inflammation," Annu. Rev. Pathol. 6:457-78, Annual Reviews, United States (2011).
Tholpady, S.S., et al., "Adipose Tissue: Stem Cells and Beyond," Clin. Plast. Surg. 33:55-62, Elsevier, Netherlands (2006).
Tigenix, "Tigenix Living Medicines, Corporate Presentation, Feb. 2015," 40 pages (2015).
Tigenix, "Tigenix Living Medicines, Corporate Presentation, Mar. 2015," 39 pages (2015).
Tigenix, "Tigenix Living Medicines, Corporate Presentation, Oct. 2015," 40 pages (2015).
Tigenix, "Tigenix Living Medicines, Corporate Presentation, Sep. 2015," 41 pages (2015).
Tigenix, "Tigenix Living Medicines, Corporate Presentation, Jan. 2016," 39 pages (2016).
Tigenix, "Cx601 Crohn's disease and perianal fistulas," Retrieved from http://tigenix.com/en/page/14/cx601, 5 pages (2016).
Walmsley, G.G., et al., "High-Throughput Screening of Surface Marker Expression on Undifferentiated and Differentiated Human Adipose-Derived Stromal Cells," Tissue Eng. Part A. 21(15-16):2281-91, Mary Ann Liebert, Inc., United States (2015).
Xu, J., et al., "Prevention of endotoxin-induced systemic response by bone marrow-derived mesenchymal stem cells in mice," Am. J.

(56) References Cited

OTHER PUBLICATIONS

Physiol. Lung. Cell Mol. Physiol. 293(1):L131-L141, American Physiological Society, United States (2007).
Yanez, R., et al.; "Adipose Tissue-Derived Mesenchymal Stem Cells Have In Vivo immunosuppressive Properties Applicable for the Control of the Graft-Versus-Host Disease," Stem Cells. 24(11):2582-2591, Wiley, United States (2006).
Zhang, F.J., et al., "Preservation media, durations and cell concentrations of short-term storage affect key features of human adipose-derived mesenchymal stem cells for therapeutic application," Peerj. 5:e3301, O'Reilly Media, United States (2017).
Algeri, M., et al., "Mesenchyrnal stromal cells and chronic inflammatory bowel disease," Immunol. Letters 168(2):191-200, Elsevier, Netherlands (2015).
Dominici, M., et al., "Minimal criteria for defining multipotent mesenchymal stromal cells," Cytotherapy. 8(4):315-317, Elsevier, Netherlands (2006).
Duijvestein, M., et al., "Autologous bone marrow-derived mesenchymal stromal cell treatment for refractory luminal Crohn's disease: results of a phase I study," Gut 59:1662-1669, BMJ, United Kingdom (2010).
Galipeau, J., "The mesenchymal stromal cells dilemma—does a negative phase III trial of random donor mesenchymal stromal cells in steroid-resistant graft-versus-host disease represent a death knell or a bump in the road?" Cytotherapy. 15(1):2-8, Elsevier, Netherlands (2013).
Australian Government Department of Health, "Australian Public Assessment Report for Remestemcel-L, ex vivo adult human mesenchymal stem cells," Australian Government, Department of Health—Therapeutic Goods Administration, accessed at https://www.tga.gov.au/sites/default/files/auspar-remestemcel-1-150315.pdf, 74 pages (2015).
Gotherstrom, C., et al., "Immunologic properties of human fetal mesenchymal stem cells," Am. J. Obstet. Gynecol. 190:239-45, Elsevier, Netherlands (Jan. 2004).
Petrenko et al., "Stem Cells off Adipose Tissue," Biotechnology 1(4):39-48, Institute of Cryobiology and Cryomedicine, Problems of the National Academy of Sciences of Ukraine, Ukraine (2008).
Polchert, D., et al., "IFN-gamma activation of mesenchymal stem cells for treatment and prevention of graft versus host disease," Eur. J. Immunol. 38:1745-1755, Wiley-VCH, Germany (2008).
Sugiura, F., et al., "Osteogenic potential of rat mesenchymal stem cells after several passages," Biochem. Biophys. Res. Comm. 316(1):233-239, Elsevier, Netherlands (Mar. 2004).
Uchida, K., et al., "Comparison of the cytokine-induced migratory response between primary and subcultured populations of rat mesenchymal bone marrow cells," J. Orthop. Sci. 12(5):484-492, Springer Science+Business Media, Germany (2007).
Gonzalez-Rey, E., et al., "Human adult stem cells derived from adipose tissue protect against experimental colitis and sepsis," Gut 58:929-939, BMJ, United Kingdom (2009).
Krasnodembskaya, A., et al., "Human mesenchymal stem cells reduce mortality and bacteremia in gram-negative sepsis in mice in part by enhancing the phagocytic activity of blood monocytes," Am. J. Physiol. Lung Cell Mol. Physiol. 302:L1003-L1013, American Physiological Society, United States (2012).
Pedrazza, L., et al., "Mesenchymal stem cells decrease splenocytes apoptosis in a sepsis experimental model," Inflamm. Res. 63:719-728, Springer Science+Business Media, Germany (2014).
Christman, K.L., et al., "Injectable fibrin scaffold improves cell transplant survival, reduces infarct expansion, and induces neovasculature formation in ischemic myocardium," J. Am. Coll. Cardiol. 44(3):654-60, American College of Cardiology, United States (Aug. 2004).
Mancheno-Corvo, P., et al., "T Lymphocyte Prestimulation Impairs in a Time-Dependent Manner the Capacity of Adipose Mesenchymal Stem Cells to Inhibit Proliferation: Role of Interferon γ, Poly I:C, and Tryptophan Metabolism in Restoring Adipose Mesenchymal Stem Cell Inhibitory Effect," Stem Cells Dev. 24(18):2158-2170, Mary Ann Liebert, Inc., United States (2015).
Menta, R., et al., "Tryptophan concentration is the main mediator of the capacity of adipose mesenchymal stromal cells to inhibit T-lymphocyte proliferation in vitro," Cytotherapy. 16:1679-1691, Elsevier, Netherlands (2014).
Sebastiao, M.J., et al., "Human cardiac stem cells inhibit lymphocyte proliferation through paracrine mechanisms that correlate with indoleamine 2, 3-dioxygenase induction and activity," Stem Cell Res. Ther. 9:290, Elsevier, Netherlands (2018).
Pittenger, M.F., et al., "Mesenchymal Stem Cells and Their Potential as Cardiac Therapeutics," Circ. Res. 95:9-20, Lippincott Williams & Wilkins, United States (Jul. 2004).
Thitilertdecha, P., et al., "Extensive Characterization of Mesenchymal Stem Cell Marker Expression on Freshly Isolated and In Vitro Expanded Human Adipose-Derived Stem Cells from Breast Cancer Patients," Stem Cells Int. 2020:8237197, Wiley, United States (2020).
Wang, H., et al., "The complex and central role of interferon-gamma in graft-versus-host disease and graft-versus-tumor activity," Immunol. Rev. 258(1):30-44, Wiley, United States (2014).
Garcia Olmo, D., "Expanded adipose-derived stem cells (Cx401) for the treatment of complex perianal fistula, a phase II clinical trial," Gastroenterology 132(4), 2 pages, American Gastroenterological Association, United States (2007).

* cited by examiner

3A

3B

*p<0.001 versus controls

*p<0.001 versus controls

* $p<0.01$ versus controls

CELL POPULATIONS HAVING IMMUNOREGULATORY ACTIVITY, METHOD FOR ISOLATION AND USES

CROSS-REFERENCE RELATED APPLICATIONS

This application is a continuation of U.S. patent application Ser. No. 15/581,801, filed Apr. 28, 2017, which application is a continuation of U.S. patent application Ser. No. 14/464,147, filed Aug. 20, 2014, now issued as U.S. Pat. No. 9,943,550, which application is a divisional of U.S. patent application Ser. No. 12/067,708, abandoned, which application is a 35 U.S.C. § 371 National Phase Application of PCT/EP2006/009244, filed Sep. 22, 2006, which applications are each incorporated by reference herein in their entireties.

FIELD OF THE INVENTION

The present invention relates to the prevention, treatment or amelioration of one or more symptoms of disorders in which modulation of a subject's immune system is beneficial utilizing cell populations derived from adult t issues. In particular, the present invention provides a population of connective tissue derived cells that respond to interferon-gamma (IFN-γ) by expressing indolamine-2,3-dioxygenase (IDO) for use in preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues.

BACKGROUND OF THE INVENTION

The immune system in higher vertebrates represents the first line of defence against various antigens that can enter the vertebrate body, including micro-organisms such as bacteria, fungi and viruses that are the causative agents of a variety of diseases. Moreover, the immune system is also involved in a variety of other diseases or disorders, including autoimmune or immunopathologic diseases, immunodeficiency syndromes, atherosclerosis and various neoplastic diseases. Although methods are available for treating these diseases, many current therapies provide less than adequate results. Among new emergent therapeutic strategies, those based on cell therapy appear to constitute a potentially useful tool for treating a great number of diseases. Thus, a great effort is being currently made by researchers in order to achieve said aim.

Autoimmune Diseases

Autoimmune diseases are caused when the body's immune system, which is meant to defend the body against bacteria, viruses, and any other foreign product, malfunctions and produces a pathological response against healthy tissue, cells and organs. Antibodies, T cells and macrophages provide beneficial protection, but can also produce harmful or deadly immunological responses.

Autoimmune diseases can be organ specific or systemic and are provoked by different pathogenic mechanisms. Organ specific autoimmunization is characterized by aberrant expression of major-histocompatibility complex (MHC) antigens, antigenic mimicry and allelic variations in MHC genes. Systemic autoimmune diseases involve polyclonal B cell activation and abnormalities of immunoregulatory T cells, T cell receptors and MHC genes. Examples of organ specific autoimmune diseases are diabetes, hyperthyroidism, autoimmune adrenal insufficiency, pure red cell anemia, multiple sclerosis and rheumatic carditis. Representative systemic autoimmune diseases are systemic lupus erythematosus, chronic inflammation, Sjogren's syndrome, polymyositis, dermatomyositis and scleroderma.

Current treatment of autoimmune diseases involves administering immunosuppressive agents such as cortisone, aspirin derivatives, hydroxychloroquine, methotrexate, azathioprine and cyclophosphamide or combinations thereof. The dilemma faced when administering immunosuppressive agents, however, is the more effectively the autoimmune disease is treated, the more defenseless the patient is left to attack from infections, and also the more susceptible for developing tumours. Thus, there is a great need for new therapies for the treatment of autoimmune diseases.

Inflammatory Disorders

Inflammation is a process by which the body's white blood cells and secreted factors protect our bodies from infection by foreign substances, such as bacteria and viruses. Secreted factors known as cytokines and prostaglandins control this process, and are released in an ordered and self-limiting cascade into the blood or affected tissues.

Inflammatory Bowel Disease (JED)

IBD is a family of chronic, idiopathic, relapsing, and tissue-destructive diseases characterized by dysfunction of mucosal T cells, altered cytokine production and cellular inflammation that ultimately leads to damage of the distal small intestine and the colonic mucosa. IBD is clinically subdivided into two phenotypes: Crohn's disease (CD) and ulcerative colitis. CD is a nowadays incurable autoimmune disease with a prevalence of 0.05% that leads to chronic inflammation resulting in a range of gastrointestinal and extraintestinal symptoms, including abdominal pain, rectal bleeding, diarrhea, weight loss, skin and eye disorders, and delayed growth and sexual maturation in children. These symptoms can greatly impact the patients' well being, quality of life, and capacity of function. Because CD is chronic and typically has an onset before 30 years of age, patients generally require lifelong treatment. Although its etiology remains unknown, there is circumstantial evidence to link CD to a failure of the mucosal immune system to attenuate the immune response to endogenous antigens.

Therapeutic agents currently used for CD, including aminosalicylates, corticosteroids, azathioprine, 6-mercaptopurine, antibiotics, and methotrexate, are not entirely effective, nonspecific, and with multiple adverse side effects. In most cases, surgical resection is the ultimate alternative. Therefore, the present therapeutic strategy is to find drugs or agents that specifically modulate both components of the disease, i.e., the inflammatory and T-cells driven responses.

Recently, the drug infliximab has been approved for the treatment of moderate to severe Crohn's disease that does not respond to standard therapies and for the treatment of open, draining fistulas. Infliximab, the first treatment approved specifically for Crohn's disease, is an anti-tumour necrosis factor (TNF) antibody. TNF is a protein produced by the immune system that may cause the inflammation associated with Crohn's disease. Anti-TNF removes TNF from the bloodstream before it reaches the intestines, thereby preventing inflammation. However, since it has a systemic effect, and TNF is a very pleiotropic factor, severe side effects are relatively common, and its long-term safety is still to be determined. Also, the efficacy is also limited because many of the inflammatory processes that occur in the patients are not dependent on TNF signalling.

Rheumatoid Arthritis (RA)

Rheumatoid arthritis and juvenile rheumatoid arthritis are types of inflammatory arthritis. Arthritis is a general term that describes inflammation in joints. Some, but not all, types of arthritis are the result of misdirected inflammation. Rheumatoid arthritis affects about 1% of the world's population and is essentially disabling. Rheumatoid arthritis is an autoimmune disorder where the body's immune system improperly identifies the synovial membranes that secrete the lubricating fluid in the joints as foreign. Inflammation results, and the cartilage and tissues in and around the joints are damaged or destroyed. The body replaces damaged tissue with scar tissue, causing the normal spaces within the joints to become narrow and the bones to fuse together.

In rheumatoid arthritis, there is an autoimmune cycle of persistent antigen presentation, T-cell stimulation, cytokine secretion, synovial cell activation, and joint destruction.

Currently available therapy for arthritis focuses on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. Anti-TNF humanized monoclonal antibodies, such as Infliximab are also used; however, it has many secondary effects or side effects and its efficacy is quite low. "Second line drugs" include gold, methotrexate and steroids. Although these are well-established treatments for arthritis, very few patients remit on these lines of treatment alone, and difficult treatment issues still remain for patients with rheumatoid arthritis.

In general, the current treatments for chronic inflammatory disorders have a very limited efficiency, and many of them have a high incidence of side effects or cannot completely prevent disease progression. So far, no treatment is ideal, and there is no cure for these type of pathologies. Thus, there is a great need for new therapies for the treatment of inflammatory disorders.

Inhibition of T-Cell Responses

All immune responses are controlled by T cells. Self-reactive cells with the potential to elicit autoimmune responses comprise a part of the normal T cell repertoire, but in the healthy state, their activation is prevented by suppressor cells. Although T suppressor cells were originally described in the 1970s, significant progress in characterizing T-cell subsets has been made only recently, when they have been renamed as regulatory T cells.

There are different CD4$^+$, CD8$^+$, natural killer cell, and γδ T cell subsets with regulatory (suppressor) activity. Two major types of T-reg cells have been characterized in the CD4$^+$ population, i.e., the naturally-occurring, thymus-generated T-reg cells, and the peripherally-induced, IL-10 or TGF-β secreting T-reg cells (Tr1 cells). The CD4$^+$CD25$^+$, Foxp3-expressing, naturally-occurring T-reg cells generated in thymus, migrate and are maintained in the periphery. The signals for their thymic generation and maintenance in the periphery are not entirely defined, although both CD28 stimulation and IL-2 appear to be required. The number of CD4$^+$CD25$^+$ T-reg cells in the periphery does not decrease with age, although these cells are anergic and prone to apoptosis, and their site of origin, the thymus, undergoes age-related involution. This suggests that the pool of CD4$^+$ CD25$^+$ T-reg cells is maintained peripherally. Several experimental models support the idea of peripheral generation of CD4$^+$CD25$^+$ T-reg cells from CD4$^+$CD25$^-$ T cells. The endogenous factors and mechanisms controlling the peripheral expansion of CD4$^+$CD25$^+$ T-reg cells are mostly unknown.

There is evidence that the cytokine transforming growth factor-beta (TGF-β) plays an important role in the expansion of thymus-derived, professional CD4+ CD25+ precursors that circulate in the blood. TGF-β is also involved in the generation of peripherally induced CD4+ and CD8+ regulatory subsets.

However, recent experimental data suggest that a mechanism of immunotolerance could be dependent on tryptophan metabolism, and in particular on the activity of the enzyme indoleamine 2,3-dioxygenase (IDO), which is an intracellular heme-containing enzyme that catalyzes the initial rate-limiting step in tryptophan degradation along the kynurenine pathway.

There is considerable evidence that supports the hypothesis that cells expressing IDO can suppress T cell responses and promote tolerance (Mellor and Munn, Nat Rev Immunol. 2004 October; 4(10):762-74). IDO is expressed in some subsets of dendritic cells (DCs), which are key regulators of immune response (tolerogenic DCs). These DCs are able of suppressing in vivo T-cell responses by locally depleting tryptophan (US Patent No. 2002/0155104). Aside from monocyte-derived DCs and macrophages, several tumour lines, intestinal cells, and trophoblasts express IDO. The expression of IDO in trophoblasts appears to be constitutive and has been strongly correlated to tolerance of allogeneic tissue from the foetus. IDO is believed to induce apoptosis in T cells, and cause spontaneous tolerance to liver allografts.

The molecular mechanisms behind the immunosuppressive activity of IDO are not known. However, it has been demonstrated that DCs expressing IDO are able to induce the generation of regulatory T cells. IDO is induced in human cells by several inflammatory mediators, including interferons and lipopolysaccharide (LPS), as well as by viral infection. Several studies have shown that allogeneic tumour cells being rejected by the host immune system in vivo up-regulate IDO and this effect is mediated by IFN-γ.

Recent experiments have indicated an in vitro immunosuppressive capacity of bone marrow derived mesenchymal stem cells (MSCs) and adipose-derived stem cells (ASCs), as well as an in vivo immunosuppressive capacity of MSCs. This in vivo activity has been studied in bone marrow transplants, in which the infusion of expanded MSCs appears to reduce acute and chronic graft versus host disease (GVHD). The in vitro effect is characterized by a suppression of lymphocyte proliferation in experiments where the lymphocytes were activated either via a mixed lymphocyte reaction (MLR) or stimulation with phytohemagglutinin (PHA). However, the molecular mechanisms responsible for the immunosuppressive effects of said cells have not been unequivocally identified.

SUMMARY OF THE INVENTION

The invention is based on the discovery that certain cell populations with multilineage potential which are present in different connective tissues are capable of acting as immunoregulatory agents in vivo and in vitro. Inventors have isolated a population of connective tissue derived cells that respond to interferon-gamma (IFN-γ) by expressing indolamine-2,3-dioxygenase (IDO). The immunoregulatory effects of said cells can be used for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues.

Thus, in an aspect, the invention relates to an isolated cell population from connective tissue wherein the cells of said cell population: (i) do not express markers specific from antigen-presenting cells (APC) in other words markers specific for antigen presenting cells; (ii) do not express indolamine 2,3-dioxygenase (IDO) constitutively; (iii) express IDO upon stimulation with interferon-gamma (IFN-γ); and (iv) present capacity to be differentiated into at least two cell lineages.

In other aspect, the invention relates to a method for the isolation of said cell population. The cell population obtainable according to said method constitutes an additional aspect of this invention.

In other aspect, the invention relates to said cell population for use in the prevention, treatment or amelioration of one or more symptoms of disorders in which modulation of a subject's immune system is beneficial.

In other aspect, the invention relates to said cell population for use as medicament, or for inducing transplantation tolerance, or for treating autoimmune diseases, or for treating an inflammatory disease. In a particular embodiment, said inflammatory disease is a chronic inflammatory disease, such as, for example, Inflammatory Bowel Disease (IBD) or Rheumatoid Arthritis (RA).

In other aspect, the invention relates to the use of said cell population in the preparation of a medicament, such as a medicament for the prevention, treatment or amelioration of one or more symptoms of disorders in which modulation of a subject's immune system is beneficial, e.g., a medicament for inducing transplantation tolerance, or a medicament for treating autoimmune diseases, or a medicament for treating an inflammatory disease.

In other aspect, the invention relates to the use of said cell population in the preparation or generation of regulatory T-cells (T-reg). Said T-reg cell population as well as a method for the isolation thereof constitute further aspects of the invention.

In other aspect, the invention relates to said T-reg cell population for use as medicament, or for inducing transplantation tolerance, or for treating autoimmune diseases, or for treating an inflammatory disease.

In other aspect, the invention relates to the use of said T-reg cell population in the preparation of a medicament, such as a medicament for the prevention, treatment or amelioration of one or more symptoms of disorders in which modulation of a subject's immune system is beneficial, e.g., a medicament for inducing transplantation tolerance, or a medicament for treating autoimmune diseases, or a medicament for treating an inflammatory disease, or a medicament for treating allergies, for example, but not limited to, hypersensitivity Type IV reactions.

In other aspect, the invention relates to a method for the isolation of an irradiated cell population which comprises irradiating said cell population with a controlled source of ionizing radiation under appropriate conditions. Said irradiated cell population constitutes a further aspect of the invention.

In other aspect, the invention relates to said irradiated cell population for use as medicament, or for inducing transplantation tolerance, or for treating autoimmune diseases, or for treating an inflammatory disease.

In other aspect, the invention relates to the use of said irradiated cell population in the preparation of a medicament, such as a medicament for the prevention, treatment or amelioration of one or more symptoms of disorders in which modulation of a subject's immune system is beneficial, e.g., a medicament for inducing transplantation tolerance, or a medicament for treating autoimmune diseases, or a medicament for treating an inflammatory disease.

In other aspect, the invention relates to a method which comprises subjecting said cell population to treatment with interferon-γ (IFN-γ). Said IFN-γ-treated cell population constitutes a further aspect of the invention.

In other aspect, the invention relates to said IFN-γ-treated cell population for use as medicament, or for inducing transplantation tolerance, or for treating autoimmune diseases, or for treating an inflammatory disease.

In other aspect, the invention relates to the use of said IFN-γ-treated cell population in the preparation of a medicament, such as a medicament for the prevention, treatment or amelioration of one or more symptoms of disorders in which modulation of a subject's immune system is beneficial, e.g., a medicament for inducing transplantation tolerance, or a medicament for treating autoimmune diseases, or a medicament for treating an inflammatory disease.

In other aspect, the invention relates to a method which comprises subjecting said cell population to (i) irradiation, and (ii) stimulation with IFN-γ, wherein treatments (i) and (ii) are carried out in any order. Said irradiated IFN-γ-pre-stimulated cell population or IFN-γ-pre-stimulated irradiated cell population constitute a further aspect of the invention.

In other aspect, the invention relates to said irradiated IFN-γ-pre-stimulated cell population or IFN-γ-pre-stimulated irradiated cell population for use as medicament, or for inducing transplantation tolerance, or for treating autoimmune diseases, or for treating an inflammatory disease.

In other aspect, the invention relates to the use of said irradiated IFN-γ-pre-stimulated cell population or IFN-γ-pre-stimulated irradiated cell population in the preparation of a medicament, such as a medicament for the prevention, treatment or amelioration of one or more symptoms of disorders in which modulation of a subject's immune system is beneficial, e.g., a medicament for inducing transplantation tolerance, or a medicament for treating autoimmune diseases, or a medicament for treating an inflammatory disease.

In other aspect, the invention relates to the use of said cell population, or said T-reg cell population, or said irradiated cell population, or said IFN-γ-treated cell population, or said irradiated IFN-γ-pre-stimulated cell population, or said IFN-γ-pre-stimulated irradiated cell population for preventing, treating, or ameliorating one or more symptoms associated with autoimmune diseases, inflammatory disorders, or immunologically mediated diseases including rejection of transplanted organs and tissues.

In other aspect, the invention relates to a method of preventing, treating, or ameliorating one or more symptoms associated with autoimmune diseases, inflammatory disorders, or immunologically mediated diseases, in a subject suffering from any of said disorders or diseases, which comprises administering to said subject in need of such treatment of a prophylactically or therapeutically effective amount of said cell population, or said T-reg cell population, or said irradiated cell population, or said IFN-γ-treated cell population, or said irradiated IFN-γ-pre-stimulated cell population, or said IFN-γ-pre-stimulated irradiated cell population. The invention also relates to the use of such methods in combination therapy, in other words, a cell population of the invention is coadministered with one or more agents, either simultaneously with the second or further agent, or separately, e.g., sequentially.

In other aspect, the invention relates to a pharmaceutical composition comprising said cell population, or said T-reg cell population, or said irradiated cell population, or said IFN-γ-treated cell population, or said irradiated IFN-γ-prestimulated cell population, or said IFN-γ-pre-stimulated irradiated cell population and an acceptable pharmaceutically carrier.

In other aspect, the invention relates to a method for distinguishing adult multipotent cells from differentiated cells comprising the step of verifying whether the cell expresses IDO upon stimulation with IFN-γ.

In other aspect, the invention relates to a kit comprising said cell population, or said T-reg cell population, or said irradiated cell population, or said IFN-γ-treated cell population, or said irradiated IFN-γ-pre-stimulated cell population, or said IFN-γ-pre-stimulated irradiated cell population.

DETAILED DESCRIPTION OF THE INVENTION

Figure 1:
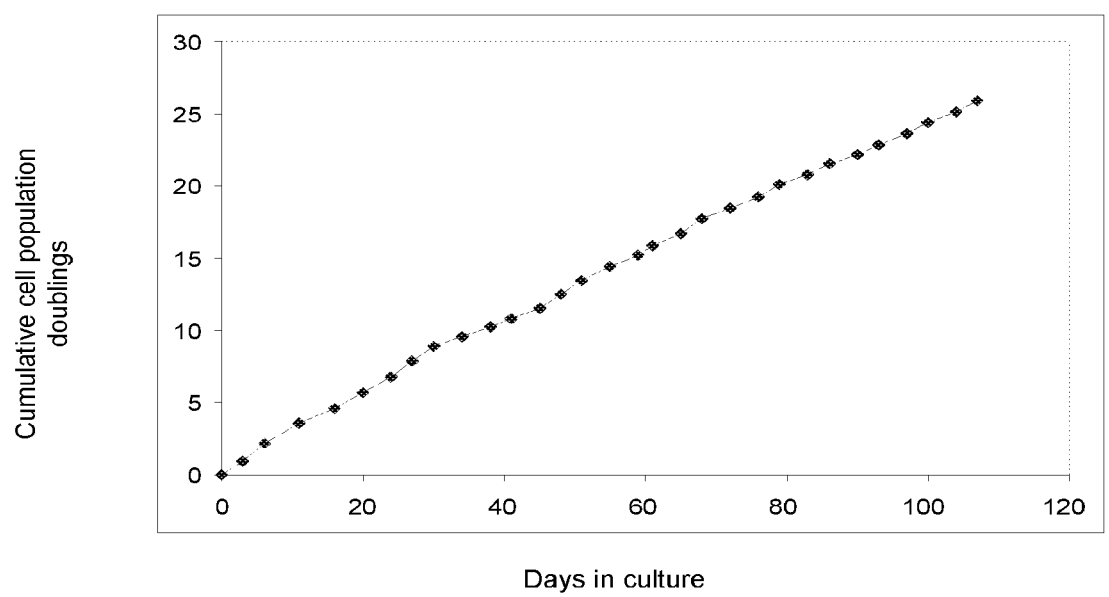
FIG. 1 shows the growth kinetics of the cells provided by the instant invention isolated from human adipose tissue and cultured ex vivo for more than 25 cell population doublings.

As it has been previously mentioned, inventors have found that certain cell populations with multilineage potential which are present in various, if not all, connective tissues and respond to interferon-gamma (IFN-γ) by expressing indolamine-2,3-dioxygenase (IDO) are capable of acting as immunoregulatory agents in vivo and in vitro. The immunosuppressant immunoregulatory effects of said cells can be used for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues.

Definitions

In order to facilitate the understanding of the present description, the meaning of some terms and expressions in the context of the invention will be explained below. Further definitions will be included along the description when necessary.

The term "antigen presenting cells" (APC) refers to a cell population that displays foreign antigen complexed with MHC (major histocompatibility complex) on its surface. Although almost every cell in the body is capable of presenting antigens to T cells, the term "antigen presenting cells" (APC) is herein limited to those specialized cells, also called professional APCs, that express HLAII in their surface, and are derived from the monocyte-macrophage lineage (for example, dendritic cells).

The term "autoimmune disease" refers to a condition in a subject characterized by cellular, tissue and/or organ injury caused by an immunologic reaction of the subject to its own cells, tissues and/or organs. Illustrative, non-limiting examples of autoimmune diseases which can be treated with the cell population of the invention include alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjögren's syndrome, Good pasture's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener's granulomatosis, etc.

The term "immunoregulatory agent" refers to an agent that inhibits or reduces one or more biological activities of the immune system. An immunoregulatory agent is an agent that inhibits or reduces one or more biological activities (e.g., the proliferation, differentiation, priming, effector function, production of cytokines or expression of antigens) of one or more immune cells (e.g., T cells).

The term "inflammatory disease" refers to a condition in a subject characterized by inflammation, e.g., chronic inflammation. Illustrative, non-limiting examples of inflammatory disorders include, but are not limited to, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g., idiopathic pulmonary fibrosis), inflammatory vaculitides (e.g., polyarteritis nodosa, Wegner's granulomatosis, Takayasu's arteritis, temporal arteritis, and lymphomatoid granulomatosis), post-traumatic vascular angioplasty (e.g., restenosis after angioplasty), undifferentiated spondyloarthropathy, undifferentiated arthropathy, arthritis, inflammatory osteolysis, chronic hepatitis, and chronic inflammation resulting from chronic viral or bacteria infections.

The term "isolated" applied to a cell population refers to a cell population, isolated from the human or animal body, which is substantially free of one or more cell populations that are associated with said cell population in vivo or in vitro.

The term "MHC" (major histocompatibility complex) refers to a subset of genes that encodes cell-surface antigen-presenting proteins. In humans, these genes are referred to as human leukocyte antigen (HLA) genes. Herein, the abbreviations MHC or HLA are used interchangeably.

The term "subject" refers to an animal, preferably a mammal including a non-primate (e.g., a cow, pig, horse, cat, dog, rat, or mouse) and a primate (e.g., a monkey, or a human). In a preferred embodiment, the subject is a human.

The term "T-cell" refers to cells of the immune system which are a subset of lymphocytes that express the T cell receptor (TCR).

The term "regulatory T-cells" (T-reg cells) refers to T cell subsets that actively suppress activation of the immune system and prevent pathological self-reactivity, i.e. an autoimmune disease.

As used herein, the terms "treat", "treatment" and "treating" refer to the amelioration of one or more symptoms associated with a disorder including, but not limited to, an inflammatory disorder, an autoimmune disease or an immunologically mediated disease including rejection of transplanted organs and tissues, that results from the administration of the cell population of the invention, the T-reg cell population of the invention, or the IFN-γ-pre-stimulated cell population of the invention, or a pharmaceutical composition comprising same, to a subject in need of said treatment.

The term "combination therapy" refers to the use of the cell populations of the present invention with other active agents or treatment modalities, in the manner of the present invention for the amelioration of one or more symptoms associated with a disorder including, but not limited to, an inflammatory disorder, an autoimmune disease or an immunologically mediated disease including rejection of transplanted organs and tissues. These other agents or treatments may include known drugs and therapies for the treatment of such disorders. The cell populations of the invention may also be combined with corticosteroids, non-steroidal anti-inflammatory compounds, or other agents useful in treating inflammation. The combined use of the agents of the present invention with these other therapies or treatment modalities may be concurrent, or given sequentially, that is, the two treatments may be divided up such that a cell population or a pharmaceutical composition comprising same of the present invention may be given prior to or after the other therapy or treatment modality. The attending physician may decide on the appropriate sequence of administering the cell population, or a pharmaceutical composition comprising same, in combination with other agents, therapy or treatment modality.

Cells of the Invention

In an aspect, the present invention relates to an isolated cell population from connective tissue, hereinafter referred to as "cell population of the invention", characterised in that the cells of said cell population:

a) do not express markers specific for antigen-presenting cells (APC),
b) do not express indoleamine 2,3-dioxygenase (IDO) constitutively, wherein constitutively is understood to mean the expression of a gene without any specific induction.
c) express IDO upon stimulation with interferon-gamma (IFN-γ) and,
d) present capacity to be differentiated into at least two cell lineages.

The cells of the cell population of the invention, hereinafter referred to as the "cells of the invention" derive from connective tissue. The term "connective tissue" refers to tissue derived from mesenchyme and includes several tissues which are characterized in that their cells are included within the extracellular matrix. Among the different types of connective tissues, adipose and cartilaginous tissues are included. In a particular embodiment, the cells of the invention are from the stromal fraction of the adipose tissue. In other particular embodiment, the cells of the invention are obtained from chondrocytes, the only cells found in the hyaline cartilage. In another particular embodiment, the cells of the invention are obtained from skin. Also, in another particular embodiment, the cells of the invention are obtained from bone marrow.

The cells of the invention can be obtained from any suitable source of connective tissue from any suitable animal, including humans. In general, said cells are obtained from non-pathological post-natal mammalian connective tissues. In a preferred embodiment, the cells of the invention are obtained from a source of connective tissue, such as the stromal fraction of adipose tissue, hyaline cartilage, bone marrow, skin etc. Also, in a particular embodiment, the cells of the cell population of the invention are from a mammal, e.g., a rodent, primate, etc., preferably, from a human.

As mentioned above, the cells of the invention are characterized in that (i) they do not express markers specific from APCs; (ii) they do not express IDO constitutively; (iii) they express IDO upon stimulation with IFN-γ; and (iv) they present capacity to be differentiated into at least two cell lineages.

Markers

The cells of the invention are negative for at least one, two, three, four or preferably all of the following markers CD11b, CD11c, CD14, CD45, and HLAII, which are specific markers for APCs lineages. Thus, the cells of the invention do not constitute a previously described subpopulation of specialized APCs.

Moreover, the cells of the invention are negative for at least one, two of, or preferably all of the following cell surface markers: CD31, CD34 and CD133.

As used herein, "negative" with respect to cell surface markers means that, in a cell population comprising the cells of the invention, less than 10%, preferably 9%, 8%, 7%, 6%, 5%, 4%, 3%, 2%, 1% or none of the cells show a signal for a specific cell surface marker in flow cytometry above the background signal, using conventional methods and apparatus (for example .a Beckman Coulter Epics XL FACS system used with commercially available antibodies and standard protocols known in the art). In a particular embodiment, the cells of the invention are characterised in that they express at least one, two, three, four, of or preferably all of the following cell surface markers: CD9, CD44, CD54, CD90 and CD105; i.e., the cells of the invention are positive for at least one, two, three, four of and preferably all said cell surface markers (CD9, CD44, CD54, CD90 and CD105). Preferably, the cells of the invention are characterised in that they have significant expression levels of at least one, two, three, four, of and preferably all of said cell surface markers (CD9, CD44, CD54, CD90 and CD105). As used herein, the expression "significant expression" means that, in a cell population comprising the cells of the invention, more than 10%, preferably 20%, 30%, 40%, 50%, 60%, 70%, 80%, 90% or all of the cells show a signal for a specific cell surface marker in flow cytometry above the background signal using conventional methods and apparatus (for example .a Beckman Coulter Epics XL FACS system used with commercially available antibodies and standard protocols known in the art). The background signal is defined as the signal intensity given by a non-specific antibody of the same isotype as the specific antibody used to detect each surface marker in conventional FACS analysis. Thus for a marker to be considered positive the specific signal observed is stronger than 10%, preferably 20%, 30%, 40%, 50%, 60%, 70%, 80%, 90%, 500%, 1000%, 5000%, 10000% or above, than the background signal intensity using conventional methods and apparatus (for example .a Beckman Coulter Epics XL FACS system used with commercially available antibodies and standard protocols known in the art).

Optionally, the cells of the invention are also negative for the cell surface marker CD106(VCAM-1). Examples of such cells are certain populations of adipose tissue-derived stromal stem cells as described herein.

Commercially available and known monoclonal antibodies against said cell-surface markers (e.g., cellular receptors and transmembrane proteins) can be used to identify the cells of the invention.

Expression of IDO

The cells of the invention do not express IDO constitutively, but they express IDO upon stimulation with IFN-γ. Experiments carried out by the inventors have shown that said cells, upon stimulation with other pro-inflammatory mediators by themselves, such us interleukin-1 (IL-1) used at a concentration of 3 ng/ml, tumour necrosis factor-alpha (TNF-α) used at a concentration of 50 ng/ml, or the endotoxin LPS used at a concentration of 100 ng/ml, did not induce IDO expression, as measured by conventional RT-PCR and Western Blot analysis. Stimulation with IFN-γ for example at 3 ng/ml or higher can also induce expression of HLAII in the cells of the invention to give a positive signal as defined herein for a cell surface marker. Said expression can be detected by those skilled in the art using any known technique that allows the detection of the expression of specific proteins. Preferably, said techniques are cell cytometry techniques.

Differentiation

The cells of the invention present the capacity to proliferate and be differentiated into at least two, more preferably three, four, five, six, seven or more cell lineages. Illustrative, non-limiting examples of cell lineages in which the cells of the invention can be differentiated include osteocytes, adipocytes, chondrocytes, tenocytes, myocytes, cardiomyocytes, hematopoietic-supporting stromal cells, endothelial cells, neurons, astrocytes, and hepatocytes.

Cells of the invention can proliferate and differentiate into cells of other lineages by conventional methods. Methods of identifying and subsequently isolating differentiated cells from their undifferentiated counterparts can be also carried out by methods well known in the art.

The cells of the invention are also capable of being expanded ex vivo. That is, after isolation, the cells of the invention can be maintained and allowed to proliferate ex vivo in culture medium. Such medium is composed of, for example, Dulbecco's Modified Eagle's Medium (DMEM), with antibiotics (for example, 100 units/ml Penicillin and 100 μg/ml Streptomycin) or without antibiotics, and 2 mM glutamine, and supplemented with 2-20% fetal bovine serum (FBS). It is within the skill of one in the art to modify or modulate concentrations of media and/or media supplements as necessary for the cells used. Sera often contain cellular and non-cellular factors and components that are necessary for viability and expansion. Examples of sera include FBS, bovine serum (BS), calf serum (CS), fetal calf serum (FCS), newborn calf serum (NCS), goat serum (GS), horse serum (HS), porcine serum, sheep serum, rabbit serum, rat serum (RS), etc. Also contemplated is, if the cells of the invention are of human origin, supplementation of cell culture medium with a human serum, preferably of autologous origin. It is understood that sera can be heat-inactivated at 55-65° C. if deemed necessary to inactivate components of the complement cascade. Modulation of serum concentrations, withdrawal of serum from the culture medium can also be used to promote survival of one or more desired cell types. Preferably, cells of the invention will benefit from FBS concentrations of about 2% to about 25%. In another embodiment, the cells of the invention can be expanded in a culture medium of definite composition, in which the serum is replaced by a combination of serum albumin, serum transferrin, selenium, and recombinant proteins including but not limited to: insulin, platelet-derived growth factor (PDGF), and basic fibroblast growth factor (bFGF) as known in the art.

Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, and the like.

Antimicrobial agents are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone®), ampicillin, gentamicin, bleomycin, hygromacin, kanamycin, mitomycin, etc.

Hormones can also be advantageously used in cell culture and include, but are not limited to, D-aldosterone, diethylstilbestrol (DES), dexamethasone, b-estradiol, hydrocortisone, insulin, prolactin, progesterone, somatostatin/human growth hormone (HGH), etc.

The maintenance conditions of the cells of the invention can also contain cellular factors that allow cells to remain in an undifferentiated form. It is apparent to those skilled in the art that prior to differentiation, supplements that inhibit cell differentiation must be removed from the culture medium. It is also apparent that not all cells will require these factors. In fact, these factors may elicit unwanted effects, depending on the cell type.

Advantageously, the cells of the invention lack in vivo tumorigenic activity. Thus, said cells are characterized in that they do not present tumorigenic activity, i.e., they do not present an altered behaviour or proliferative phenotype which gives rise to a tumour cell In an embodiment, the cells of the invention can be administered to a subject suffering from autoimmune diseases, inflammatory diseases or immunologically mediated diseases, such as rejection of transplanted organs and tissues, for suppressing the immune response. Thus, it is necessary that the cells of the invention do not present tumorigenic activity.

The tumorigenic activity of the cells of the invention can be tested by performing animal studies using immunodeficient mice strains. In these experiments, several million cells are implanted subcutaneously in the recipient animals, which are maintained for several weeks and analyzed for tumour formation. A particular assay is disclosed in Example 3.

The cells of the invention can be transfected or genetically engineered to express, at least, one antigenic polypeptide. In an embodiment, the antigen comprises a purified or a synthetic or recombinant polypeptide representing a specific antigen to which it is desired that tolerance is to be induced, or a short synthetic polypeptide fragment derived from the amino acid sequence of such an antigen. Preferably, the source of antigen comprises antigens expressed by a donor tissue graft. Also preferably, the source of antigen comprises a protein to which a patient has an autoimmune disorder.

Method for Isolating IDO-Expressing Cells

In an aspect, the present invention relates to a method for isolating a cell population from connective tissue, wherein the cells of said cell population present a phenotype characterized in that (i) they do not express markers specific from APCs; (ii) they do not express IDO constitutively; (iii) they express IDO upon stimulation with IFN-γ; and (iv) they present capacity to be differentiated into at least two cell lineages, said method comprising the steps of:

(i) preparing a cell suspension from a sample of a connective tissue;
(ii) recovering the cells from said cell suspension;
(iii) incubating said cells in a suitable cell culture medium on a solid surface under conditions which allow cells to adhere to the solid surface and proliferate;
(iv) washing said solid surface after incubation to remove non-adhered cells;
(v) selecting the cells which after being passaged at least twice in such medium remain adhered to said solid surface; and
(vi) confirming that the selected cell population presents the phenotype of interest.

As used herein, the term "solid surface" refers to any material that allows the cells of the invention to adhere. In a particular embodiment said material is a plastic material treated to promote the adhesion of mammalian cells to its surface, for example commercially available polystyrene plates optionally coated with poly-D-Lysine or other reagents.

Steps (i)-(vi) can be carried out by conventional techniques known by those skilled in the art. Briefly, the cells of the invention can be obtained by conventional means from any suitable source of connective tissue from any suitable animal, including humans, e.g., from human adipose tissue or cartilaginous tissue. The animal can be alive or dead, so long as connective tissue cells within the animal are viable. Typically, human adipose cells are obtained from living donors, using well-recognized protocols such as surgical or suction lipectomy. Indeed, as liposuction procedures are so common, liposuction effluent is a particularly preferred source from which the cells of the invention can be derived. Thus, in a particular embodiment, the cells of the invention are from the stromal fraction of human adipose tissue obtained by liposuction. In another particular embodiment, the cells of the invention are from human hyaline articular cartilage obtained by arthroscopic techniques. In another particular embodiment, the cells of the invention are from human skin obtained by biopsy techniques. Also in another particular embodiment, the cells of the invention are from human bone marrow obtained by aspiration.

The sample of connective tissue is, preferably, washed before being processed to separate the cells of the invention from the remainder of the material. In a protocol, the sample of connective tissue is washed with physiologically-compatible saline solution (e.g., phosphate buffered saline (PBS)) and then vigorously agitated and left to settle, a step that removes loose matter (e.g., damaged tissue, blood, erythrocytes, etc) from the tissue. Thus, the washing and settling steps generally are repeated until the supernatant is relatively clear of debris. The remaining cells generally will be present in clumps of various sizes, and the protocol proceeds using steps gauged to degrade the gross structure while minimizing damage to the cells themselves. One method of achieving this end is to treat the washed lumps of cells with an enzyme that weakens or destroys bonds between cells (e.g., collagenase, dispase, trypsin, etc.). The amount and duration of such enzymatic treatment will vary, depending on the conditions employed, but the use of such enzymes is generally known in the art. Alternatively or in conjunction with such enzymatic treatment, the lumps of cells can be degraded using other treatments, such as mechanical agitation, sonic energy, thermal energy, etc. If degradation is accomplished by enzymatic methods, it is desirable to neutralize the enzyme following a suitable period, to minimize deleterious effects on the cells.

The degradation step typically produces a slurry or suspension of aggregated cells and a fluid fraction containing generally free stromal cells (e.g., red blood cells, smooth muscle cells, endothelial cells, fibroblast cells, and stem cells). The next stage in the separation process is to separate the aggregated cells from the cells of the invention. This can be accomplished by centrifugation, which forces the cells into a pellet covered by a supernatant. The supernatant then can be discarded and the pellet suspended in a physiologically-compatible fluid. Moreover, the suspended cells typically include erythrocytes, and in most protocols it is desirable to lyse them. Methods for selectively lysing erythrocytes are known in the art, and any suitable protocol can be employed (e.g., incubation in a hyper -or hypotonic medium, by lysis using ammonium chloride, etc.). Of course, if the erythrocytes are lysed, the remaining cells should then be separated from the lysate, for example by filtration, sedimentation, or density fractionation.

Regardless of whether the erythrocytes are lysed, the suspended cells can be washed, re-centrifuged, and resuspended one or more successive times to achieve greater purity. Alternatively, the cells can be separated on the basis of cell surface marker profile or on the basis of cell size and granularity.

Following the final isolation and resuspension, the cells can be cultured and, if desired, assayed for number and viability to assess the yield. Desirably, the cells will be cultured without differentiation, on a solid surface, using a suitable cell culture media, at the appropriate cell densities and culture conditions. Thus, in a particular embodiment, cells are cultured without differentiation on a solid surface, usually made of a plastic material, such as Petri dishes or cell culture flasks, in the presence of a suitable cell culture medium [e.g., DMEM, typically supplemented with 5-15% (e.g., 10%) of a suitable serum, such as fetal bovine serum or human serum], and incubated under conditions which allow cells to adhere to the solid surface and proliferate. After incubation, cells are washed in order to remove non-adhered cells and cell fragments. The cells are maintained in culture in the same medium and under the same conditions until they reach the adequate confluence, typically, about 80% cell confluence, with replacement of the cell culture medium when necessary. After reaching the desired cell confluence, the cells can be expanded by means of consecutive passages using a detachment agent such as trypsin and seeding onto a bigger cell culture surface at the appropriate cell density (usually 2,000-10,000 cells/cm$^2$). Thus, cells are then passaged at least two times in such medium without differentiating, while still retaining their developmental phenotype, and more preferably, the cells can be passaged at least 10 times (e.g., at least 15 times or even at least 20 times) without losing developmental phenotype. Typically, the cells are plated at a desired density such as between about 100 cells/cm$^2$ to about 100,000 cells/cm$^2$ (such as about 500 cells/cm$^2$ to about 50,000 cells/cm$^2$, or, more particularly, between about 1,000 cells/cm² to about 20,000 cells/cm²). If plated at lower densities (e.g., about 300 cells/cm²), the cells can be more easily clonally isolated. For example, after a few days, cells plated at such densities will proliferate into an homogeneous population. In a particular embodiment, the cell density is between 2,000-10,000 cells/cm².

Cells which remain adhered to the solid surface after such treatment comprising at least two passages are selected and the phenotype of interest is analyzed by conventional methods in order to confirm the identity of the cells of the invention as will be mentioned below. Cells which remain adhered to the solid surface after the first passage are from heterogeneous origin; therefore, said cells must be subjected to at least another passage. As a result of the above method, a homogeneous cell population having the phenotype of interest is obtained. Example 1 describes in a detailed manner the isolation of the cells of the invention from human adipose tissue and from human cartilaginous tissue.

Usually, cells which remain adhered to the solid surface after the second passage show the phenotype of interest, although it has to be confirmed so that the cells can be used according to the invention. Therefore, the adhesion of cells to the solid surface after at least two passages constitutes a preferred embodiment of the invention for selecting the cells of the invention. Confirmation of the phenotype of interest can be carried out by using conventional means.

Cell-surface markers can be identified by any suitable conventional technique, usually based on a positive/negative selection; for example, monoclonal antibodies against cell-surface markers, whose presence/absence in the cells has to be confirmed, can be used; although other techniques can also be used. Thus, in a particular embodiment, monoclonal antibodies against one, two, three, four, five, six, seven of or preferably all of CD11b, CD11c, CD14, CD45, HLAII, CD31, CD34 and CD133 are used in order to confirm the absence of said markers in the selected cells; and monoclonal antibodies against one, two, three, four, of or preferably all of CD9, CD44, CD54, CD90 and CD105 are used in order to confirm the presence thereof or detectable expression levels of, at least one of and preferably all of, said markers. Said monoclonal antibodies are known, commercially available or can be obtained by a skilled person in the art by conventional methods.

IFN-γ-inducible IDO activity in the selected cells can be determined by any suitable conventional assay. For example, the selected cells can be stimulated with IFN-γ and assayed for IDO expression; then conventional Western-blot analysis for IDO protein expression can be performed and IDO enzyme activity following IFN-Γ stimulation of the selected cells can be measured by tryptophan-to-kynurenine conversion with for example via High Performance Liquid Chromatography (HPLC) analysis and photometric determination of kynurenine concentration in the supernatant as the readout. Since the cells of the invention express IDO under certain conditions, any suitable technique which allows the detection of IDO activity following IFN-γ stimulation may be used for selecting the cells of the invention. A suitable assay for determining IFN-γ-inducible IDO activity in the selected cells is disclosed in Example 2. The amount of IDO produced depends on the number of cells per square centimetre, which is preferably at a level of 5000 cells/cm² or more, but not limited to this concentration and the concentration of IFN-γ, which ideally is 3 ng/ml or more, but not limited to this concentration. The activity of IDO produced under the described conditions will result in a detectable production of kynurenine in the μM range after 24 hours or more.

The capacity of the selected cells to differentiate into at least two cell lineages can be assayed by conventional methods as known in the art.

The cells and cell populations provided by the instant invention can be clonally expanded, if desired, using a suitable method for cloning cell populations. For example, a proliferated population of cells can be physically picked and seeded into a separate plate (or the well of a multi-well plate). Alternatively, the cells can be subcloned onto a multi-well plate at a statistical ratio for facilitating placing a single cell into each well (e.g., from about 0.1 to about 1 cell/well or even about 0.25 to about 0.5 cells/well, such as 0.5 cells/well). Of course, the cells can be cloned by plating them at low density (e.g., in a Petri dish or other suitable substrate) and isolating them from other cells using devices such as a cloning rings. The production of a clonal population can be expanded in any suitable culture medium. In any event, the isolated cells can be cultured to a suitable point when their developmental phenotype can be assessed.

Further investigations carried out by the inventors have shown that ex vivo expansion of the cells of the invention without inducing differentiation can be accomplished for extended time periods for example by using specially screened lots of suitable serum (such as fetal bovine serum or human serum). Methods for measuring viability and yield are known in the art (e. g., trypan blue exclusion).

Any of the steps and procedures for isolating the cells of the cell population of the invention can be performed manually, if desired. Alternatively, the process of isolating such cells can be facilitated and/or automated through one or more suitable devices, examples of which are known in the art.

Uses of the Cells of the Invention

The cells of the invention can be used for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues.

Thus, in another aspect, the cells of the invention are used as a medicament. In a particular embodiment, medicaments containing the cells of the invention may be used for inducing transplantation tolerance, or for treating, and thereby alleviating, symptoms of autoimmune or inflammatory disorders, or immunologically mediated diseases including rejection of transplanted organs and tissues, in a subject suffering from any of said disorders or diseases. Thus, the cells of the invention can be used to therapeutically or prophylactically treat and thereby alleviate symptoms of autoimmune or inflammatory disorders in a subject suffering from any of said disorders or to alleviate symptoms of immunologically mediated diseases in a subject suffering from said diseases.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

The mechanisms by which certain conditions may result in autoimmunity in some subjects are generally not well understood, but may involve both genetic and extrinsic factors. For example, bacteria, viruses or drugs may play a role in triggering an autoimmune response in a subject who already has a genetic predisposition to the autoimmune disorder. It has been proposed, for example, that subjects with certain common allergies are more susceptible to autoimmune disorders.

Practically any autoimmune disease, inflammatory disorder or immunological mediated disease can be treated with the cells of the invention. Illustrative, non-limiting examples of said diseases and disorders which can be treated are those previously listed under heading "Definitions". In a particular embodiment, said inflammatory disease is a chronic inflammatory disease, such as, e.g., IBD or RA.

In other aspect, the present invention relates to the use of the cells of the invention for the preparation of a medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the cells of the invention for the preparation of a medicament for suppressing the immune response, or for inducing transplantation tolerance, or for treating autoimmune diseases, or for treating inflammatory disorders. Examples of said autoimmune diseases and inflammatory diseases have been previously mentioned. In a particular embodiment, disease is an inflammatory disease, such as a chronic inflammatory disease, e.g., IBD or RA.

In another aspect, the present invention relates to the use of the cells of the invention for the preparation or generation of regulatory T-cells (T-reg), i.e., cells that actively suppress activation of the immune system and prevent pathological self-reactivity, i.e. an autoimmune disease.

T-reg Cells of the Invention

The invention further refers, in other aspect, to regulatory T-cells (T-reg), i.e., cells (including Foxp3+CD4+CD25+ T-reg and IL-10/TGFb-producing Tr1 cells) that actively suppress activation of the immune system and prevent pathological self-reactivity, i.e. an autoimmune disease, obtainable from the cells of the invention, hereinafter referred to T-reg cells of the invention.

Thus, in other aspect, the present invention relates to a method for the isolation of a T-reg cell population of the invention, which comprises:

(a) contacting a cell population of the invention with peripheral blood leukocytes, and (b) selecting the T-reg cell population of the invention.

Consequently, the cells of the invention can be used to produce a subset of T-cells, the T-reg cells of the invention, which constitutes an additional aspect of the present invention. The T-reg cells of the invention can be isolated by conventional means known by a skilled person in the art.

The T-reg cells of the invention can be used for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Said use constitutes an additional aspect of the present invention.

Thus, in another aspect, the T-reg cells of the invention are used as a medicament. In a particular embodiment, medicaments containing the T-reg cells of the invention may be used for inducing transplantation tolerance, or for treating, and thereby alleviating, symptoms of autoimmune or inflammatory disorders, or immunologically mediated diseases including rejection of transplanted organs and tissues, in a subject suffering from any of said disorders or diseases. Thus, the T-reg cells of the invention can be used to therapeutically or prophylactically treat and thereby alleviating symptoms of autoimmune or inflammatory disorders in a subject suffering from any of said disorders or to alleviate symptoms of immunologically mediated diseases in a subject suffering from said diseases.

Practically any autoimmune disease, inflammatory disorder or immunological mediated disease can be treated with the T-reg cells of the invention. Illustrative, non-limiting examples of said diseases and disorders which can be treated are those previously listed under heading "Definitions". In a particular embodiment, said inflammatory disease is a chronic inflammatory disease, such as, e.g., IBD or RA.

In other aspect, the present invention relates to the use of the T-reg cells of the invention for the preparation of a medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the T-reg cells of the invention for the preparation of a medicament for suppressing the immune response, or for inducing transplantation tolerance, or for treating autoimmune diseases, or for treating inflammatory disorders. Examples of said autoimmune diseases and inflammatory diseases have been previously mentioned. In a particular embodiment, disease is an inflammatory disease, such as a chronic inflammatory disease, e.g., IBD or RA.

The invention also provides the use of cell populations of the invention in the production of Treg cells specific for a chosen antigen or group of antigens and the use of these in the treatment of disease or disorders relating to that antigen or group of antigens. Examples of such antigens are those that play a role in autoimmune diseases, such as, for example, rheumatoid arthritis, Crohn's disease, hypersensitivity reaction Type IV, lupus, psoriasis and other autoimmune disorders known in the art and described elsewhere herein. Briefly, cell populations of the invention are cultured in vitro in the presence of a chosen antigen, group of antigens or cell types expressing and/or presenting this antigen or antigens. The cells of the invention can optionally be prestimulated with IFNγ, LPS or other activating agents known in the art. After a culture period of about 2, 4, 6, 12, 24, 48 or more hours, preferably between about 12 to about 24 hours, the cell population of the invention is further co-cultured, optionally after the removal of the antigen, group of antigens or cells carrying said antigen, with peripheral blood leukocytes obtained from a subject. This co-culturing will result in the production of Treg cells specific for the chosen antigen, which can be used for treatment of the subject. Optionally these Treg cells can be expanded in number ex vivo using culture techniques known in the art before being administered to the patient. Without wishing to be bound by theory, the Inventors believe that the cell populations of the invention are capable of presenting the chosen antigen via HLA Class II on the cell surface (seeming induced by IFNγ) to the peripheral blood leukocytes such that Treg cells are augmented and or activated within the population of peripheral blood leukocytes. As shown in Example 11, the Inventors have demonstrated that cell populations of the invention are able to phagocytose small molecular weight molecules and thus are capable of presenting such molecules after IFNγ stimulation via HLA Class II molecules. The presentation of chosen antigen via this mechanism with the interaction with the peripheral blood leukocytes is believed to result in the above described Treg cell production. As an alternative treatment methodology, as described in Example 7 a cell population of invention is administered directly in vivo without any co-culturing and can generate specific Treg cells, which in turn can treat a disorder.

Thus the invention provides an in vitro method of obtaining Treg cells specific for a chosen antigen or group of antigens, which comprises:
(a) contacting a cell population of the invention with said chosen antigen or group of antigens;
(b) bringing said cell population into contact with peripheral blood leukocytes;
(c) selecting a T-reg cell population specific for said chosen antigen or group of antigens The invention also provides the use of the specific Treg cells of step (c) in the treatment of diseases and disorders related to said chosen antigen or groups of antigens by administration of said Treg cells to the subject from which the peripheral blood leukocytes were obtained. The cell population of the invention as used in this method may be from the subject (autologous) or from a donor (allogeneic).

Irradiated Cells of the Invention

If desired, the cells of the invention can be irradiated using a suitable controlled source of ionizing radiation, such a gamma irradiator device. The irradiation conditions must be experimentally adjusted by a person skilled in the art to determine the required exposure time to impart a radiation dose that cause the long term growth arrest of the cells of the invention. Said radiation dose can be for example 1-100, 5-85, 10-70, 12-60 Gy or more preferably 15-45 Gy.

Since the cells of the invention can be used for therapeutic uses, irradiation of the cells of the invention before administration to the subject may result beneficial since said irradiation treatment makes cells incapable to proliferate or survive for long time periods in the subject. Said irradiated cells constitute a further aspect of the instant invention.

The irradiated cells of the invention can be used for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Said use constitutes an additional aspect of the present invention.

Thus, in another aspect, the irradiated cells of the invention are used as a medicament. In a particular embodiment, medicaments containing the irradiated cells of the invention may be used for inducing transplantation tolerance, or for treating, and thereby alleviating, symptoms of autoimmune or inflammatory disorders, or immunologically mediated diseases including rejection of transplanted organs and tissues, in a subject suffering from any of said disorders or diseases. Thus, the irradiated cells of the invention can be used to therapeutically or prophylactically treat and thereby alleviating symptoms of autoimmune or inflammatory disorders in a subject suffering from any of said disorders or to alleviate symptoms of immunologically mediated diseases in a subject suffering from said diseases.

Practically any autoimmune disease, inflammatory disorder or immunological mediated disease can be treated with the irradiated cells of the invention. Illustrative, non-limiting examples of said diseases and disorders which can be treated are those previously listed under heading "Definitions". In a particular embodiment, said inflammatory disease is a chronic inflammatory disease, such as, e.g., IBD or RA.

In other aspect, the present invention relates to the use of the irradiated cells of the invention for the preparation of a medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the irradiated cells of the invention for the preparation of a medicament for suppressing the immune response, or for inducing transplantation tolerance, or for treating autoimmune diseases, or for treating inflammatory disorders. Examples of said autoimmune diseases and inflammatory diseases have been previously mentioned. In a particular embodiment, disease is an inflammatory disease, such as a chronic inflammatory disease, e.g., IBD or RA.

IFN-γ-pre-stimulated Cells of the Invention

Also, if desired, the cells of the invention can be pre-stimulated with IFN-γ. The methods for pre-stimulation with IFN-γ are evident to those skilled in the art, and a procedure is given in Example 2. Preferably, the cells are pre-stimulated using a concentration of IFN-γ between 0.1 and 100, 0.5 and 85, 1 and 70, 1.5 and 50, 2.5 and 40 ng/ml or more preferably 3 and 30 ng/ml, and a stimulation time preferably longer than 12 hours, for example, 13, 18, 24, 48, 72 hours or more.

Since the cells of the invention can be used for therapeutic uses, pre-stimulation of the cells of the invention with IFN-γ before administration to the subject may result beneficial since the time period between IFN-γ-pre-stimulated cell administration and IDO expression in the subject can be reduced.

Thus, in another aspect, the present invention refers to a method which comprises the treatment of the cells of the invention with IFN-γ in order to pre-stimulate said cells. The cells obtainable according to said method, hereinafter referred to "IFN-γ-pre-stimulated cells of the invention", constitutes an additional aspect of the present invention. The IFN-γ-pre-stimulated cells of the invention can be isolated by conventional means known by a skilled person in the art.

The IFN-γ-pre-stimulated cells of the invention can be used for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Said use constitutes an additional aspect of the present invention.

Thus, in another aspect, the IFN-γ-pre-stimulated cells of the invention are used as a medicament. In a particular embodiment, medicaments containing the IFN-γ-pre-stimulated cells of the invention may be used for inducing transplantation tolerance, or for treating, and thereby alleviating, symptoms of autoimmune or inflammatory disorders, or immunologically mediated diseases including rejection of transplanted organs and tissues, in a subject suffering from any of said disorders or diseases. Thus, the IFN-γ-pre-stimulated cells of the invention can be used to therapeutically or prophylactically treat and thereby alleviating symptoms of autoimmune or inflammatory disorders in a subject suffering from any of said disorders or to alleviate symptoms of immunologically mediated diseases in a subject suffering from said diseases.

Practically any autoimmune disease, inflammatory disorder or immunological mediated disease can be treated with the IFN-γ-pre-stimulated cells of the invention. Illustrative, non-limiting examples of said diseases and disorders which can be treated are those previously listed under heading "Definitions". In a particular embodiment, said inflammatory disease is a chronic inflammatory disease, such as, e.g., IBD or RA.

In other aspect, the present invention relates to the use of the IFN-γ-pre-stimulated cells of the invention for the preparation of a medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the IFN-γ-pre-stimulated cells of the invention for the preparation of a medicament for suppressing the immune response, or for inducing transplantation tolerance, or for treating autoimmune diseases, or for treating inflammatory disorders. Examples of said autoimmune diseases and inflammatory diseases have been previously mentioned. In a particular embodiment, disease is an inflammatory disease, such as a chronic inflammatory disease, e.g., IBD or RA.

Irradiated IFN-γ-pre-stimulated Cells of the Invention and IFN-γ-pre-stimulated Irradiated Cells of the Invention Furthermore, if desired, the cells of the invention can be subjected to the treatments of irradiation and IFN-γ-stimulation, in any order; i.e., cells of the invention can be subjected firstly to irradiation and the resulting cells can be subsequently subjected to IFN-γ-stimulation, or vice versa, cells of the invention can be subjected firstly to IFN-γ-stimulation and subsequently the resulting cells can be subjected to irradiation.

Thus, in an aspect, the cells of the invention can be pre-stimulated with IFN-γ and the resulting cells (IFN-γ-pre-stimulated cells of the invention) can be irradiated to render irradiated cells hereinafter referred to as "irradiated IFN-γ-pre-stimulated cells of the invention".

In another aspect, the cells of the invention can be irradiated and the resulting cells (irradiated cells of the invention) can be pre-stimulated with IFN-γ to render IFN-γ-prestimulated cells hereinafter referred to as "IFN-γ-pre-stimulated irradiated cells of the invention".

Methods for pre-stimulation cells with IFN-γ as well as methods for irradiating cells are well-known for those skilled in the art and some of them have been previously mentioned above. Any of said methods can be used.

Thus, in another aspect, the present invention refers to a method which comprises subjecting the cells of the invention to (i) irradiation, and (ii) stimulation with IFN-γ, wherein treatments (i) and (ii) can be carried out in any order, in order to irradiate IFN-γ-pre-stimulated cells or to IFN-γ-pre-stimulate irradiated cells. The cells obtainable according to said method, herein referred to as "irradiated IFN-γ-pre-stimulated cells of the invention" or "IFN-γ-pre-stimulated irradiated cells of the invention", respectively, constitutes additional aspects of the present invention. Said irradiated IFN-γ-pre-stimulated cells of the invention as well as said IFN-γ-pre-stimulated irradiated cells of the invention can be isolated by conventional means known by a skilled person in the art.

Since the cells of the invention can be used for therapeutic uses, administration to a subject of the cells of the invention previously subjected to irradiation and IFN-γ-stimulation, in any order, may result beneficial for the reasons previously mentioned (e.g., subjecting cells to an irradiation treatment to make the cells incapable of proliferating or surviving for long time periods in the subject, whereas pre-stimulation of cells with IFN-γ before administration to the subject may involve a reduction in the time period between IFN-γ-pre-stimulated cell administration and IDO expression in the subject.

The irradiated IFN-γ-pre-stimulated cells of the invention as well as the IFN-γ-pre-stimulated irradiated cells of the invention can be used for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Said use constitutes an additional aspect of the present invention.

Thus, in another aspect, the irradiated IFN-γ-pre-stimulated cells of the invention as well as the IFN-γ-pre-stimulated irradiated cells of the invention are used as a medicament. In a particular embodiment, medicaments containing the irradiated IFN-γ-pre-stimulated cells of the invention or the IFN-γ-pre-stimulated irradiated cells of the invention may be used for inducing transplantation tolerance, or for treating, and thereby alleviating, symptoms of autoimmune or inflammatory disorders, or immunologically mediated diseases including rejection of transplanted organs and tissues, in a subject suffering from any of said disorders or diseases. Thus, the irradiated IFN-γ-pre-stimulated cells of the invention as well as the IFN-γ-pre-stimulated irradiated cells of the invention can be used to therapeutically or prophylactically treat and thereby alleviating symptoms of autoimmune or inflammatory disorders in a subject suffering from any of said disorders or to alleviate symptoms of immunologically mediated diseases in a subject suffering from said diseases.

Practically any autoimmune disease, inflammatory disorder or immunological mediated disease can be treated with the irradiated IFN-γ-pre-stimulated cells of the invention or with the IFN-γ-pre-stimulated irradiated cells of the invention. Illustrative, non-limiting examples of said diseases and disorders which can be treated are those previously listed under heading "Definitions". In a particular embodiment, said inflammatory disease is a chronic inflammatory disease, such as, e.g., IBD or RA.

In other aspect, the present invention relates to the use of the irradiated IFN-γ-pre-stimulated cells of the invention or the IFN-γ-pre-stimulated irradiated cells of the invention for the preparation of a medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the irradiated IFN-γ-pre-stimulated cells of the invention or the IFN-γ-pre-stimulated irradiated cells of the invention for the preparation of a medicament for suppressing the immune response, or for inducing transplantation tolerance, or for treating autoimmune diseases, or for treating inflammatory disorders. Examples of said autoimmune diseases and inflammatory diseases have been previously mentioned. In a particular embodiment, disease is an inflammatory disease, such as a chronic inflammatory disease, e.g., IBD or RA.

Pharmaceutical Compositions

The present invention provides pharmaceutical compositions for the treatment, prophylaxis, and amelioration of one or more symptoms associated with a disorder in which modulation of a subject's immune system is beneficial such as autoimmune diseases, inflammatory disorders, and immunologically mediated diseases including rejection of transplanted organs and tissues.

Thus, in another aspect, the invention relates to a pharmaceutical composition, hereinafter referred to as the pharmaceutical composition of the invention, comprising a cell of the invention, or a T-reg cell of the invention, or an irradiated cell of the invention, or an IFN-γ-pre-stimulated cell of the invention, or an irradiated IFN-γ-pre-stimulated cell of the invention, or an IFN-γ-pre-stimulated irradiated cell of the invention, and an acceptable pharmaceutically carrier. Combinations of two or more of said type of cells are included within the scope of the pharmaceutical compositions provided by the instant invention.

The pharmaceutical composition of the invention comprises a prophylactically or therapeutically effective amount of one or more prophylactic or therapeutic agents (i.e., cell of the invention, or a T-reg cell of the invention, or an irradiated cell of the invention, or an IFN-γ-pre-stimulated cell of the invention, or an irradiated IFN-γ-pre-stimulated cell of the invention, or an IFN-γ-pre-stimulated irradiated cell of the invention, or a combination thereof), and a pharmaceutically acceptable carrier. In a specific embodiment, the term "pharmaceutically acceptable" means approved by a regulatory agency of the Federal or a state government or listed in the U.S. Pharmacopeia, or European Pharmacopeia, or other generally recognized pharmacopeia for use in animals, and more particularly in humans. The term "carrier" refers to a diluent, adjuvant, excipient, or vehicle with which the therapeutic agent is administered. The composition, if desired, can also contain minor amounts of pH buffering agents. Examples of suitable pharmaceutical carriers are described in "Remington's Pharmaceutical Sciences" by E. W. Martin. Such compositions will contain a prophylactically or therapeutically effective amount of a prophylactic or therapeutic agent preferably in purified form, together with a suitable amount of carrier so as to provide the form for proper administration to the subject. The formulation should suit the mode of administration. In a preferred embodiment, the pharmaceutical compositions are sterile and in suitable form for administration to a subject, preferably an animal subject, more preferably a mammalian subject, and most preferably a human subject.

The pharmaceutical composition of the invention may be in a variety of forms. These include, for example, solid, semi-solid, and liquid dosage forms, such as lyophilized preparations, liquids solutions or suspensions, injectable and infusible solutions, etc. The preferred form depends on the intended mode of administration and therapeutic application.

The administration of the cell population of the invention, or the pharmaceutical composition comprising same, to the subject in need thereof can be carried out by conventional means. In a particular embodiment, said cell population is administered to the subject by a method which involves transferring the cells to the desired tissue, either in vitro (e.g., as a graft prior to implantation or engrafting) or in vivo, to the animal tissue directly. The cells can be transferred to the desired tissue by any appropriate method, which generally will vary according to the tissue type. For example, cells can be transferred to graft by bathing the graft (or infusing it) with culture medium containing the cells. Alternatively, the cells can be seeded onto the desired site within the tissue to establish a population. Cells can be transferred to sites in vivo using devices such as catheters, trocars, cannulae, stents (which can be seeded with the cells), etc.

The cells of the invention can be irradiated before administration to the subject. This treatment makes cells incapable to proliferate or survive for long time periods in the subject. Thus, in a particular embodiment, the pharmaceutical composition of the invention comprises irradiated cells of the invention.

Also, the cells of the invention can be pre-stimulated with IFN-γ, prior to administration to the subject in order to reduce the time period between cell administration and IDO expression in the subject. Thus, in a particular embodiment, the pharmaceutical composition of the invention comprises IFN-γ-pre-stimulated cells of the invention.

Further, the cells of the invention can be both irradiated and pre-stimulated with IFN-γ, in any order, prior to administration to the subject. Thus, in a particular embodiment, the pharmaceutical composition of the invention comprises irradiated IFN-γ-pre-stimulated cells of the invention or IFN-γ-pre-stimulated irradiated cells of the invention.

The cell populations and pharmaceutical compositions of the invention can be used in a combination therapy. In a specific embodiment, the combination therapy is administered to a subject with an inflammatory disorder that is refractory to one or more anti-inflammatory agents. In another embodiment, the combination therapy is used in conjunction with other types of anti-inflammatory agents including, but not limited to, non-steroidal anti-inflammatory drugs (NSAIDs), steroidal anti-inflammatory drugs, beta-agonists, anticholingeric agents, and methyl xanthines. Examples of NSAIDs include, but are not limited to, ibuprofen, celecoxib, diclofenac, etodolac, fenoprofen, indomethacin, ketorolac, oxaprozin, nabumentone, sulindac, tolmentin, rofecoxib, naproxen, ketoprofen, nabumetone, etc. Such NSAIDs function by inhibiting a cyclooxygenase enzyme (e.g., COX-1 and/or COX-2). Examples of steroidal anti-inflammatory drugs include, but are not limited to, glucocorticoids, dexamethasone, cortisone, hydrocortisone, prednisone, prednisolone, triamcinolone, azulfidine, and eicosanoids such as thromboxanes, and leukotrienes. Monoclonal antibodies, such as Infliximab, can also be used.

In accordance with the above embodiment, the combination therapies of the invention can be used prior to, concurrently or subsequent to the administration of such anti-inflammatory agents. Further, such anti-inflammatory agents do not encompass agents characterized herein as lymphoid tissue inducers and/or immunomodulatory agents.

Method for Distinguishing Adult Multipotent Cells from Differentiated Cells

The expression of IDO upon stimulation with IFN-γ can be used for distinguishing cells which express said enzyme from cells which do not express IDO.

Thus, in another aspect, the invention relates to a method for distinguishing adult multipotent cells from differentiated cells comprising the step of verifying whether the multipotent cell expresses IDO upon stimulation with IFN-γ. The determination of IDO upon stimulation with IFN-γ can be carried by any conventional technique; in an embodiment, the determination of IDO upon stimulation with IFN-γ can be carried out as disclosed in Example 2.

As previously mentioned, the cells of the cell population of the invention are characterized in that they do not express IDO constitutively, but only upon stimulation with IFN-γ. Moreover, aside from IFN-γ no other pro-inflammatory molecule such us IL-1, TNF-α, or endotoxin is able to induce by itself the expression of IDO in the cells of the cell population of the invention. This feature can be used for distinguishing the cells of the cell population of the invention from other cells.

Kits

In another aspect, the invention refers to a kit comprising a cell population containing (i) cells of the invention and/or (ii) T-reg cells of the invention and/or (iii) irradiated cells of the invention and/or (iv) IFN-γ-pre-stimulated cells of the invention, and/or (v) irradiated IFN-γ-pre-stimulated cells of the invention, and/or (vi) IFN-γ-pre-stimulated irradiated cells of the invention. Kits of the invention may comprise one, two, three, four, five or all of such cell types.

Methods of Treatment

In other aspect, the present invention refers to the use of a cell population containing cells of the invention, T-reg cells population of the invention, irradiated cells of the invention, IFN-γ-pre-stimulated cells of the invention, irradiated IFN-γ-pre-stimulated cells of the invention, or IFN-γ-pre-stimulated irradiated cells of the invention for preventing, treating, or ameliorating one or more symptoms associated with autoimmune diseases, inflammatory disorders, or immunologically mediated diseases including rejection of transplanted organs and tissues. In a particular embodiment, said cell populations may be used for inducing transplantation tolerance, or for treating, and thereby alleviating, symptoms of autoimmune or inflammatory disorders, or immunologically mediated diseases in a subject suffering from said disorders or diseases. Examples of said autoimmune diseases and inflammatory diseases have been previously mentioned. In a particular embodiment, disease is an inflammatory disease, such as a chronic inflammatory disease, e.g., IBD or RA.

In other aspect, the present invention provides methods of preventing, treating, or ameliorating one or more symptoms associated with autoimmune diseases, inflammatory disorders, or immunologically mediated diseases, in a subject suffering from said disorders or diseases, which comprises administering to said subject in need of such treatment of a prophylactically or therapeutically effective amount of a cell population containing cells of the invention, T-reg cells of the invention, irradiated cells of the invention, IFN-γ-pre-stimulated cells of the invention, irradiated IFN-γ pre-stimulated cells of the invention, or IFN-γ-pre-stimulated irradiated cells of the invention. In a particular embodiment, said cell populations may be used for inducing transplantation tolerance, or for treating, and thereby alleviating, symptoms of autoimmune or inflammatory disorders, or immunologically mediated diseases in a subject suffering from said disorders or diseases. Examples of said autoimmune diseases and inflammatory diseases have been previously mentioned. In a particular embodiment, disease is an inflammatory disease, such as a chronic inflammatory disease, e.g., IBD or RA.

EXAMPLES

The invention will now be described in more detail, by way of examples which in no way are meant to limit the scope of the invention, but, rather, these examples will serve to illustrate the invention with reference to the accompanying figures.

Example 1

Isolation and expansion of cells of the invention

I. Material and Methods

Isolation of Cells of the Invention from Adipose Tissue

Human adipose tissue was obtained by liposuction, under local anaesthesia and general sedation. A hollow blunt-tipped cannula was introduced into the subcutaneous space through a small incision (less than 0.5 cm in diameter). With gentle suction, the cannula was moved through the adipose tissue abdominal-wall compartment for mechanical disruption of the fatty tissue. A saline solution and the vasoconstrictor epinephrine were injected into the adipose tissue compartment to minimize blood loss. In this way, 80 to 100 ml of raw lipoaspirate were obtained from each patient to be treated.

The raw lipoaspirate was washed extensively with sterile phosphate-buffered saline (PBS; Gibco BRL, Paisley, Scotland, UK) to remove blood cells, saline and local anaesthetic. The extracellular matrix was digested with a solution of type II collagenase (0.075%; Gibco BRL) in balanced salt solution (5 mg/ml; Sigma, St. Louis, USA) for 30 minutes at 37° C. to release the cellular fraction. Then the collagenase was inactivated by addition of an equal volume of cell culture medium (Dulbecco's modified Eagle's medium (DMEM; Gibco BRL) that contained 10% fetal bovine serum (FBS; Gibco BRL). The suspension of cells was centrifuged at 250×g for 10 minutes. Cells were resuspended in 0.16 M $NH_4Cl$ and allowed to stand for 5 minutes at room temperature (RT) for lysis of erythrocytes. The mixture was centrifuged at 250×g, and cells were resuspended in DMEM plus 10% FBS and 1% ampicillin/streptomycin mixture (Gibco BRL) and then they were filtered through a 40 μm mesh and were plated in tissue culture flasks at a concentration of $10\text{-}30\times10^3$ cells/$cm^2$.

Isolation of Cells of the Invention from Articular Cartilage

Human hyaline articular cartilage was obtained from the knee joint of a donor by means of arthroscopic techniques. About 4 $cm^2$ of cartilage were taken from the external margin of the phemoral condile, but the size of the biopsy may vary depending on the donor's age, the structure of the articulation and the surgeon's consideration. The biopsy was suspended in a sterile saline solution and stored at 3-8° C. until its use. Live cartilage samples should not be stored for more than 48 hours.

The cartilage biopsy was transferred to 1 ml of sterile cell culture medium containing 1% FBS, and minced to obtain tissue fragments as small as possible. The resulting cartilage fragments were suspended in a similar medium containing 0.1% (w/v) collagenase, and incubated at 37° C. with continuous and gentle agitation. After the digestion, the cell suspension obtained was filtered through a 40 μm mesh and the cells were plated onto tissue culture flasks at a concentration of $10\text{-}30\times10^3$ cells/$cm^2$.

Ex Vivo Expansion of Cells

Cells both from adipose tissue and articular cartilage were separately cultured for 24 hours at 37° C. in an atmosphere of 5% $CO_2$ in air. Then, the culture flasks were washed with PBS to remove non-adhering cells and cell fragments. The cells were maintained in culture in the same medium and under the same conditions until they reached approximately 80% confluence, with replacement of the culture medium every 3 to 4 days. Cells were then passaged with trypsin- EDTA (Gibco BRL) at a dilution of 1:3 which corresponds to a cell density of approximately about $5\text{-}6\times10^3$ cells/cm$^2$. The cellular growth kinetics of the cells isolated from human adipose tissue and cultured ex vivo for more than 25 cell population doublings is shown in FIG. 1.

Cell Characterization

Cell characterization was performed using cells at culture passages 1 to 25. Cells both from adipose tissue and articular cartilage were analyzed by means of flow cytometry by using antibodies labeled with a fluorescent marker (i.e., by fluorescence immunocytometry) for the presence/absence of a series of surface markers, which included:

Markers of antigen presenting cells (APCs): CD11b, CD11c, CD14, CD45, and HLAII.
Markers of endothelial cells: CD31.
Other markers: CD9, CD34, CD90, CD44, CD54, CD105 and CD133.

The antibodies used in the flow cytometry assay were the following:

CD9: clone MM2/57 Mouse IgG2b—FITC labeled antibody (Serotec);
CD11b: clone ICRF44 Mouse IgG1—FITC labeled antibody (Serotec);
CD11c: clone BU15 Mouse IgG1—FITC labeled antibody (Serotec);
CD14: clone UCHM1 Mouse IgG2a—FITC labeled antibody (Serotec);
CD31: clone WM59 Mouse IgG1—FITC labeled antibody (Serotec);
CD34: clone QBEND 10 Mouse IgG1—FITC labeled antibody (Serotec);
CD44: clone F10-44-2 Mouse IgG2a—FITC labeled antibody (Serotec);
CD45: clone F10-89-4 Mouse IgG2a—FITC labeled antibody (Serotec);
CD54: clone 15.2 Mouse IgG1—FITC labeled antibody (Serotec);
CD90: clone F15-42-1 Mouse IgG1—ITC labeled antibody (Serotec);
CD105: clone SN6 Mouse IgG1—FITC labeled antibody (Serotec); and
Anti Human HLA class II DP, DQ, DR: clone WR18 Mouse IgG2a—FITC labeled antibody (Serotec);
CD133: clone 293C3 Mouse IgG2b—PE labeled antibody (Miltenyi Biotec).

II. Results

Figure 2:
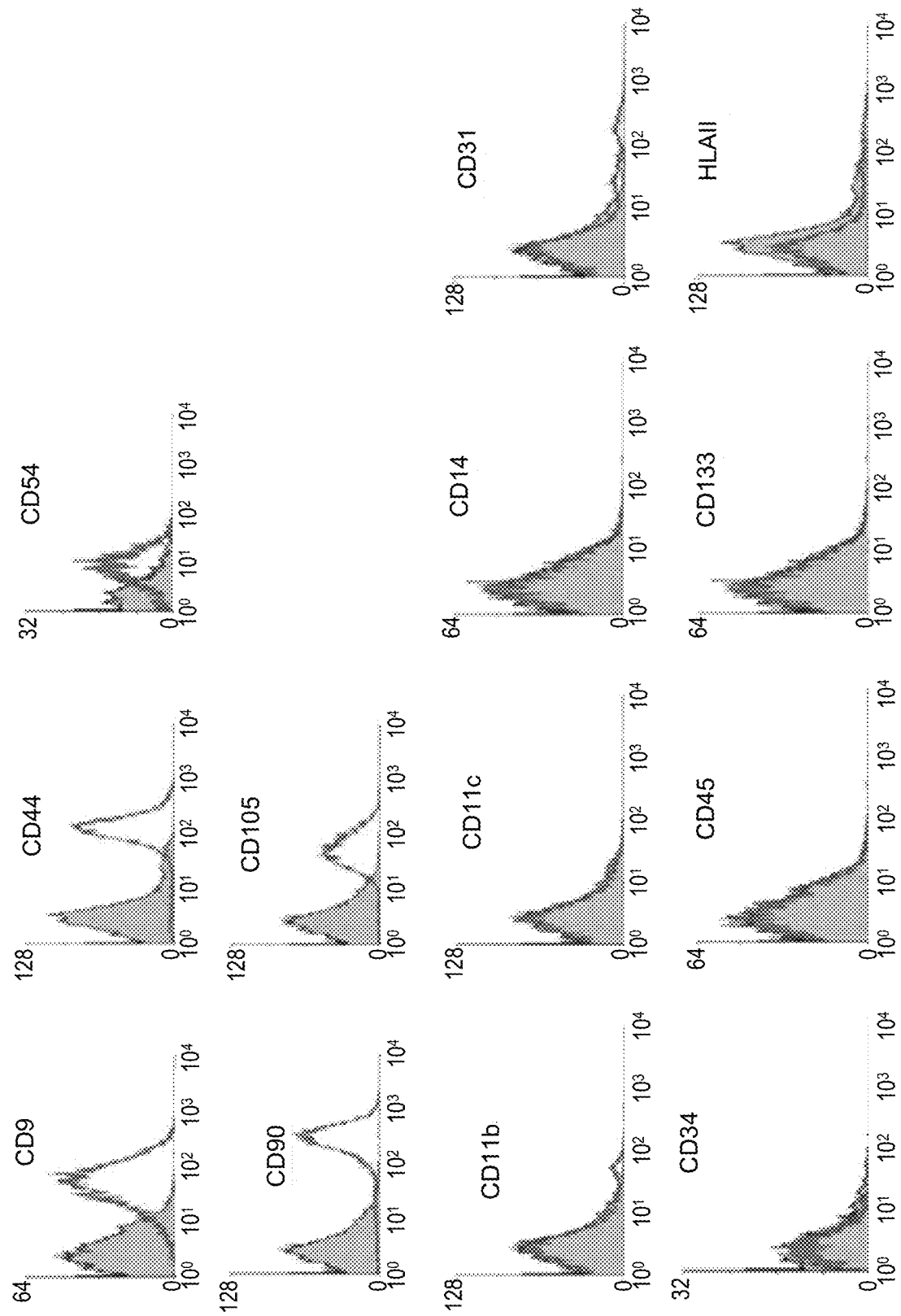
FIG. 2 shows histograms of fluorescence immunocytometry corresponding to the profile of surface markers obtained from the cells provided by the instant invention isolated from human adipose tissue. Histograms corresponding to the isotype controls (negative controls) are shown shaded in grey.

The results are collected in FIG. 2 which shows that the cells analyzed were positive for CD9, CD44, CD54, CD90 and CD105, and negative for CD11b, CD11c, CD14, CD31, CD34, CD45, CD133 and HLAII. The cells were negative for all of the tested markers which are specific for the endothelial or APC lineages (CD11b, CD11c, CD14, CD45, and HLAII).

Example 2

Induction of indolamine 2,3-dioxygenase (IDO) by interferon-gamma (IFN-γ)

I. Material and Methods

The cells of the invention isolated from human adipose tissue (Example 1), were seeded onto tissue culture plates at a density of 10,000 cells/cm$^2$, and incubated for 48 hours in the conditions previously described for cell expansion. Then, different pro-inflammatory stimuli were added to the culture medium, including:

Interleukin-1 (IL-1): 3 ng/ml
Interferon-gamma (IFN-γ): 3 ng/ml
Tumor necrosis factor-alpha (TNF-α): 5 ng/ml
Lipopolysaccharide (LPS): 100 ng/ml The cells were incubated in the presence of the corresponding stimulus for periods ranging form 30 minutes to 48 hours, and then they were collected by trypsin digestion, and lysed in RIPA buffer (50 mM Tris-HCl pH 7.4, 150 mM NaCl, 1 mM PMSF (phenyl-methylsulphonylfluoride), 1 mM EDTA (ethylenediaminetetraacetic acid), 5 µg/ml Aprotinin, 5 µg/ml Leupeptin, 1% Triton x-100, 1% Sodium deoxycholate, 0.1% SDS) containing protease inhibitors. Cell lysates were then used in a western blot experiment using an IDO-specific monoclonal antibody (mouse monoclonal IgG, clone 10.1, from Upstate cell signaling solutions). Also, RNA was isolated from the treated cells, and tested by reverse transcription—polymerase chain reaction (RT-PCR) experiments using primers specific for the IDO cDNA (GenBank Accession No. M34455 (GI:185790))

```
forward
5' GGATTCTTCCTGGTCTCTCTATTGG 3';

backward:
5' CGGACTGAGGGATTTGACTCTAATG 3').
```

II. Results

Figure 3:
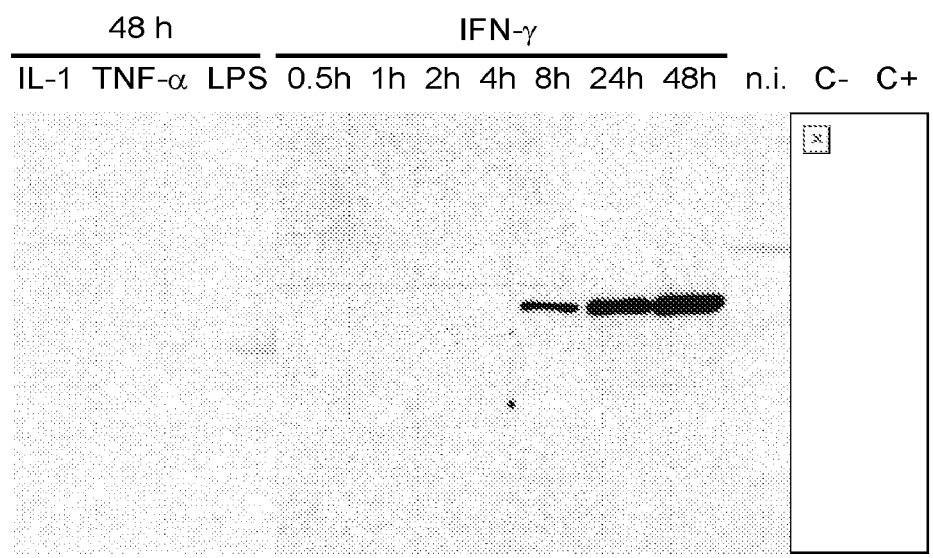
FIG. 3 shows the analysis of IDO expression after incubating the cells provided by the instant invention isolated from human adipose tissue with different pro-inflammatory reagents for different time periods, detected by means of RT-PCR (FIG. 3A) or western blotting (FIG. 3B). IL-1, interleukin 1; TNF-α, tumour necrosis factor-alpha; LPS, lipopolysaccharide; IFN-γ, interferon-gamma; C−, negative control; C+, positive control; n.i., cells not induced with IFN-γ. GAPDH (glyceraldehyde-3-phosphate dehydrogenase) is used as loading control of the RT-PCR.
Figure 3:
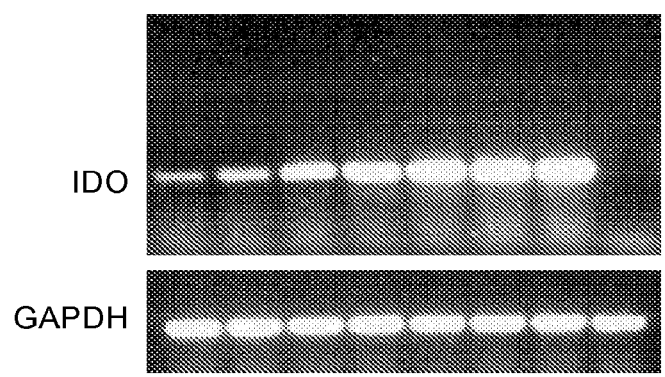

The results of this experiment [FIGS. 3A (RT-PCR) and 3B (western blotting)] show that the cells provided by the instant invention do not express IDO constitutively. The IDO mRNA is induced after 2 hours of IFN-γ stimulation, but the expression of the protein can only be detected between 8-24 hours of induction.

Figure 4:
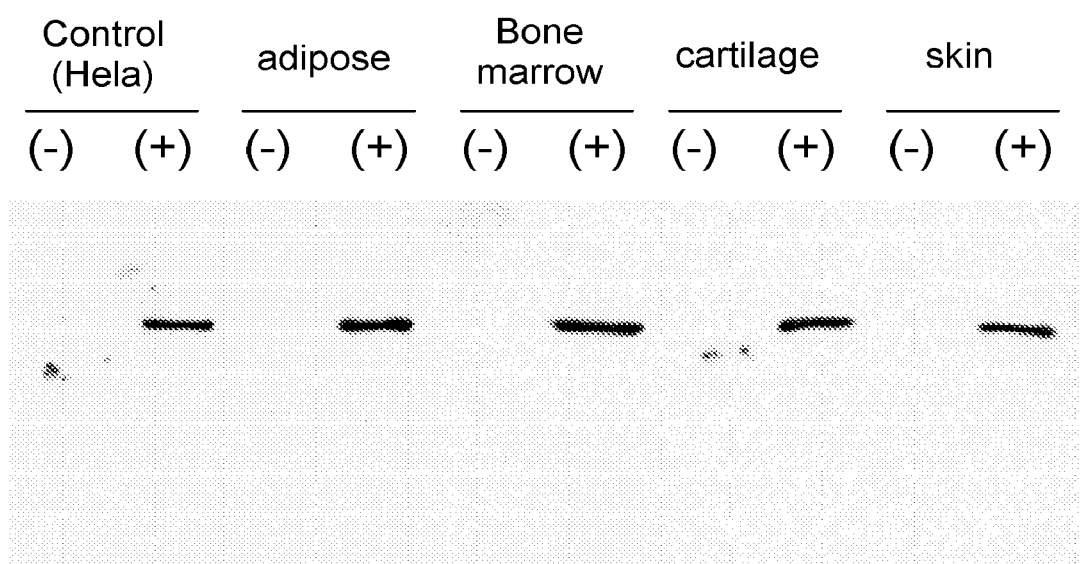
FIG. 4 shows the western blotting detection of IDO expression after 48 hours of IFN-γ treatment of the cells provided by the instant invention isolated from different human tissues (adipose, bone marrow, cartilage, and skin). Ctrl−, negative control (culture medium); Ctrl+, positive control; (−), cells not treated with IFN-γ; (+), cells treated with IFN-γ for 48 hours.

Similar results were obtained when the cells of the invention were isolated from other human tissues, including: bone marrow, articular cartilage, and skin (FIG. 4).

Example 3

Tumorigenic Behaviour

I. Material and Methods

This experiment was performed with cells of the invention isolated from human adipose tissue as described in Example 1. The cell samples were cultivated for 2-7 weeks prior to the subcutaneous implantation in immunodeficient mice ($5\times10^6$ cells/mouse). The mice were nu/nu strain obtained from Charles River Laboratories. Mice lacked thymus and were T-cell deficient. The implanted mice were followed-up for 4 months prior to sacrifice and pathological study.

Pathological study: A necropsy was performed on all animals. The animals were examined for gross abnormalities in the brain, lungs, heart, liver, kidneys, spleen, abdominal lymph nodes and injection site. Tissues were collected for a histological examination (parafin section and hematoxilineosin (H&E) staining), including injection site, lungs and lymph nodes.

The teratome cellular line (N-TERA) was used as a positive control, which was implanted under identical conditions.

II. Results

The results show that, whereas all mice implanted with teratoma cells developed tumours after a few weeks, none of the animals implanted with the cells of the invention developed tumours within the first 4 months following implantation [data not shown].

Example 4

Treatment of Experimentally-Induced IBD in Mice

I. Materials and Methods

Colitis was induced in Balb/c mice (6-8 weeks old, Jackson Laboratories, Bar Harbor, ME) as previously described (Neurath, M. F., et al. 1995. Antibodies to IL-12 abrogate established experimental colitis in mice. *J. Exp. Med.* 182, 1281-1290). In brief, mice were lightly anesthetized with halothane, and a 3.5 F catheter was inserted intrarectally 4 cm from the anus. To induce colitis, 100 µl of 50 or 30 mg/ml of TNBS (2,4,6-trinitrobenzene sulfonic acid) (Sigma Chemical Co, St. Louis, MO) in 50% ethanol (to break the intestinal epithelial barrier) was slowly administered into the lumen via the catheter filled to a 1 ml syringe. Control mice received 50% ethanol alone (100 µl). Animals were treated intrarectally with different numbers of the cells of the invention obtained from human adipose tissue as described in Example 1 ($0.3 \times 10^6$ and $1 \times 10^6$ cells, suspended in phosphate-buffered saline, PBS) 12 hours after TNBS instillation. In some experiments, said cells were pretreated with 200 U/ml IFN-γ for 24 hours before injection. Animals were monitored daily for survival, appearance of diarrhea, and loss of body weight (FIGS. 5, 6 and 7).

II. Results

Figure 5:
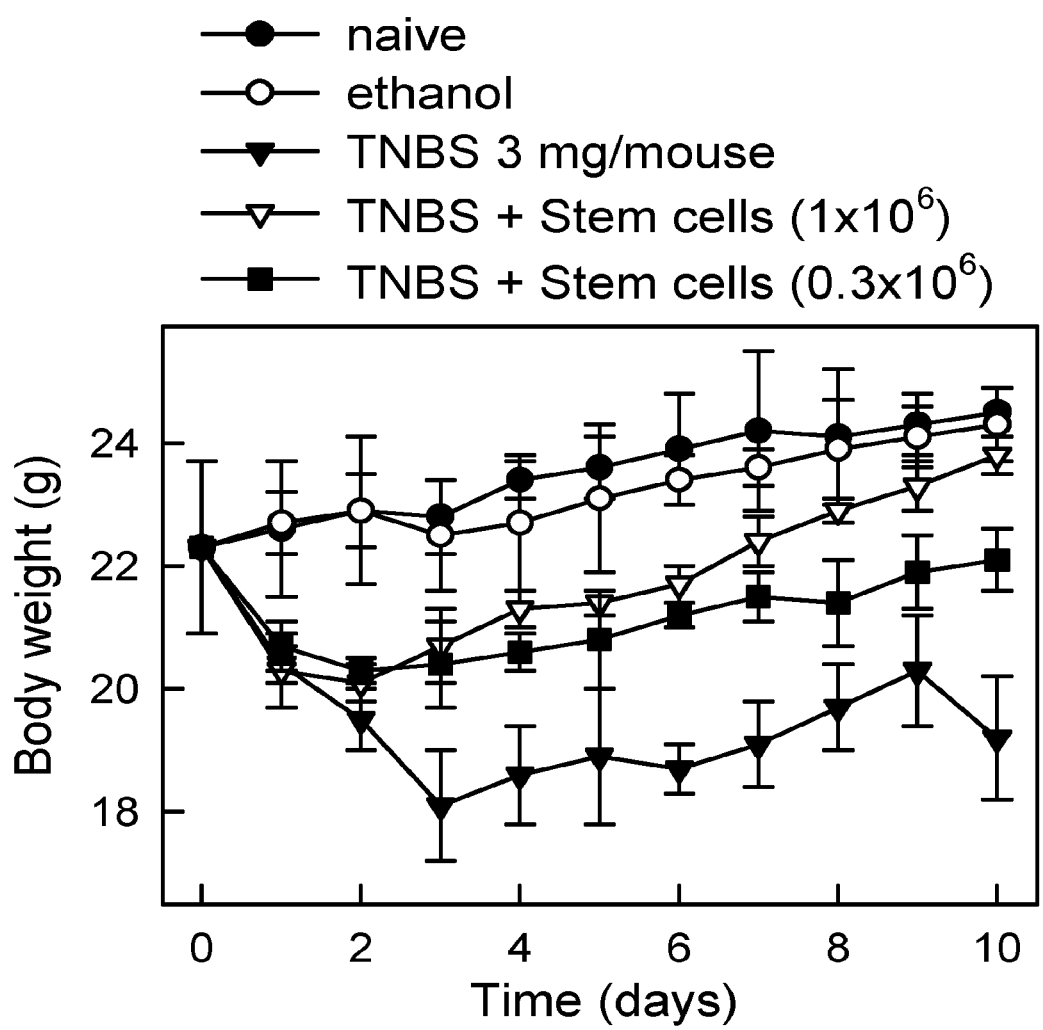
FIG. 5 shows loss of body weight in mice treated with TNBS (2,4,6-trinitrobenzene sulfonic acid) administration. The figure shows a dose-dependent improvement of weight gained after the administration of the cells provided by the instant invention isolated from human adipose tissue. After 10 days mice that received $1 \times 10^6$ cells showed no significant weight difference compared to the control group.
Figure 6:
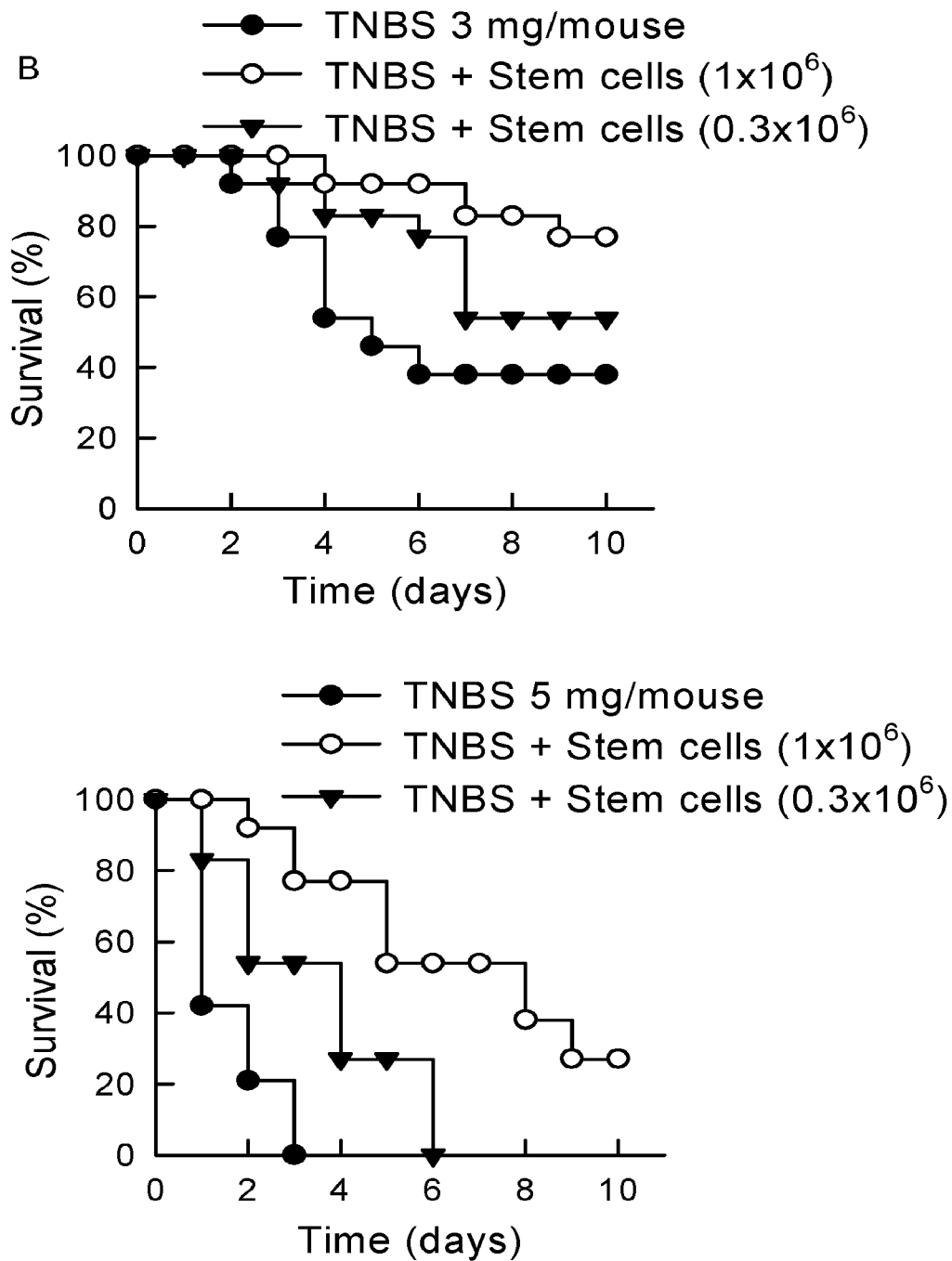
FIG. 6 shows survival rate of TNBS treated mice after administration of the cells provided by the instant invention isolated from human adipose tissue. Again, a dose dependency can be observed with $1 \times 10^6$ cells showing a stronger effect than $0.3 \times 10^6$ cells, although in both cases the cells significantly improved the survival rate of the TNBS treated mice.

As shown in FIG. 5 there was a dose-dependent improvement of weight gained after the administration of the cells of the invention. Indeed, a dose dependency can be observed in FIG. 6 with $1 \times 10^6$ cells showing a stronger effect than $0.3 \times 10^6$ cells. In both cases the cells improved the survival rate of the TNBS treated mice significantly.

Figure 7:
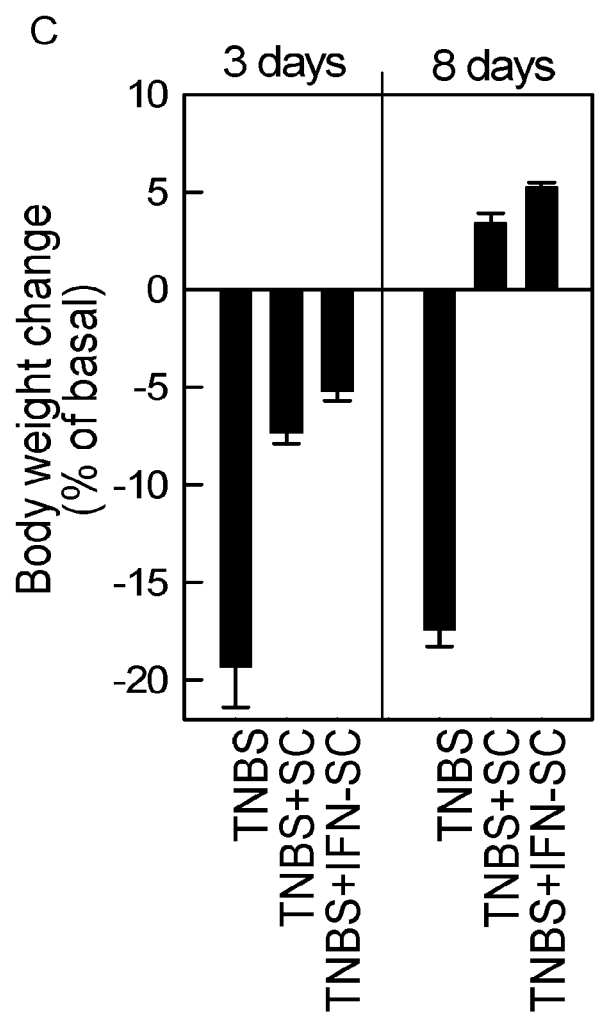
FIG. 7 shows the comparison of body weight in TNBS treated mice after administration of $1 \times 10^6$ cells provided by the instant invention isolated from human adipose tissue and $1 \times 10^6$ of the same cells pre-stimulated with 30 ng/ml IFN-γ during 48 hours. The graph shows the severe weight loss in TNBS treated mice and a clear improvement after 3 days in mice that received cells. After 8 days these mice even showed a weight gain, whereas the control mice (TNBS treated mice without cell administration) still showed a severe weight loss. Furthermore, IFN-γ pre-stimulated cells showed a faster and stronger recuperation from the TNBS treatment than non-prestimulated cells.

Furthermore, IFN-γ-pre-stimulated cells showed a faster and stronger recuperation from the TNBS treatment than non-prestimulated cells (FIG. 7). The graph shows that TNBS treated mice lost weight dramatically and a clear improvement in mice that received cells.

Example 5

Treatment of Experimentally-Induced Inflammatory Bowel Disease (IBD) in Mice—additional experiments:

I. Materials and Methods

In an extension of the same experiments of Example 4, Colitis was induced in Balb/c mice (6-8 weeks old, Jackson Laboratories, Bar Harbor, ME) as previously described (Neurath, M. F., et al. 1995. Antibodies to IL-12 abrogate established experimental colitis in mice. *J. Exp. Med.* 182, 1281-1290). In brief, mice were lightly anesthetized with halothane, and a 3.5 F catheter was inserted intrarectally 4 cm from the anus. To induce colitis, 100 µl of 50 or 30 mg/ml of TNBS (2,4,6-trinitrobenzene sulfonic acid) (Sigma Chemical Co, St. Louis, MO) in 50% ethanol (to break the intestinal epithelial barrier) was slowly administered into the lumen via the catheter filled to a 1 ml syringe. Control mice received 50% ethanol alone (100 µl). Animals were treated intrarectally or intraperitoneally (i.p.) with different numbers of the cells of the invention obtained from human adipose tissue (ASC) as described in Example 1 ($0.3 \times 10^6$ and $1 \times 10^6$ cells, suspended in phosphate-buffered saline, PBS) 12 hours after TNBS instillation. In some experiments, said cells were pretreated with 200 U/ml IFN-γ for 24 hours before injection. Also, in some experiments, cells were labeled with CFSE (a fluorescent probe) before administration to the mice. Animals were monitored daily for survival, appearance and severity of diarrhea, and loss of body weight. Serum was collected and protein extracts were obtained from colons at the acute phase of the disease (day 3). Cytokine/chemokine contents in protein extracts and in serum were determined by ELISA. The presence of CSFE-labeled cells in the mesenteric lymph nodes were analyzed by flow cytometry.

II. Results

In all cases, mice treated with the cells of the invention (ASCs) showed a clear improvement in their inflammatory symptoms compared with non-treated animals. The improvement was dose-dependent and statistically significant in all parameters tested, when cells were administered locally (intra-rectally) or systemically (i.p.), although this last route seems to be more effective. As previously shown in FIG. 5 there was a dose-dependent improvement of weight gained after the administration of the cells of the invention. Indeed, a dose dependency can be observed in FIGS. 6, 7 and 8 with $1 \times 10^6$ cells showing a stronger effect than $0.3 \times 10^6$ cells. In both cases the cells improved the survival rate of the TNBS treated mice significantly.

Figure 8:
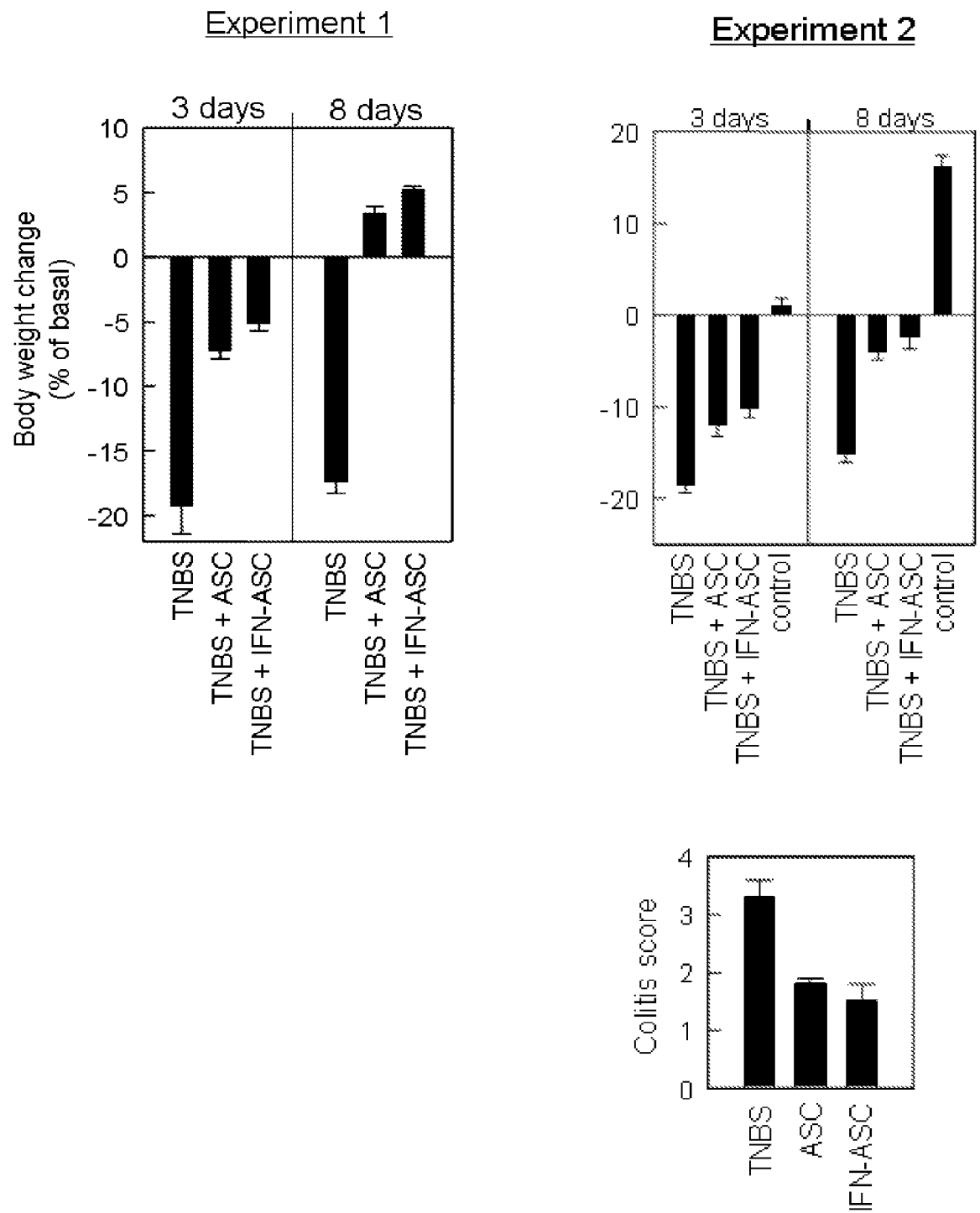
FIG. 8 shows the data of FIG. 7 as "Experiment 1" and in addition data from an additional dataset "Experiment 2" described in Example 5. The graph shows that TNBS treated mice lost weight dramatically and a clear improvement in mice that received cells. This improvement was also measurable by the severity of colitis

Furthermore, IFN-γ-pre-stimulated cells showed a faster and stronger recuperation from the TNBS treatment than non-prestimulated cells (FIG. 8). The graph shows that TNBS treated mice lost weight dramatically and a clear improvement in mice that received cells. This improvement was also measurable by the severity of colitis.

Figure 9:
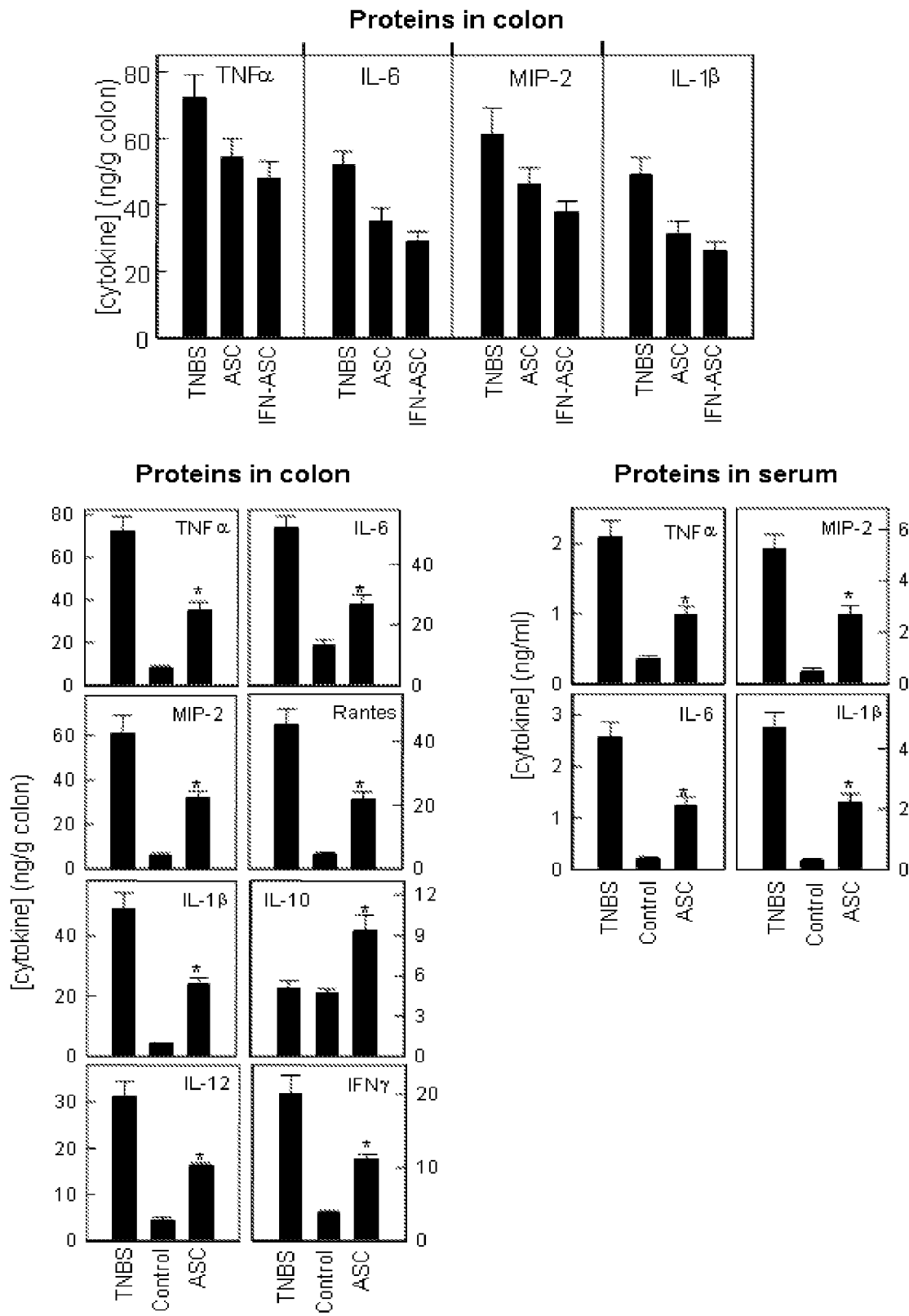
FIG. 9 shows that all proinflammatory cytokines (TNF-a, IL-6, IL-1b, IL-12, and IFNγ) and chemokines (MIP-2 and RANTES) tested, both in the colon (local response) and in the serum (systemic response), were lower in cell-treated animals compared with the non-treated mice.
Figure 10:
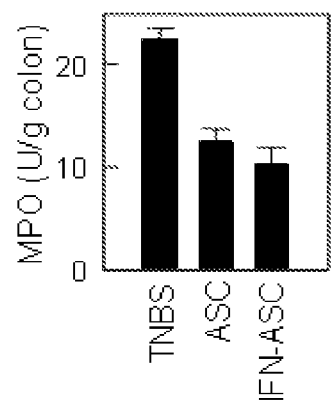
FIG. 10 shows that neutrophil infiltration, as measured by MPO activity was lower in ASC-treated animals, and even lower when cells were pre-stimulated with IFN-γ

The inflammatory immune response is clearly diminished in animals treated with the cells of the invention. As shown in FIG. 9, all proinflammatory cytokines (TNF-a, IL-6, IL-1b, IL-12, and IFNγ) and chemokines (MIP-2 and RANTES) tested, both in the colon (local response) and in the serum (systemic response), were lower in cell-treated animals compared with the non-treated mice. This inhibitory response was enhanced in animals treated with cells pre-stimulated with IFNγ. On the other hand, the immunoregulatory cytokine IL-10 was increased in the colon of ASC-treated mice, comparing with both non-treated TNBS-injured and control animals. Also, neutrophil infiltration, as measured by MPO activity was lower in ASC-treated animals, and even lower when cells were pre-stimulated with IFNγ (FIG. 10).

Figure 11:
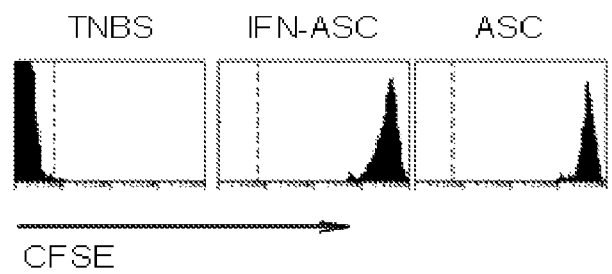
FIG. 11 shows that CFSE labeled cells were localized in the draining lymph nodes of treated animals by means of cell cytometry. This is the localization expected if the administered cells were functioning as APCs.

The labeled cells were localized in the draining lymph nodes of treated animals by means of cell cytometry (FIG. 11). This is the localization expected if the administered cells were functioning as APCs.

Example 6

Induction of APC Markers in the Cells of the Invention after IFNγ Stimulation

I. Materials and Methods

The cells of the invention were obtained from human subcutaneous adipose tissue (ASCs) as described in Example 1. After a minimum of 3 culture passages, the cells were incubated in standard culture medium or in culture medium containing 3 ng/ml IFNγ for 4 days. After that, the cells were stained for some surface markers related with the immune response (specifically related with the activity of antigen presenting cells (APCs)). These markers included the following:

HLA-II (DP, DQ, DR). This receptor presents fragments of foreign antigens to T cells, initiating the adaptive immune response (it is the first signal for T cell activation). The cells of the invention do not express HLA-II constitutively. The antibody used was obtained from Serotec.

CD40. This protein binds to CD40L, which is expressed in the surface of activated T cells. The cells of the invention express undetectable or very low levels of CD40 constitutively. The antibody used was obtained from Serotec.

ICAM-1 (CD54). Is the major protein involved in the binding between T cells and APCs. Its expression is needed for other interactions between APCs and T cells to be carried out properly. The cells of the invention express low-medium levels of ICAM-1 constitutively. The antibody used was obtained from Serotec.

Members of the B7 family of co-stimulatory proteins (they deliver the second signal for T cell activation):
CD80 (B7-1). Antibody obtained from Serotec.
CD86 (B7-2). Antibody obtained from Serotec.
ICOSL (B7-H2). Antibody obtained from e-Bioscience.
B7-H4. Antibody obtained from e-Bioscience.
PD-L1 (B7-H1). Antibody obtained from e-Bioscience.
PD-L2 (B7-DC). Antibody obtained from e-Bioscience.

The first four deliver mainly a stimulatory signal (promoting induction of T cell effector clones), while PD-L1 and PD-L2 are mainly tolerogenic (promoting induction of T cell anergy-inactivation). None of them are expressed by the cells of the invention constitutively.

II. Results

Figure 12:
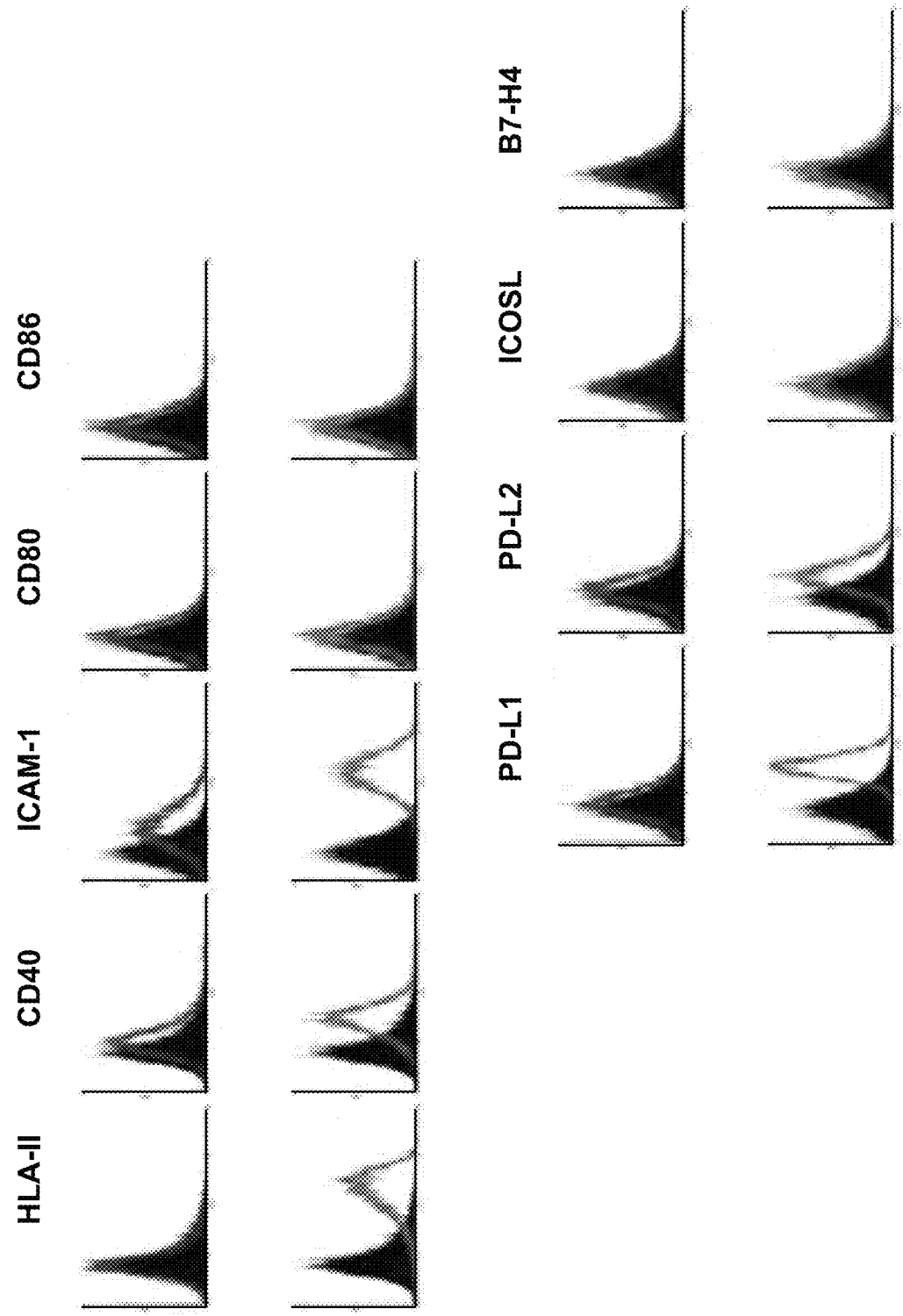
FIG. 12 shows induction of APC markers in human ASCs by IFN-γ treatment. Upper row: cytometric histograms of untreated ASCs; lower row, cytometric histograms of ASCs after treatment with IFN-γ for 4 days. Isotype controls are shown shaded in black.

After IFNγ treatment, the cells of the invention induce the expression of HLA-II, PD-L1 and PD-L2, and a strong upregulation of CD40 and ICAM-1. The results of this experiment are shown in FIG. 12.

These results are very relevant because, together with the induction of IDO activity, they demonstrate that the cells of the invention, upon IFNγ treatment, display a phenotype characteristic of tolerogenic APCs.

Example 7

Treatment of Collagen-Induced Arthritis (CIA) with ASCs
I. Materials and Methods Experimental arthritis was induced in DBA1/Jlac male mice (6-8 weeks of age) by injecting subcutaneously (s.c.) an emulsion containing 200 μg of chicken type II collagen (CII) in complete Freund's adjuvant (CFA) and 200 μg of *Mycobacteterium tuberculosis* H37RA. The evolution of CIA was followed daily by two different technicians, by measuring the inflammation-redness-ankylosis of the joints of upper and lower limbs, according to a pre-established scoring system.

When clinical symptoms showed the establishment of CIA (day 23 post-immunization, p.i.), animals were injected i.p. daily for 5 days with $2 \times 10^5$ cells of the invention obtained from human adipose tissue as described in Example 1 (ASCs), or with PBS as control. Alternatively, CIA mice were injected intraarticularly (i.a.) once in one of the affected joints. The evolution of the treated animals were followed as previously described, and at day 50 p.i. they were euthanized. Several parameters were measured in the blood and the joints, including: joint cytokines, serum cytokines, immunoglobin isotypes, as well as phenotype and cytokine production of lymphocytes.

II. Results

Figure 13:
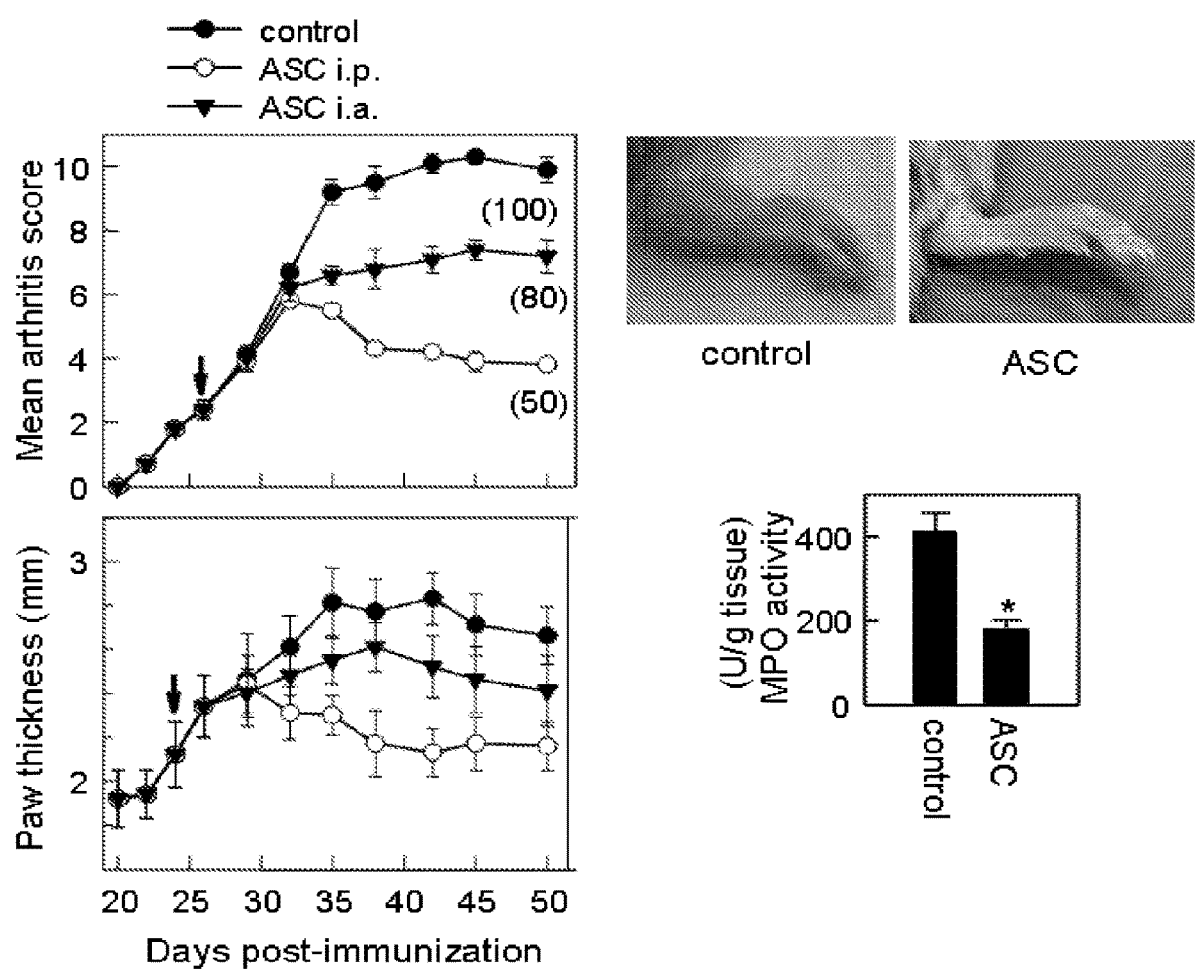
FIG. 13 shows the cells of the invention decrease CIA incidence and severity. A, Severity of arthritis, assessed by clinical scoring or paw thickness measurement, in mice with established CIA injected. Numbers in parenthesis represent incidence of arthritis (% mice with arthritis score >2 at day 50) in control, i.p. and i.a. groups. Images show representative examples of the paw swelling in mice of the different experimental groups (control and ASC i.p.). n=8-11 mice per group. p<0.001 versus control after day 32. Myeloperoxidase (MPO) activity measuring neutrophil infiltration in the joints. *p<0.001 versus control.
Figure 14A:
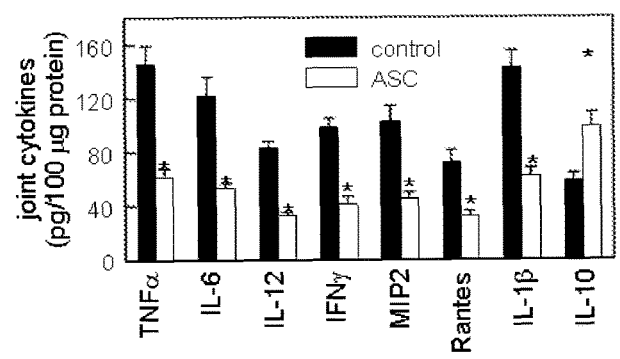
FIG. 14A, shows inhibition of inflammatory response. Systemic and local expression of inflammatory mediators in untreated (control) or ASC-treated CIA mice assayed at day 35 post-immunization. Cytokine/chemokine contents in joints. A paw from an unimmunized mouse was analyzed simultaneously for assessment of the basal response.
Figure 14B:
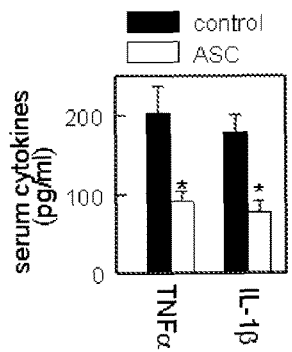
FIG. 14B, shows inhibition of inflammatory response. Systemic and local expression of inflammatory mediators in untreated (control) or ASC-treated CIA mice assayed at day 35 post-immunization. Serum TNFα and IL-1β levels. n=6-8 mice/group. *p<0.001 versus controls.
Figure 15A:
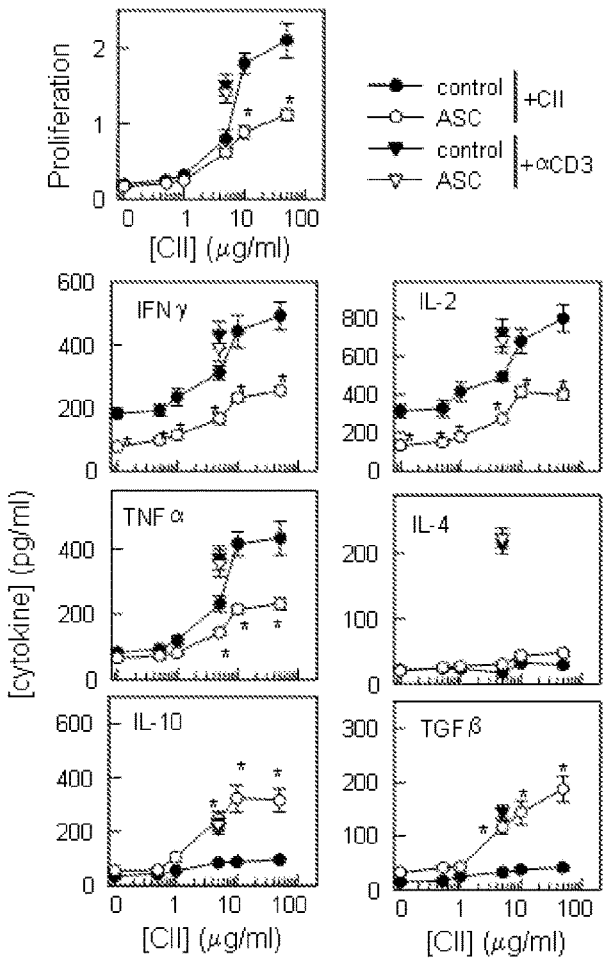
FIG. 15A, shows the cells of the invention downregulate Th1-mediated response in CIA. Proliferative response and cytokine production of draining lymph node (DLN) cells isolated at day 30 from untreated (control) or ASC-treated CIA mice and stimulated in vitro with different concentrations of CII. Stimulation of DLN cells with anti-CD3 antibodies (▼, for untreated CIA mice; ∇, for AM-treated CIA mice) is used for assessment of nonspecific stimulation. A pool of 3 nonimmunized DBA/1 DLN cells was used for assessment of the basal response. n=5 mice/group.
Figure 15B:
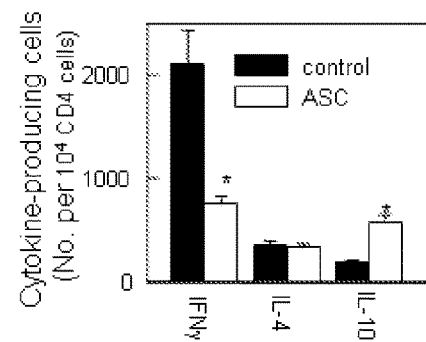
FIG. 15B, shows the cells of the invention downregulate Th1-mediated response in CIA. Number of CII-specific cytokine-producing T cells. DLN cells from untreated (control) or ASC-treated CIA mice were restimulated in vitro with CII (10 μg/ml) and analyzed for CD4 and intracellular cytokine expression by flow cytometry (for IFNγ/TNFα or IL-4/IL-10 expression in gated CD4 T cells). The number of IFNγ-, IL-4- and IL-10-expressing T cells relative to $10^4$ CD4 T cells is shown. Data shown represent pooled values from two independent experiments.
Figure 15C:
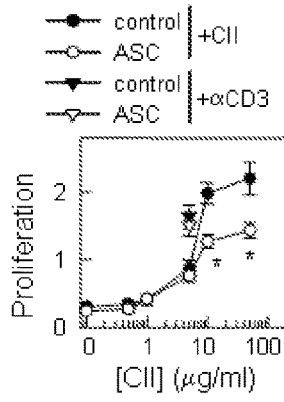
FIG. 15C, shows the cells of the invention downregulate Th1-mediated response in CIA. CII-specific proliferative response in synovial membrane cells isolated from untreated (control) or ASC-treated CIA mice and stimulated in vitro with CII (10 µg/ml) for 48 h. Data show the results of pooled synovial cells from 3 animals per group.
Figure 15D:
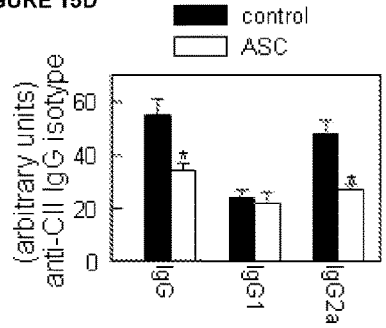
FIG. 15D, shows the cells of the invention downregulate Th1-mediated response in CIA. CII-specific IgG, IgG1 and IgG2a levels in serum collected at day 35 from untreated (control) or ASC-treated CIA mice (8-12 mice/group). *p<0.001 versus controls.

As shown in the FIGS. 13, 14, and 15, the cells of the invention clearly decrease CIA incidence and severity in the mouse model. In particular, the effect on the immune response is consistent with a strong inhibition of the Th1 response (IFN-γ, TNFα, IL-2, IL-1β, IL-6, IL-12, MIP2, RANTES, and IgG2a) without any increase in the Th2 response (IL-4, IgG1), and with the induction of high levels of immunoregulatory cytokines (IL-10 and TGF-β).

Example 8

In Vivo induction of Regulatory T Cells with the Cells of the Invention
I. Materials and Methods In a study similar to the one described in Example 7, effector (CD4$^+$CD25"Foxp3") and regulatory T cells (CD4$^+$CD25$^+$Foxp3$^+$) were isolated from the drain lymph node (DLN) and the synovial membrane of untreated and ASC-treated CIA mice, by means of cell cytometry, and the number of cells in each population was evaluated.

In order to evaluate the capacity of regulatory T cells present in the ASC-treated CIA mice to inhibit the CII-specific effector cells, a proliferative assay was performed in which autoreactive T cells isolated from CIA mice were co-cultured with increasing numbers of DLN T cells (regulatory T cells) from untreated (control) or ASC-treated CIA mice (ratios from 1/64 to 1/1), and stimulated with CII (10 μg/ml) and splenic APCs.

II. Results

Figure 16A:
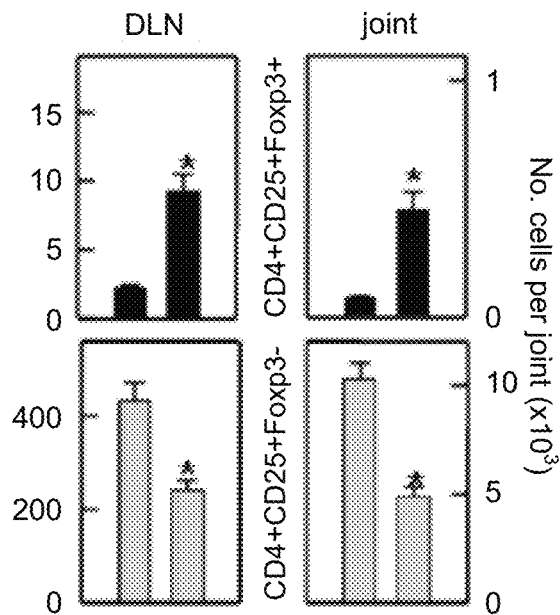
FIG. 16A shows both the DLN and the synovial membrane of CIA mice treated with the cells of the invention induce an increase in the numbers of regulatory T cells ($CD4^+CD25^+Foxp3^+$), without any increase in the numbers of effector T cells, comparing with the untreated (control) CIA mice.
Figure 16B:
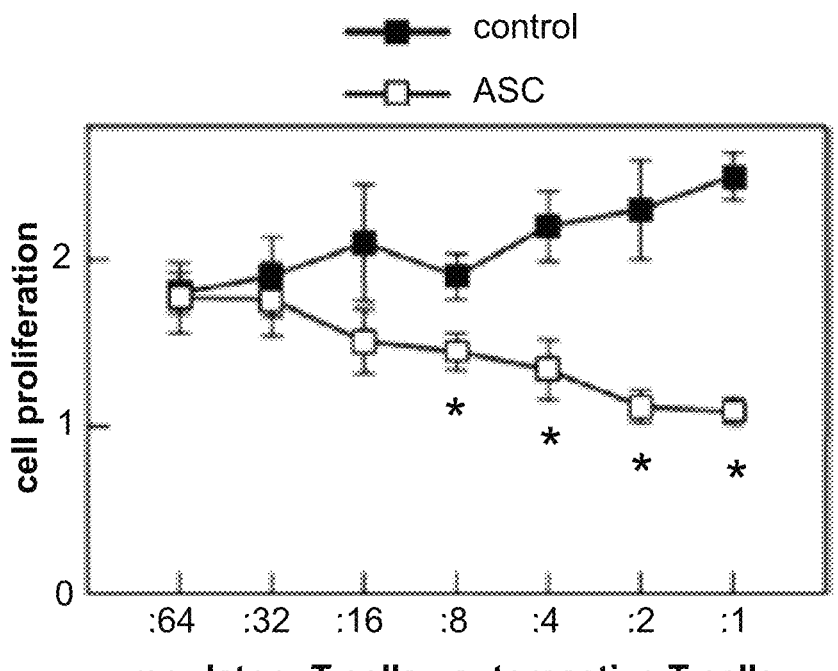
FIG. 16B shows that CIA mice treated with the cells of the invention, but not control (untreated) CIA mice, contain regulatory T cells that specifically inhibit the effector T cell response against CII.

As shown in FIG. 16.A., both the DLN and the synovial membrane of CIA mice treated with the cells of the invention induce an increase in the numbers of regulatory T cells (CD4$^+$CD25$^+$Foxp3$^+$), without any increase in the numbers of effector T cells, comparing with the untreated (control) CIA mice.

The data shown in FIG. 16.B. demonstrates that CIA mice treated with the cells of the invention, but not control (untreated) CIA mice, contain regulatory T cells that specifically inhibit the effector T cell response against CII.

In conclusion, the treatment of an animal model of an experimental autoimmune disease (CIA) with the cells of the invention induces the emergence of antigen-specific regulatory T cells able to suppress the autoreactive T cell effector response.

Example 9

Lymphocyte Proliferation Assay

Figure 17:
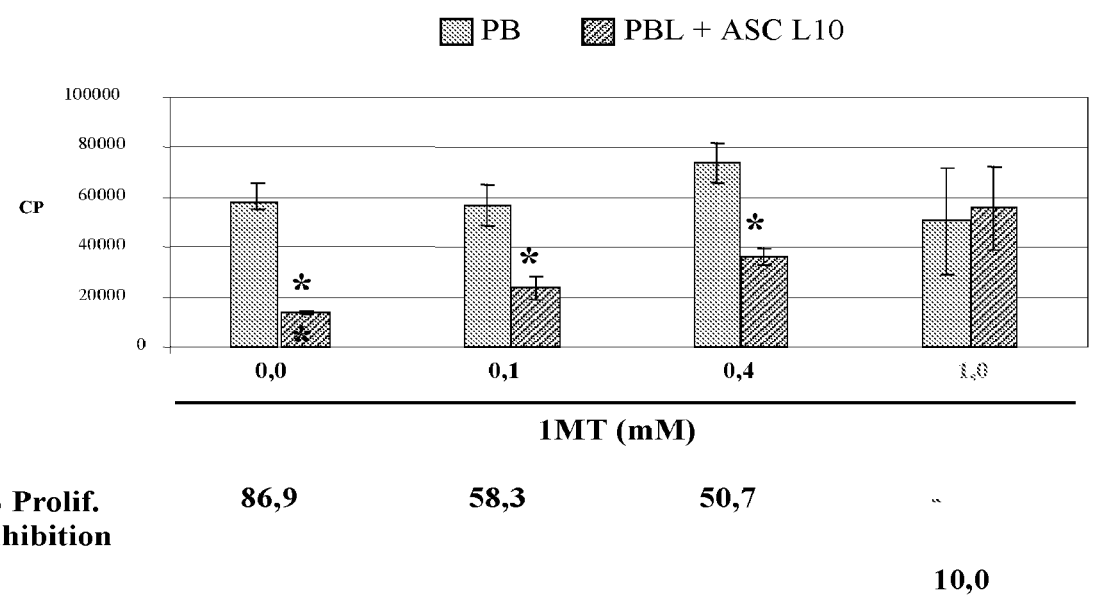
FIG. 17 shows the co-culture of ASCs and lymphocytes results in an inhibition of lymphocyte proliferation.

Adipose derived ASCs of the invention, obtained via the methods of Example 1, were plated at 5000 cells/cm$^2$ with and without 200.000 lymphocytes (activated w/10 μgPHA/ml) and co-cultured for 3 days. Proliferation of the lymphocytes was measured by H3 incorporation. As shown in FIG. 17, the co-culture of ASCs and lymphocytes resulted in an 86% inhibition of lymphocytes proliferation. The addition different concentrations of 1Methyl-trytophan (1-MT) reverted this suppression. 1-MT is a non-metabolizable tryptophan analog. The assay demonstrates the necessity of tryptophan catabolism via IDO to induce the immunosuppressive activity of the cells of the invention Example 10

ASCs Potency (IDO Production) in Relation to Cell Number and IFN-γ Concentration
Materials and Methods
HPLC:
Conventional HPLC was carried out using a Waters 1515 Isocratic HPLC pump, a Waters 717 Autosampler and a Waters 2487 Dual Absorbance Detector
HPLC—Protocol
Fresh solutions in the range of 100 μM to 100 mM of trytophan and kynurenine were prepared in 10% acetonitrile in potassium-phosphate buffer (50 mM pH 6.0). From these stock solutions 50 µl tryptophan and 10 µl kynurenine and 940 µl BSA (70 g/l) or 10% FCS were combined to make up the control sample and stored at −80° C.

Sample preparation: 200 µl or more of supernatant from samples (cell cultures) were collected in Eppendorf tubes and stored at −80° C. Samples and control samples were thawed and 200 µl 50 mM potassium-phosphate buffer pH6.0 was added to each 200 µl sample in an Eppendorf tube. 50µl of 2M TCA (trichloroacetic acid) was added to the Eppendorf tube. The tube was vortexed and centrifuged for 10 min at 13.000 g at 4° C. From the Eppendorf tube 150 µl was removed for measuring.

Column Preparation for HPLC Measurement

The HPLC column was prepared as known in the art and equilibrated with mobile phase, which consisted of 40 mM sodium-citrate pH5—in 5% acetonitrile. 50 µl of above described sample of 150 µl sample was injected into the column (C18 reverse phase). Separation occurs by an isocratic flow rate of 700 µl/min. The photometric detection of L-kynurenine occurs at 365 nm, for L-tryptophan at 280 nm.

Results

Figure 18:
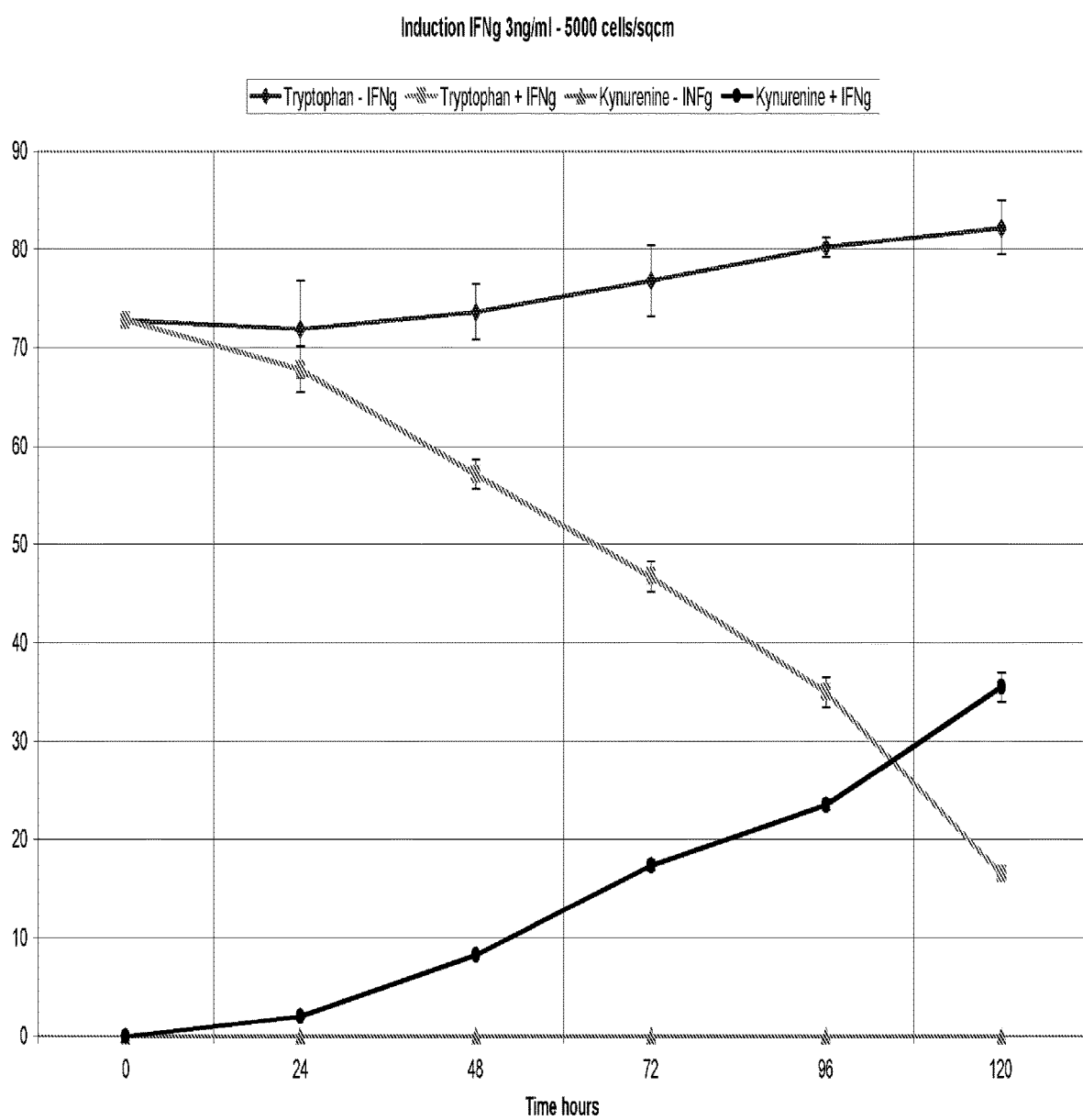
FIG. 18 shows that ASCs plated at 5000 cell/$cm^2$ and stimulated at 3 ng/ml IFN-γ for up to 120 hours produce IDO, the activity of which is measured by the metabolization of Tryptophan and production of Kynurenine using HPLC.
Figure 19:
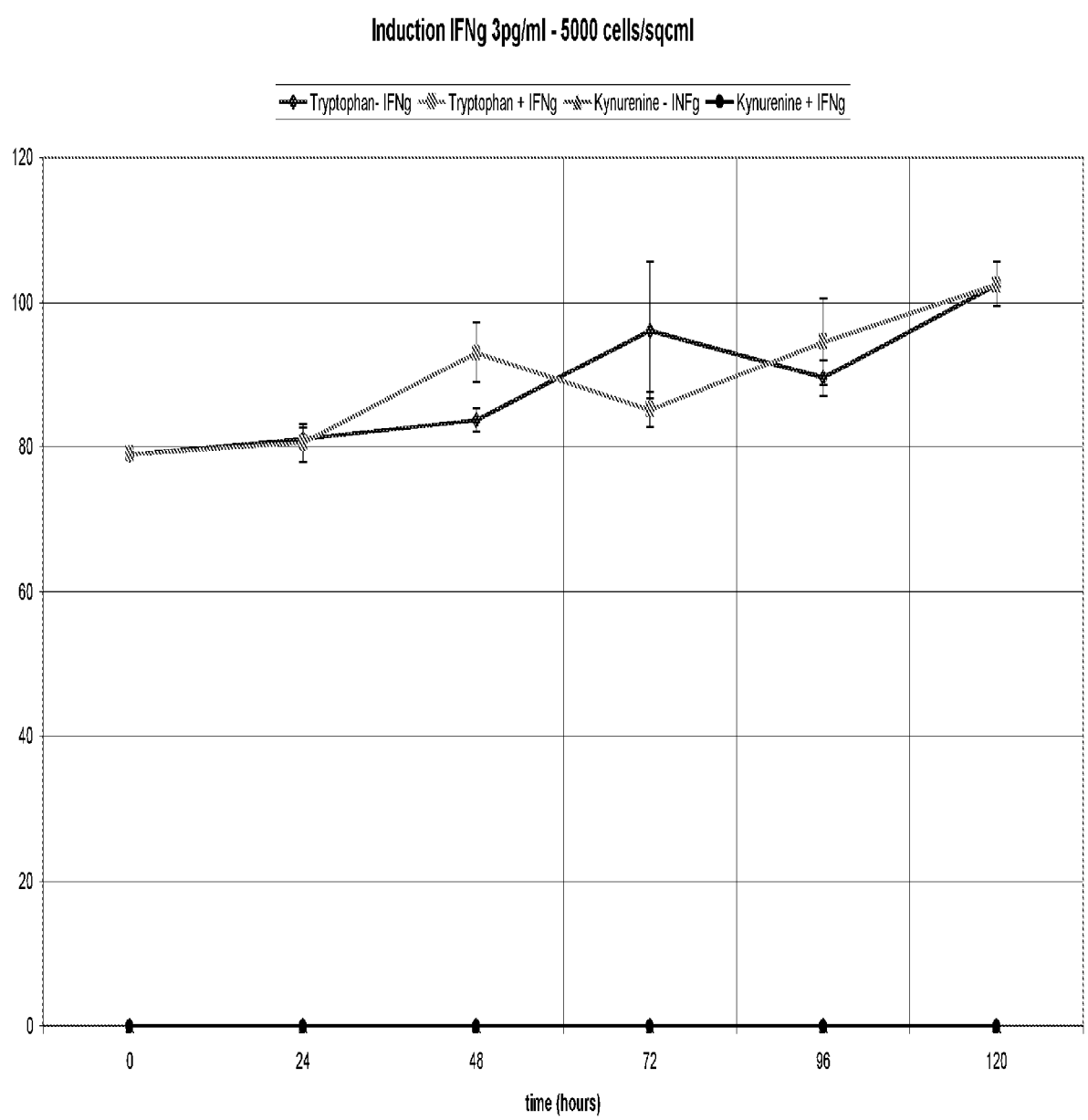
FIG. 19 shows that ASCs plated at 5000 cell/$cm^2$ and stimulated at 3 pg/ml IFN-γ for up to 120 hours fail to produce IDO. No Kynurenine could be detected.
Figure 20:
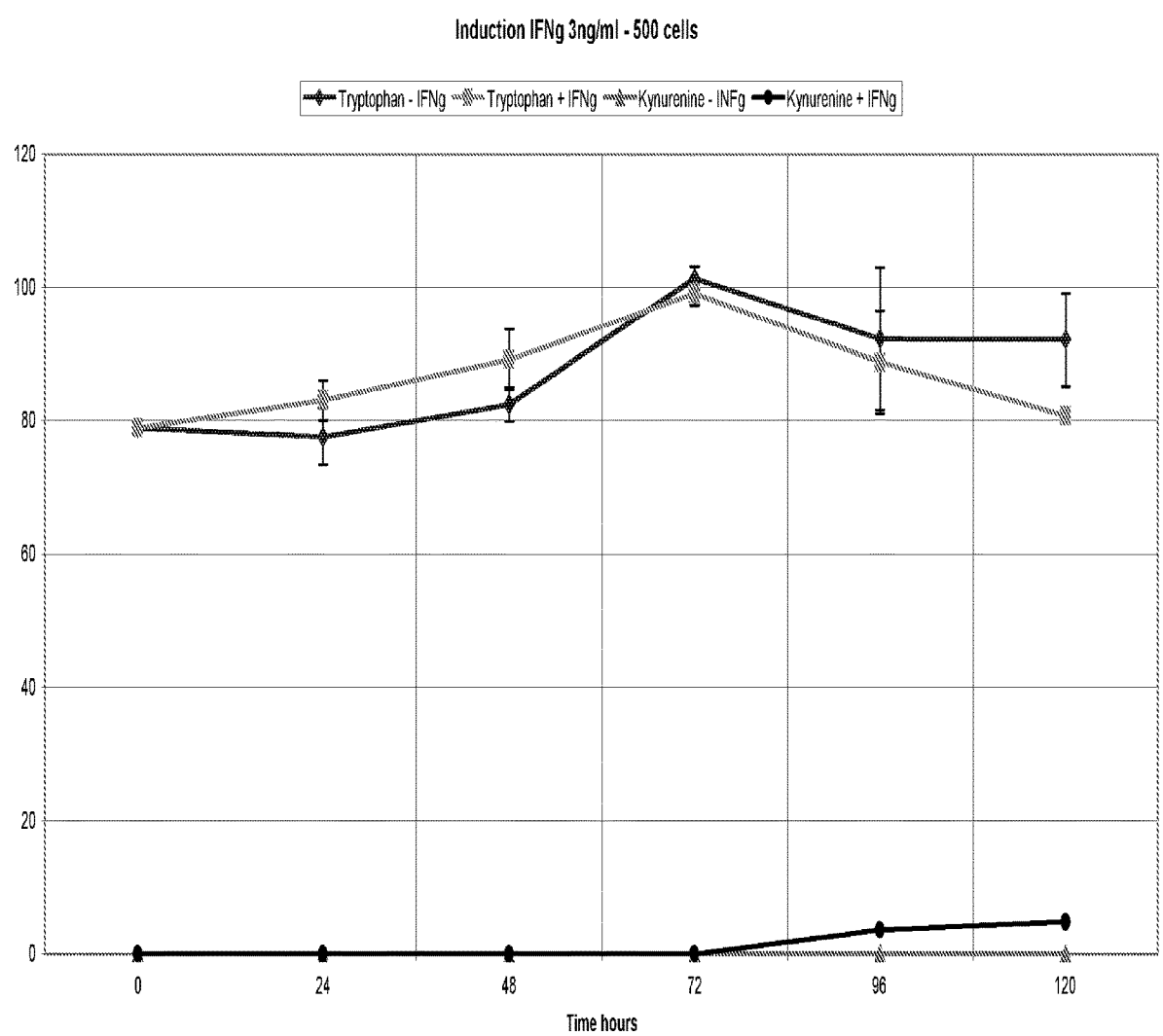
FIG. 20 shows that ASCs plated at 500 cell/$cm^2$ and stimulated at 3 ng/ml IFN-γ for up to 120 hours fail to produce significant amounts IDO.

As shown in FIG. 18, ASCs plated at 5000 cell/cm$^2$ and stimulated at 3 ng/ml IFN-γ for up to 120 hours produce IDO, the activity of which is measured by the metabolization of tryptophan and production of kynurenine using HPLC. ASCs plated at 5000 cell/cm$^2$ and stimulated at 3 pg/ml IFN-γ for up to 120 hours did not produce IDO. No kynurenine could be detected (FIG. 19). Similarly, ASCs plated at 500 cell/cm$^2$ and stimulated at 3 ng/ml IFN-γ for up to 120 hours did not produce significant amounts of IDO (FIG. 20).

Example 10

Ability of ASCs to Phagocytose Small Molecules

Materials and Methods 4 kda—Dextran-FITC (Sigma) was added to the cells of Example 1 for 24 hours in culture. The cell were washed and analyzed for the incorporation of the fluorescent FITC.

Results

Figure 21A:
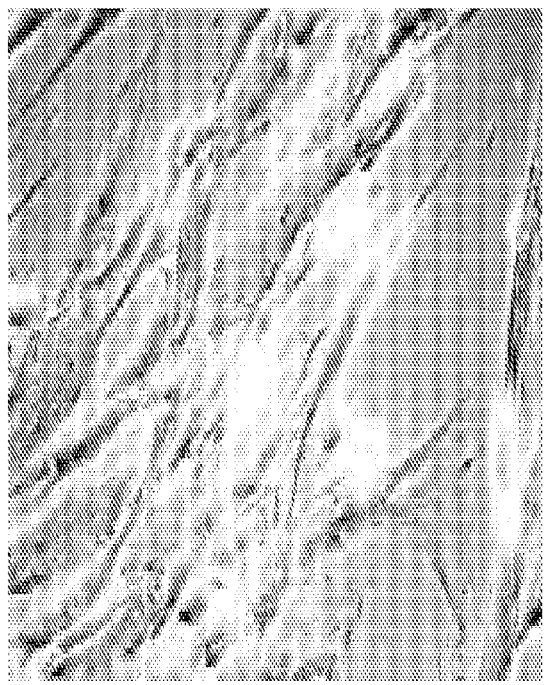
FIG. 21A shows cells which have phagocytosed dextran FITC in a bright field image.
Figure 21B:
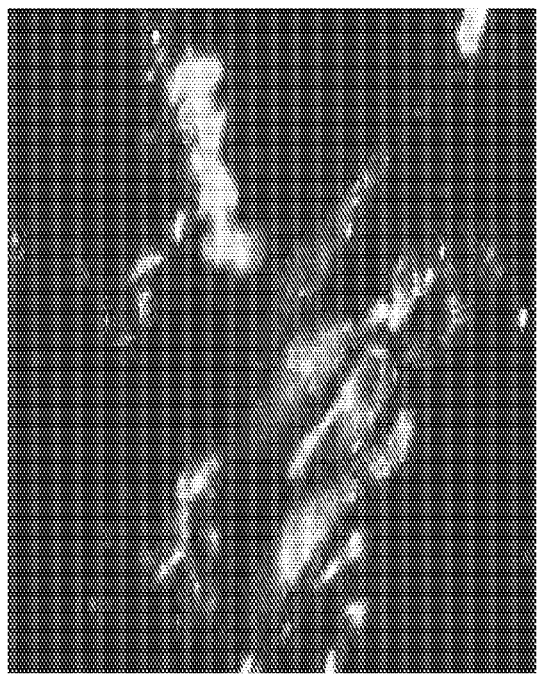
FIG. 21B shows the same population using fluorescence microscopy using Green Fluorescent Protein filters.

FIG. 21A shows the cells bright field image of the washed cell population. FIG. 21B shows the same population using fluorescence microscopy using Green Fluorescent Protein filters known in the art. The uptake of the fluorescent marker visible in FIG. 21 B shows that the cells are able to phagocytose small weight molecules and this indicates that these cells are capable of antigen-presentation via HLA class II induced by additional treatment of the cells with IFNγ.

The invention claimed is:

1. A method of treating an inflammatory bowel disease in a subject comprising systemically administering to the subject an isolated cell population from adipose tissue that has not been stimulated with interferon-gamma (IFN-γ), wherein the cell population comprises a therapeutically effective amount of cells that express indolamine 2,3-dioxygenase (IDO) when stimulated with IFN-γ, wherein the cells comprised in the cell population have the following characteristics:
   (i) the cells when administered do not express the markers CD11b, CD11c, CD14, CD45 and HLAII,
   (ii) the cells do not express IDO constitutively,
   (iii) the cells have the capacity to be differentiated into at least two cell lineages, and
   (iv) the cells are homogeneous.

2. The method of claim 1, wherein the subject is a human.

3. The method of claim 1, wherein the cell population is a human cell population.

4. The method of claim 1, wherein the cells are negative for at least one or both of the following surface markers: CD31 and CD133.

5. The method of claim 1, wherein the cell population was prepared by a preparation method that comprises passaging cells at least three times.

6. The method of claim 1, wherein the cell population is administered intrarectally or intraperitoneally.

7. The method of claim 1, wherein the inflammatory bowel disease is Crohn's disease.

8. The method of claim 1, wherein said inflammatory disease is refractory to one or more anti-inflammatory agents.

9. The method of claim 1, wherein the cells of the cell population are prepared by culturing cells from adipose tissue without differentiation on a solid surface in the presence of a suitable culture medium or a suitable serum, incubating the cells under conditions which allow the cells to adhere to the solid surface and proliferate, selecting cells that remain adhered to the solid surface after at least two passages to produce the population of cells.

10. The method of claim 1, wherein the cell population comprising the therapeutically effective amount of cells that express IDO when stimulated with IFN-γ is selected by assaying a sample of the cell population by stimulation of the sample with IFN-γ and detection of IDO activity.

11. The method of claim 1, wherein the cell population is used in conjunction with non-steroidal anti-inflammatory drugs (NSAIDs), steroidal anti-inflammatory drugs, beta-agonists, anticholinergic agents, or methyl xanthines.

12. The method of claim 11, wherein the NSAID is selected from ibuprofen, celecoxib, diclofenac, etodolac, fenoprofen, indomethacin, ketoralac, oxaprozin, nabumentone, sulindac, tolmentin, rofecoxib, naproxen, ketoprofen and nabumetone.

13. The method of claim 11, wherein the steroidal anti-inflammatory drug is selected from glucocorticoids, dexamethasone, cortisone, hydrocortisone, prednisone, prednisolone, triamcinolone, azulfidine and eicosanoids.

\* \* \* \* \*

```
                        SEQUENCE LISTING

<160> NUMBER OF SEQ ID NOS: 2

<210> SEQ ID NO 1
   <211> LENGTH: 25
   <212> TYPE: DNA
   <213> ORGANISM: Artificial Sequence
   <220> FEATURE:
   <223> OTHER INFORMATION: Primer

<400> SEQUENCE: 1
ggattcttcc tggtctctct attgg                                            25

<210> SEQ ID NO 2
   <211> LENGTH: 25
   <212> TYPE: DNA
   <213> ORGANISM: Artificial Sequence
   <220> FEATURE:
   <223> OTHER INFORMATION: Synthetic Construct

<400> SEQUENCE: 2
cggactgagg gatttgactc taatg                                            25
```